US006555572B2

(12) United States Patent
Lauener et al.

(10) Patent No.: US 6,555,572 B2
(45) Date of Patent: Apr. 29, 2003

(54) BENZYLATED PDE4 INHIBITORS

(75) Inventors: Ronald W. Lauener, New Westminster (CA); David L. Burgoyne, Delta (CA); Patrick J. Rebstein, Vancouver (CA); Lloyd F. Mackenzie, Surrey (CA); Yuanlin Zhou, Richmond (CA); Yaping Shen, Port Coquitlam (CA)

(73) Assignee: Inflazyme Pharmaceuticals Ltd., Richmond (CA)

( * ) Notice: Subject to any disclaimer, the term of this patent is extended or adjusted under 35 U.S.C. 154(b) by 0 days.

(21) Appl. No.: 09/810,085

(22) Filed: Mar. 16, 2001

(65) Prior Publication Data

US 2002/0028842 A1 Mar. 7, 2002

Related U.S. Application Data

(60) Provisional application No. 60/190,337, filed on Mar. 16, 2000.

(51) Int. Cl.$^7$ .................. C07D 207/12; A61K 31/38

(52) U.S. Cl. ....................................... 514/445; 548/543

(58) Field of Search ......................... 548/543; 514/445

(56) References Cited

U.S. PATENT DOCUMENTS

| | | | | |
|---|---|---|---|---|
| 3,636,039 | A | 1/1972 | Gruenman et al. | 260/309.7 |
| 4,308,278 | A | 12/1981 | Schneider et al. | 424/273 R |
| 4,950,674 | A | 8/1990 | Yanni et al. | 514/317 |
| 5,066,663 | A | 11/1991 | Hobbs | 514/326 |
| 5,124,455 | A | 6/1992 | Lombardo | 546/181 |
| 5,223,504 | A | 6/1993 | Noverola et al. | 514/263 |
| 5,552,438 | A | 9/1996 | Christensen, IV | 514/520 |
| 5,563,143 | A | 10/1996 | Cohan et al. | 514/256 |
| 5,602,157 | A | 2/1997 | Christensen, IV | 514/362 |
| 5,602,173 | A | 2/1997 | Christensen, IV | 514/371 |
| 5,728,884 | A | 3/1998 | Muller et al. | 548/472 |
| 5,734,051 | A | 3/1998 | Spicer et al. | 544/118 |
| 5,814,651 | A | 9/1998 | Duplantier et al. | 514/394 |
| 5,916,910 | A | 6/1999 | Lai | 514/423 |
| 5,965,730 | A | 10/1999 | Ukita et al. | 544/128 |
| 5,968,945 | A | 10/1999 | Muller et al. | 514/290 |
| 6,004,974 | A | 12/1999 | Duplantier et al. | 514/293 |
| 6,028,086 | A | 2/2000 | Duplantier | 514/352 |

FOREIGN PATENT DOCUMENTS

| | | |
|---|---|---|
| EP | 381 235 B1 | 8/1990 |
| WO | WO 92/12961 | 8/1992 |
| WO | WO 92/19594 | 11/1992 |
| WO | WO 93/07141 | 4/1993 |
| WO | WO 94/12461 | 6/1994 |
| WO | WO 95/00139 | 1/1995 |
| WO | WO 98/34584 | 8/1998 |
| WO | WO 99/18793 | 4/1999 |
| WO | WO 99/34797 | 7/1999 |
| WO | WO 99/34798 | 7/1999 |

OTHER PUBLICATIONS

Ashton et al., "Selective Type IV Phosphodiesterase Inhibitors as Antiasthmatic Agents. The Syntheses and Biological Activities of 3–(Cyclopentyloxy)–4–methoxybenzamides and Analogues," *J. Med. Chem.* 37:1696–1703, 1994.

Bacher et al., "N–Arylrolipram Derivatives as Potent and Selective PDE4 Inhibitors," *Bioorganic & Medicinal Chemistry Letters* 8:3229–3234, 1998.

Beasley et al., "Synthesis and Evaluation of a Novel Series of Phosphodiesterase IV Inhibitors. A Potential Treatment for Asthma," *Bioorganic & Medicinal Chemistry Letters* 8:2629–2634, 1998.

Burnouf et al., "Phosphodiesterases 4 Inhibitors," in James A. Bristol, (ed.), *Annual Reports In Medicinal Chemistry* vol. 33, Academic Press, California, 1998, Chap. 10, pp. 91–109.

Christensen et al., "Molecular Aspects of Inhibitor Interaction With PDE4," in Schudt et al., (eds.), *Phosphodiesterase Inhibitors*, Academic Press, 1996, Chap. 13, 185–207.

Cook et al., "Process Development of the PDE IV Inhibitor 3–(Cyclopentyloxy)–N–(3, 5–dichloropyrid–4–yl)–4–Methoxybenzamide," *Organic Process Research & Development* 2(3):157–168, 1998.

Duplantier et al., "Biarylcarboxylic Acids and –Amides: Inhibition of Phosphodiesterase Type IV versus [$^3$H]Rolipram Binding Activity and Their Relationship to Emetic Behavior in the Ferret," *J. Med. Chem.* 39(1):120–125, 1996.

Essayan, "Cyclic Nucleotide Phosphodiesterase (PDE) Inhibitors and Immunomodulation," *Biochemical Pharmacology* 57(9):965–973, May 1, 1999.

Macdonald et al., "Hunting and Emesis and Efficacy Targets of PDE4 Inhibitors: Identification of the Photoaffinity Probe 8–(3–Azidophenyl)–6–[(4–iodo–1H–1–imidazolyl)methyl] quinoline (APIIMQ)," *J. Med. Chem.* 43(21):3820–3823, 2000.

Newton et al., "Therapeutic Potential and Strategies for Inhibiting Tumor Necrosis Factor–α," *J. of Medicinal Chemistry* 42(13):2295–2314, 1999.

Norman, "PDE4 Inhibitors 1999," *Exp. Opin. Ther. Patents* 9(8):1–18, 1999.

(List continued on next page.)

Primary Examiner—Mukund J. Shah
Assistant Examiner—Hong Liu
(74) Attorney, Agent, or Firm—Seed Intellectual Property Law Group PLLC

(57) ABSTRACT

The present invention is directed to a method for reducing the emetogenic effects of PDE inhibitors, and more particularly is directed to compounds having PDE4 inhibition activity with little or no emetogenic side-effects, and chemical methods including benzylation for preparing such compounds. A benzyl group may be attached to either a carbon or nitrogen atom of a PDE4 inhibitor. Suitable benzylation chemistry is to extract a hydrogen from a PDE4 inhibitor, preferably with a base, and then react the resulting nucleophilic PDE4 inhibitor with a benzylating agent, e.g., benzyl bromide or a derivative thereof.

11 Claims, No Drawings

OTHER PUBLICATIONS

Norman, "PDE4 Inhibitors: Patent and Literature Activity 1999–mid 2000," *Exp. Opin. Ther. Patents* 10(9):1417–1429, 2000.

Piaz et al., "Novel Heterocyclic–Fused Pyridazinones as Potent and Selective Phosphodiesterase IV Inhibitors," *J. Med. Chem.* 40(10):1417–1421, 1997.

Piaz et al., "Phosphodiesterase 4 Inhibitors, Structurally Unrelated to Rolipram, as Promising Agents for the Treatment of Asthma and Other Pathologies," *Eur. J. Med. Chem.* 35:463–480, 2000.

Robichaud et al., "Emesis Induced by Inhibitors of Type IV Cyclic Nucleotide Phosphodiesterase (PDE IV) in the Ferret," *Neuropharmacology* 38:289–297, 1999.

Robichaud et al, "PDE4 Inhibitors Induce Emesis in Ferrets Via a Noradrenergic Pathway," *Neuropharmacology* 40:262–269, 2001.

Souness et al., "Potential of Phosphodiesterase Type IV Inhibitors in the Treatment of Rheumatoid Arthritis," *Idrugs* 1(5):541–553, 1998.

Souness et al., "Immunosuppressive and Anti–Inflammatory Effects of Cyclic AMP Phosphodiesterase (PDE) Type 4 Inhibitors," *Immunopharmacology* 47:127–162, 2000.

Spina, "The Potential of PDE4 Inhibitors in Asthma or COPD," *Current Opinion in Investigational Drugs* 1(2):204–213, 2000.

Tian et al., "Dual Inhibition of Human Type 4 Phosphodiesterase Isostates by (R*,R*)–(±)–Methyl 3–Acetyl–4–[3–(cyclopentyloxy)–4–methoxyphenyl]–3–methyl–1–pyrrolidinecarboxylate," *Biochemistry* 37(19):6894–6904, 1998.

Torphy, "Phosphodiesterase Isozymes Molecular Targets for Novel Antiasthma Agents," *American Journal of Respiratory and Critical Care Medicine* 157(2);351–370, Feb. 1998.

Bärfacker et al., "Rhodium(I)–catalysed Hydrocarbonylation and Silylcarbonylation Reaction of Alkynes in the Presence of Primary Amines Leading to 2–Pyrrolidinones and 4–Silylated 1–Aza–1,3–butadienes," *Tetrahedron* 54(18):4493–4506, Apr. 30, 1998.

Christensen et al., "1,4–Cyclohexanecarboxylates: Potent and Selective Inhibitors of Phosphodiesterase 4 for the Treatment of Asthma," *J. Med. Chem.* 41:821–835, 1998.

Crespo et al., "Design, Synthesis, and Biological Activities of New Thieno[3,2–d]pyrimidines as Selective Type 4 Phosphodiesterase Inhibitors," *J. Med. Chem.* 41:4021–4035, 1998.

Karlsson and Aldous, "Pulmonary–Allergy, Dermatological, Gastrointestinal & Arthritis," *Expert Opinion on Therapeutic Patents* 7(9):989–1003, 1997.

Küsters and Spöndlin, "Influence of Temperature on the Enantioseparation of Rolipram and Structurally Related Racemates on Chiracel–OD," *Journal of Chromatography* 737(2):333–337, Jun. 21, 2001.

Marivet et al., "Inhibition of Cyclic Adenosine–3',5'–Monophosphate Phosphodiesterase From Vascular Smooth Muscle by Rolipram Analogues," *J. Med. Chem.* 32(7):1450–1457, 1989.

Rowley et al., "4–Heterocyclylpiperidines as Selective High–Affinity Ligands at the Human Dopamine D4 Receptor," *J. Med. Chem.* 40:2374–2385, 1997.

CHEMABS Database, STN Accession No. 83:37487, 1974.

BENZYLATED PDE4 INHIBITORS

CROSS-REFERENCE TO RELATED APPLICATION

This application claims the benefit of U.S. Provisional Patent Application No. 60/190,337 filed Mar. 16, 2000, where this provisional application is incorporated herein by reference in its entirety.

TECHNICAL FIELD

The present invention is directed to a method for reducing the emetogenic effects of PDE inhibitors, and more particularly is directed to compounds having PDE4 inhibition activity with little or no emetogenic side-effects, and chemical methods including benzylation for preparing such compounds.

BACKGROUND OF THE INVENTION

Enzymes known as phosphodiesterases (PDEs) function in vivo to hydrolytically cleave the 3'-phosphodiester bond of cyclic nucleotides to thereby form the corresponding 5'-monophosphate. For instance, certain PDEs can hydroylze the 3'-phosphodiester bond of adenosine 3',5'-cyclic monophosphate (cAMP) so as to form 5'-adenosine monophosphate (5'-AMP), and/or can hydrolyze the 3'-phosphodiester bond of guanosine 3',5'-cyclic monophosphate (cGMP) so as to form 5'-guanosine monophosphate (5'-GMP). These cyclic nucleotides exert a significant impact on cellular processes by, for example, converting inactive protein kinase enzymes into an active form. The active form of the protein kinase catalyzes various phosphorylation processes that impact on fundamental cellular processes including transcriptional regulation, ion channel function, and signaling protein activity.

Researchers investigating PDEs generally agree that there are at least eleven distinct PDE families, differentiated on the basis of amino acid sequence, substrate specificity and sensitivity to endogenous and exogenous regulators. These families are commonly known as PDE1 through PDE11. In addition, researchers found that cyclic nucleotide concentration is a significant factor in the course of the in vivo inflammatory response. Accordingly, much research has been directed to methods for influencing the concentration of cyclic nucleotides as a means to influence the inflammatory response, and particular attention has been directed at PDE4 activity. One promising area of research is the development of small organic molecules that inhibit PDE activity. By inhibiting PDE activity, these small molecules reduce the amount of cyclic nucleotide that is converted into the (inactive) corresponding 5'-monophosphate, thereby elevating cyclic nucleotide concentration, and indirectly increasing protein kinase activity within the cell.

Many major pharmaceutical companies are working to develop specific small organic molecules into pharmaceutical compositions that function as PDE inhibitors. ROLIPRAM™ (Schering AG) is an example of an early attempt to develop such a composition directed to PDE4. However, while ROLIPRAM™ exhibited marked anti-inflammatory activity, it was also found to demonstrate unwanted side effects including emesis (also known as nausea and vomiting) and potentiation of gastric acid secretion. These undesired side effects caused ROLIPRAM™ to be withdrawn from development as an anti-inflammatory pharmaceutical. An understanding of the cause of these side-effects, and approaches to mitigate them, subsequently became topics of intense study.

It is now recognized that PDE4 exists in two distinct forms, i.e., two conformers. One conformer, known variously as HPDE4 or HARB, is particularly prevalent in the gastrointestinal tract and central nervous system, has a high affinity for ROLIPRAM™ (i.e., has a High Affinity ROLIPRAM™ Binding Site, "HARBS"), and is considered responsible for the unwanted side-effects. The other conformer is known variously as LPDE4 or LARB, is found in immunocompetent cells, and has a low affinity for ROLIPRAM™. Researchers are seeking to develop small molecules that inhibit the catalytic activity of LPDE4 rather than bind to HPDE4, i.e., molecules that have a low LPDE4:HPDE4 ratio where the numerator and denominator are the appropriate $IC_{50}$ values. In other words, researchers are seeking so-called "second generation" inhibitor molecules that interact with the LPDE4 catalytic site of PDE4, rather than the HPDE4 ROLIPRAM™ binding site, to provide desirable anti-inflammatory effect without unwanted side-effects such as emesis.

The present invention is directed to fulfilling this need in the art, and providing further related advantages as set forth more completely herein.

For additional and more detailed discussion of PDE enzymes, including the history of their discovery, their characterization and classification, their in vivo activity, their inhibition by small organic molecules, and current clinical efforts directed to providing pharmaceutical compositions containing these small molecules, see, e.g., Burnouf, C. et al. "Phosphodiesterase 4 Inhibitors" *Annual Reports in Medicinal Chemistry*, Vol. 33, Chap. 10, pp 91–109, 1998 (Bristol, J. A., ed.); Essayan, D. M. "Cyclic Nucleotide Phosphodiesterase (PDE) Inhibitors and Immunomodulation" *Biochemical Pharmacology* 57:965–973, 1999; Souness, J. E. and Foster, M. "Potential of phospodiesterase type IV inhibitors in the treatment of rheumatoid arthritis" *Idrugs* 1(5):541–553, 1998; Souness, J. E. et al. "Immunosuppressive and anti-inflammatory effect of cAMP phosphodiesterase (PDE) type 4 inhibitors" *Immunopharmacology* 47: 127–162, 2000; and Torphy, T. J. "Phosphodiesterase Isozymes" *Am. J. Respir. Crit. Care Med.* 157:351–370, 1998, as well as the numerous references cited in these articles.

SUMMARY OF THE INVENTION

In one aspect, the present invention provides a method for improving the therapeutic ratio of PDE4 inhibitors through reduction or elimination of emetogenic properties while allowing retention of PDE activity. In one aspect, the method comprises benzylation of a PDE4 inhibitor, wherein the benzylation places a benzyl group on a carbon atom of a PDE4 inhibitor, to provide a benzylated PDE4 inhibitor. In one aspect, the PDE4 inhibitor is ROLIPRAM™, while in another aspect the PDE4 inhibitor is ARIFLO™. The benzylation may replace an extractable hydrogen of the PDE4 inhibitor with a benzyl group. For instance, the PDE4 inhibitor may be reacted with a base in order to extract the extractable hydrogen, followed by reaction with a benzylating agent. In one aspect, the PDE4 inhibitor has a carbonyl group and the extractable hydrogen is located alpha to (i.e., next to) the carbonyl group. In another aspect, the PDE4 inhibitor has a carbonyl group and benzyl group is located beta to (i.e., with one intervening atom between) the carbonyl group. In another aspect, the PDE4 inhibitor has a carbonyl group and benzyl group is located gamma to (i.e., with two intervening atoms between) the carbonyl group. The extractable hydrogen may be removed under chemical conditions and replaced with a benzyl group.

In one aspect, the benzylated PDE4 inhibitor comprises at least one benzyl group (Bzl) of the formula

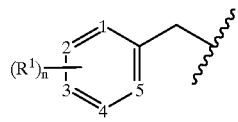

wherein each of the numerals 1, 2, 3, 4 and 5 may be carbon or nitrogen, with the proviso that the ring is aromatic and contains at least 3 carbon atoms;

n is 5 and $R^1$ at each occurrence is independently selected from halogen, nitro, $R^2$, $NR^2_{(m)}$, and $OR^2$ wherein m=0, 1, 2, or 3 and $R^2$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxyl, alkylcarboxylate, carboxylate, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^2$ group may be optionally substituted with one or more fluorine atoms, hydroxyl or $C_1$–$C_8$alkoxy; and the aryl portion of an $R^2$ group may be optionally substituted with $C_1$–$C_8$alkyl, $C_1$–$C_8$alkoxy or halogen.

In another aspect, the benzylated PDE4 inhibitor comprises at least one benzyl group (Bzl) of the formula

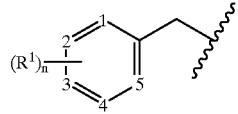

wherein each of the numerals 1, 2, 3, 4 and 5 may be carbon or nitrogen, with the proviso that the ring is aromatic and contains at least 4 carbon atoms;

n is 5 and $R^1$ at each occurrence is independently selected from halogen, nitro, $R^2$, and $OR^2$ wherein and $R^2$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, phenyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^2$ group may be optionally substituted with one or more fluorine atoms, hydroxyl or $C_1$–$C_8$alkoxy; and the phenyl portion of an $R^2$ group may be optionally substituted with $C_1$–$C_8$alkyl, $C_1$–$C_8$alkoxy or halogen.

In another aspect, the benzylated PDE4 inhibitor comprises at least one benzyl group (Bzl) of the formula

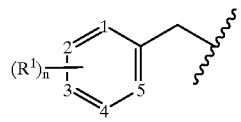

wherein each of the numerals 1, 2, 3, 4 and 5 may be carbon or nitrogen, with the proviso that the ring is aromatic and contains at least 3 carbon atoms;

n is 5 and $R^1$ at each occurrence is independently selected from halogen, nitro, $R^2$, $NR^2_{(m)}$, and $OR^2$ wherein m=0, 1, 2, or 3 and $R^2$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^2$ group may be optionally substituted with one or more fluorine atoms, hydroxyl or $C_1$–$C_8$alkoxy; and the aryl portion of an $R^2$ group may be optionally substituted with $C_1$–$C_8$alkyl, $C_1$–$C_8$alkoxy or halogen; with the proviso that either (a) at least one $R^1$ is $OR^2$, or (b) the benzyl ring contains at least two $R^1$ groups that are not hydrogen.

In another aspect, the benzylated PDE4 inhibitor comprises at least one benzyl group (Bzl) of the formula

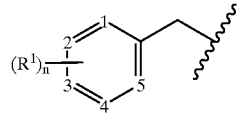

wherein each of the numerals 1, 2, 3, 4 and 5 is carbon;

n is 5 and $R^1$ at each occurrence is independently selected from halogen, nitro, $R^2$, $NR^2_{(m)}$, and $OR^2$ wherein m=0, 1, 2, or 3 and $R^2$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^2$ group may be optionally substituted with one or more fluorine atoms, hydroxyl or $C_1$–$C_8$alkoxy; and the aryl portion of an $R^2$ group may be optionally substituted with $C_1$–$C_8$alkyl, $C_1$–$C_8$alkoxy or halogen; with the proviso that $R_1$ is hydrogen at either 1, 2, or 3 occurrences of n, but not 4 or 5 occurrences.

In one aspect of the present invention, the benzylated PDE4 inhibitor comprises a benzyl group, and independently of the benzyl group the benzylated PDE4 inhibitor further comprises a phenyl group of the formula

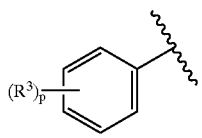

wherein p is 5; and $R^3$ at each occurrence is independently selected from halogen, nitro, $R^4$, $NR^2_{(q)}$, and $OR^4$ wherein q=0, 1, 2, or 3 and $R^4$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^4$ group may be optionally substituted with one or more fluorine atoms, hydroxyl or $C_1$–$C_8$alkoxy; and the aryl portion of an $R^4$ group may be optionally substituted with $C_1$–$C_8$alkyl, $C_1$–$C_8$alkoxy or halogen. In one aspect of the invention $R^3$ is $OR^4$ in at least one occurrence wherein $R^4$ is selected from $C_1$–$C_8$alkyl, $C_3$–$C_7$cycloalkyl, and $C_6$–$C_9$polycycloalkyl.

In one aspect of the present invention, the phenyl group has the formula

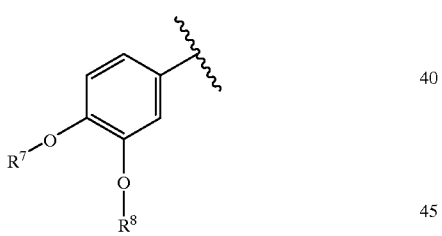

wherein $R^7$ is selected from methyl, ethyl, difluoromethyl and trifluoromethyl; and $R^8$ is selected from $C_3$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^2$ group may be optionally substituted with one or more fluorine atoms, hydroxyl or $C_1$–$C_4$alkoxy; and the aryl portion (e.g., phenyl) of an $R^2$ group may be optionally substituted with $C_1$–$C_4$alkyl, $C_1$–$C_4$alkoxy or halogen. Optionally, $R^8$ is not cyclopentyl.

Thus, in one aspect, the present invention provides a method for improving the therapeutic ratio of PDE4 inhibitors through reduction or elimination of emetogenic properties while allowing retention of PDE activity, the method comprising benzylation of a PDE4 inhibitor, wherein the benzylation places a benzyl group on a carbon atom of a PDE4 inhibitor, to provide a benzylated PDE4 inhibitor.

In one aspect, the PDE4 inhibitor is ROLIPRAM™ or an analog thereof. For instance, the C-benzylated ROLIPRAM™ or analog thereof may have the formula:

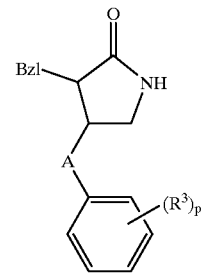

and isolated stereoisomers, salts and solvates thereof, wherein Bzl is a benzyl group; A is selected from a direct bond, optionally substituted $C_1$–$C_5$alkylene, optionally substituted $C_2$–$C_5$alkenyl and optionally substituted phenylene; p is 5; and $R^3$ at each occurrence is independently selected from halogen, nitro, $R^4$, $NR^4_{(q)}$, and $OR^4$ wherein q=0, 1, 2, or 3 and $R^4$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^4$ group may be optionally substituted with one or more fluorine atoms, hydroxyl or $C_1$–$C_8$alkoxy; and the aryl portion of an $R^4$ group may be optionally substituted with $C_1$–$C_8$alkyl, $C_1$–$C_8$alkoxy or halogen. Optionally, A is a direct bond; and in at least one occurrence, $R^3$ is $OR^4$ wherein $R^4$ is selected from $C_1$–$C_8$alkyl, $C_3$–$C_7$cycloalkyl, and $C_6$–$C_9$polycycloalkyl.

For instance, the benzylated ROLIPRAM™ or analog thereof may have the formula:

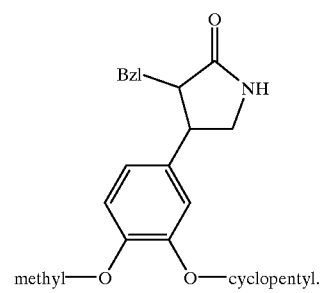

In another aspect the PDE4 inhibitor is ARIFLO™ or an analog thereof. For instance, the C-benzylated ARIFLO™ or analog thereof may have the formula

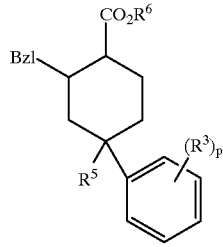

and isolated stereoisomers, salts and solvates thereof, wherein Bzl is a benzyl group; p is 5; and $R^3$ at each occurrence is independently selected from halogen, nitro, $R^4$, $NR^2_{(q)}$, and $OR^4$ wherein q=0, 1, 2, or 3 and $R^4$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^4$ group may be optionally substituted with one or more fluorine atoms, hydroxyl or $C_1$–$C_8$alkoxy; and the aryl portion of an $R^4$ group may be optionally substituted with $C_1$–$C_8$alkyl, $C_1$–$C_8$alkoxy or halogen; $R^5$ is selected from H, halogen, cyano, $C_1$–$C_8$alkyl, and $C_1$–$C_8$alkoxy; and $R^6$ is selected from H, positively charged species, and $C_1$–$C_8$alkyl. Optionally, in at least one occurrence, $R^3$ is $OR^4$ wherein $R^4$ is selected from $C_1$–$C_8$alkyl, $C_3$–$C_7$cycloalkyl, and $C_5$–$C_9$bicycloalkyl; and $R^6$ is selected from H and positively charged species. For instance, the benzylated ARIFLO™ or analog thereof may have the formula

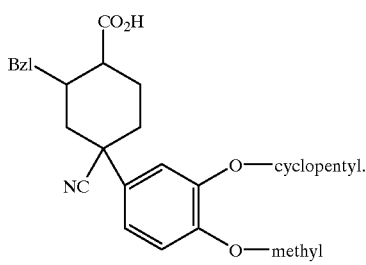

As another example, the benzylated ARIFLO™ or analog thereof may have the formula

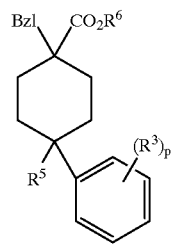

and isolated stereoisomers, salts and solvates thereof, wherein Bzl is a benzyl group; p is 5; and $R^3$ at each occurrence is independently selected from halogen, nitro, $R^4$, $NR^2_{(q)}$, and $OR^4$ wherein q=0, 1, 2, or 3 and $R^4$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^4$ group may be optionally substituted with one or more fluorine atoms, hydroxyl or $C_1$–$C_8$alkoxy; and the aryl portion of an $R^4$ group may be optionally substituted with $C_1$–$C_8$alkyl, $C_1$–$C_8$alkoxy or halogen; $R^5$ is selected from H, halogen, cyano, $C_1$–$C_8$alkyl, and $C_1$–$C_8$alkoxy; and $R^6$ is selected from H, positively charged species, and $C_1$–$C_8$alkyl. Optionally, in at least one occurrence, $R^3$ is $OR^4$ wherein $R^4$ is selected from $C_1$–$C_8$alkyl, $C_3$–$C_7$cycloalkyl, and $C_5$–$C_9$bicycloalkyl; and $R^6$ is selected from H and positively charged species. For instance, the benzylated ARIFLO™ or analog thereof may have the formula

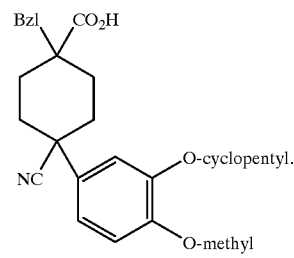

In another aspect, the present invention provides a method for improving the therapeutic ratio of PDE4 inhibitors through reduction or elimination of emetogenic properties while allowing retention of PDE activity, where the method comprises benzylation of a PDE4 inhibitor, wherein the benzylation places a benzyl group (Bzl) on a nitrogen atom of a PDE4 inhibitor, to provide an N-benzylated PDE4 inhibitor, wherein the N-benzylated PDE4 inhibitor comprises at least one benzyl group (Bzl) of the formula

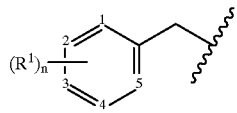

wherein each of the numerals 1, 2, 3, 4 and 5 may be carbon or nitrogen, with the proviso that the ring is aromatic and contains at least 3 carbon atoms; n is 5 and $R^1$ at each occurrence is independently selected from halogen, nitro, $R^2$, $NR^2_{(m)}$, and $OR^2$ wherein m=0, 1, 2, or 3 and $R^2$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^2$ group may be optionally substituted with one or more fluorine atoms, hydroxyl or $C_1$–$C_8$alkoxy; and the aryl portion of an $R^2$ group may be optionally substituted with $C_1$–$C_8$alkyl, $C_1$–$C_8$alkoxy or halogen.

In one embodiment, either (a) at least one $R^1$ is $OR^2$, or (b) the benzyl ring contains at least two $R^1$ groups that are not hydrogen. In another embodiment, each of the numerals 1, 2, 3, 4 and 5 is carbon. In another embodiment, n is 5 and $R^1$ at each occurrence is independently selected from halogen, nitro, $R^2$, $NR^2_{(m)}$, and $OR^2$ wherein m=0, 1, 2, or 3 and $R^2$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, phenyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^2$ group may be optionally substituted with one or more fluorine atoms, hydroxyl or $C_1$–$C_8$alkoxy; and the phenyl portion of an $R^2$ group may be optionally substituted with $C_1$–$C_8$alkyl, $C_1$–$C_8$alkoxy or halogen. In a preferred embodiment, each of the numerals 1, 2, 3, 4 and 5 may be carbon or nitrogen, with the proviso that the ring is aromatic and contains at least 3 carbon atoms; n is 5 and $R^1$ at each occurrence is independently selected from halogen and $OR^2$ wherein $R^2$ at each occurrence is independently selected from H and $C_1$–$C_8$alkyl; with the provisos that the benzyl ring contain no more than three hydrogen substituents and no more than one methoxy substituent.

The N-benzylation method may be applied to a PDE4 inhibitor containing a nitrogen atom, preferably an amide group where the nitrogen atom of the amide group undergoes a benzylation reaction to place a benzyl group on that nitrogen atom. Suitable PDE4 inhibitors for the N-benzylation reaction of the present invention include, without limitation, ROLIPRAM™, WAY-PDA-641, Ro-20-1724, RP 73401, CP-80,633-A, AROFYLLINE™ and CIPAMFYLLINE™. The benzylation may replace an extractable hydrogen of the PDE4 inhibitor with a benzyl group. For instance, the PDE4 inhibitor may be reacted with a base in order to extract the extractable hydrogen, followed by reaction with a benzylating agent. In one aspect, the PDE4 inhibitor has an amide group and the extractable hydrogen is located on the nitrogen atom of the amide group.

In one aspect, the N-benzylated ROLIPRAM™ or analog thereof prepared by the benzylation method of the present invention has the formula:

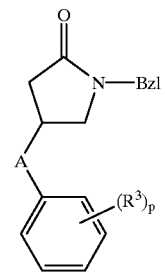

and isolated stereoisomers, salts and solvates thereof, wherein Bzl is a benzyl group; A is selected from a direct bond, optionally substituted $C_1$–$C_5$alkylene, optionally substituted $C_2$–$C_5$alkenyl and optionally substituted phenylene; p is 5 and $R^3$ at each occurrence is independently selected from halogen, nitro, $R^4$, $NR^4_{(q)}$, and $OR^4$ wherein q=0, 1, 2, or 3 and $R^4$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^4$ group may be optionally substituted with one or more fluorine atoms, hydroxyl or $C_1$–$C_8$alkoxy; and the aryl portion of an $R^4$ group may be optionally substituted with $C_1$–$C_8$alkyl, $C_1$–$C_8$alkoxy or halogen. Optionally, A is a direct bond; p is 1, 2, or 3; and in at least one occurrence, $R^3$ is $OR^4$ wherein $R^4$ is selected from $C_1$–$C_8$alkyl, $C_3$–$C_7$cycloalkyl, and $C_6$–$C_9$polycycloalkyl. For instance, the benzylated ROLIPRAM™ or analog thereof may have the formula

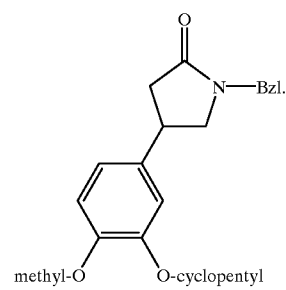

methyl-O    O-cyclopentyl

In another aspect of the inventive method for N-benzylation, the PDE4 inhibitor is WAY-PDA-641 or an analog thereof. For instance, the benzylated WAY-PDA-641 or analog thereof may have the formula:

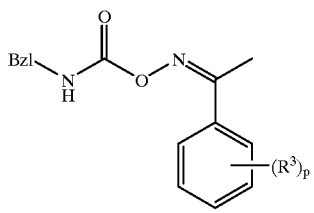

and isolated stereoisomers, salts and solvates thereof, wherein Bzl is a benzyl group; p is 5 and $R^3$ at each occurrence is independently selected from halogen, nitro, $R^4$, $NR^4_{(q)}$, and $OR^4$ wherein q=0, 1, 2, or 3 and $R^4$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^4$ group may be optionally substituted with one or more fluorine atoms, hydroxyl or $C_1$–$C_8$alkoxy; and the aryl portion of an $R^4$ group may be optionally substituted with $C_1$–$C_8$alkyl, $C_1$–$C_8$alkoxy or halogen. Optionally, p is 1, 2, or 3; and in at least one occurrence, $R^3$ is $OR^4$ wherein $R^4$ is selected from $C_1$–$C_8$alkyl, $C_3$–$C_7$cycloalkyl, and $C_6$–$C_9$polycycloalkyl. For instance, the benzylated WAY-PDA-641 or analog thereof may have the formula:

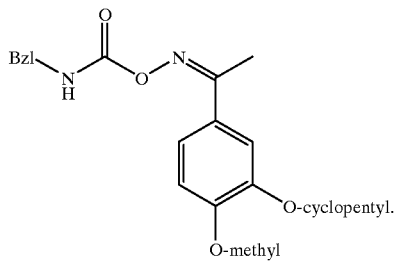

In another aspect of the inventive method for N-benzylation of a PDE4 inhibitor, the PDE4 inhibitor is Ro-20-1724 or an analog thereof. In one aspect, the benzylated Ro-20-1724 or analog thereof may have the formula:

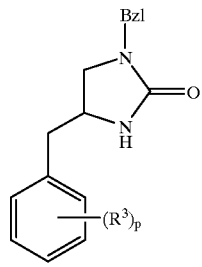

and isolated stereoisomers, salts and solvates thereof, wherein Bzl is a benzyl group; p is 5 and $R^3$ at each occurrence is independently selected from halogen, nitro, $R^4$, $NR^2_{(q)}$, and $OR^4$ wherein q=0, 1, 2, or 3 and $R^4$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^4$ group may be optionally substituted with one or more fluorine atoms, hydroxyl or $C_1$–$C_8$alkoxy; and the aryl portion of an $R^4$ group may be optionally substituted with $C_1$–$C_8$alkyl, $C_1$–$C_8$alkoxy or halogen. Optionally, p is 1, 2, or 3; and in at least one occurrence, $R^3$ is $OR^4$ wherein $R^4$ is selected from $C_1$–$C_8$alkyl, $C_3$–$C_7$cycloalkyl, and $C_6$–$C_9$polycycloalkyl. For instance, the N-benzylated Ro-20-1724 or analog thereof may have the formula:

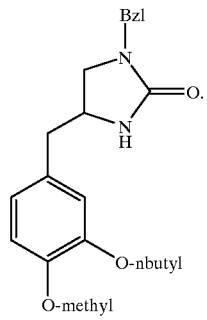

In another aspect, the N-benzylated Ro-20-1724 or analog thereof has the formula:

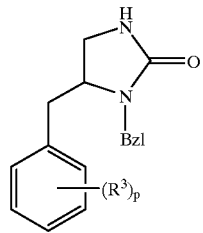

and isolated stereoisomers, salts and solvates thereof, wherein Bzl is a benzyl group; p is 5 and $R^3$ at each occurrence is independently selected from halogen, nitro, $R^4$, $NR^2_{(q)}$, and $OR^4$ wherein q=0, 1, 2, or 3 and $R^4$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^4$ group may be optionally substituted with one or more fluorine atoms, hydroxyl or $C_1$–$C_8$alkoxy; and the aryl portion of an $R^4$ group may be optionally substituted with $C_1$–$C_8$alkyl, $C_1$–$C_8$alkoxy or halogen. Optionally, p is 1, 2, or 3; and in at least one occurrence, $R^3$ is $OR^4$ wherein $R^4$ is selected from $C_1$–$C_8$alkyl, $C_3$–$C_7$cycloalkyl, and $C_6$–$C_9$polycycloalkyl. For instance, the benzylated Ro-20-1724 or analog thereof may have the formula:

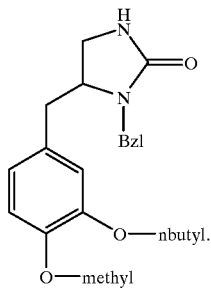

In another aspect, the N-benzylation reaction of the present invention employs RP 73401 or an analog thereof as the PDE4 inhibitor. For example, the benzylated RP 73401 or analog thereof may have the formula:

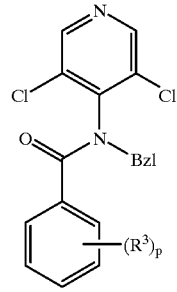

and isolated stereoisomers, salts and solvates thereof, wherein Bzl is a benzyl group; p is 5 and $R^3$ at each occurrence is independently selected from halogen, nitro, $R^4$, $NR^2_{(q)}$, and $OR^4$ wherein q=0, 1, 2, or 3 and $R^4$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^4$ group may be optionally substituted with one or more fluorine atoms, hydroxyl or $C_1$–$C_8$alkoxy; and the aryl portion of an $R^4$ group may be optionally substituted with $C_1$–$C_8$alkyl, $C_1$–$C_8$alkoxy or halogen. Optionally, p is 1, 2, or 3; and in at least one occurrence, $R^3$ is $OR^4$ wherein $R^4$ is selected from $C_1$–C8alkyl, $C_3$–$C_7$cycloalkyl, and $C_6$–$C_9$polycycloalkyl. For instance, the benzylated RP 73401 or analog thereof may have the formula:

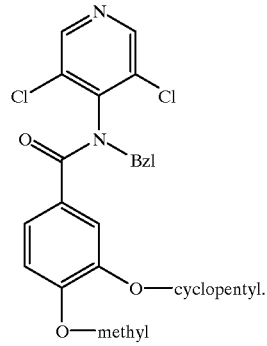

In another aspect of the inventive method for N-benzylation of a PDE4 inhibitor, the PDE4 inhibitor is CP-80,633-A or an analog thereof. For example, the benzylated CP-80,633-A or analog thereof may have the formula:

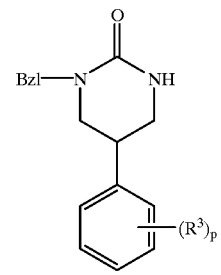

and isolated stereoisomers, salts and solvates thereof, wherein Bzl is a benzyl group; p is 5 and $R^3$ at each occurrence is independently selected from halogen, nitro, $R^4$, $NR^2_{(q)}$, and $OR^4$ wherein q=0, 1, 2, or 3 and $R^4$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^4$ group may be optionally substituted with one or more fluorine atoms, hydroxyl or $C_1$–$C_8$alkoxy; and the aryl portion of an $R^4$ group may be optionally substituted with $C_1$–$C_8$alkyl, $C_1$–$C_8$alkoxy or halogen. Optionally, p is 1, 2, or 3; and in at least one occurrence, $R^3$ is $OR^4$ wherein $R^4$ is selected from $C_1$–$C_8$alkyl, $C_3$–$C_7$cycloalkyl, and $C_6$–$C_9$polycycloalkyl. For instance, the benzylated CP-80,633-A or analog thereof may have the formula:

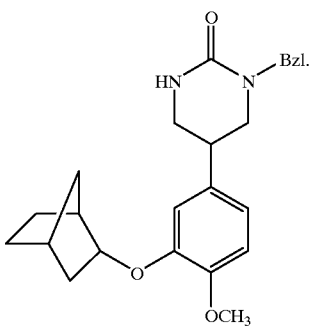

In another aspect of the inventive method for N-benzylation of a PDE4 inhibitor, the PDE4 inhibitor is AROFYLLINE™ or an analog thereof. For example, the benzylated AROFYLLINE™ or analog thereof may have the formulae:

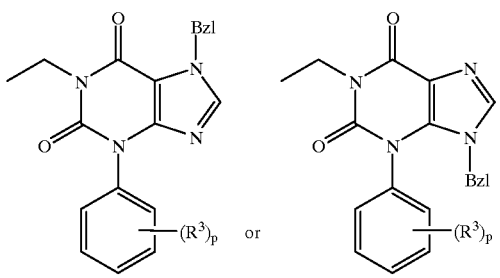

and isolated stereoisomers, salts and solvates thereof, wherein Bzl is a benzyl group; p is 5 and $R^3$ at each occurrence is independently selected from halogen, nitro, $R^4$, $NR^2_{(q)}$, and $OR^4$ wherein q=0, 1, 2, or 3 and $R^4$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^4$ group may be optionally substituted with one or more fluorine atoms, hydroxyl or $C_1$–$C_8$alkoxy; and the aryl portion of an $R^4$ group may be optionally substituted with $C_1$–$C_8$alkyl, $C_1$–$C_8$alkoxy or halogen. Optionally, p is 1, 2 or 3; and in at least one occurrence, $R^3$ is halogen or $OR^4$ wherein $R^4$ is selected from $C_1$–$C_8$alkyl, $C_3$–$C_7$cycloalkyl, and $C_6$–$C_9$polycycloalkyl. For example, the benzylated AROFYLLINE™ or analog thereof may have the formula

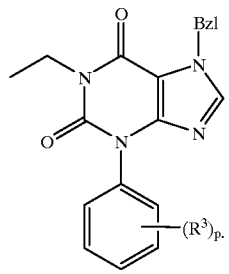

As another example the benzylated AROFYLLINE™ or analog thereof may have the formula

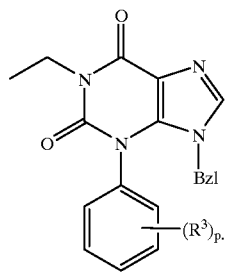

More specific examples of benzylated AROFYLLINE™ or analog thereof compounds prepared by the present invention have the formula:

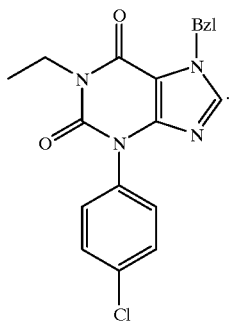

As another specific example the benzylated AROFYLLINE™ or analog thereof may have the formula:

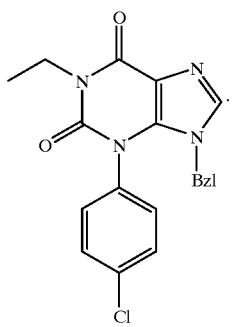

In another aspect of the inventive method for N-benzylation of a PDE4 inhibitor, the PDE4 inhibitor is CIPAMFYLLINE™ or an analog thereof. For example, the benzylated CIPAMFYLLINE™ or analog thereof may have the formulae:

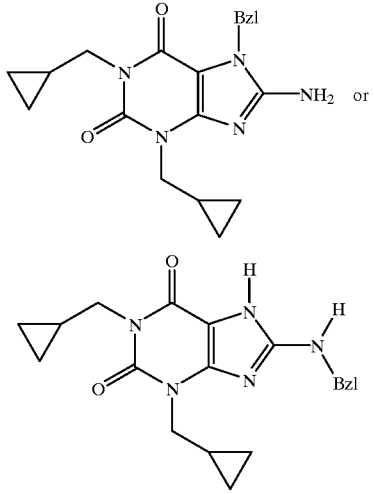

and isolated stereoisomers, salts and solvates thereof, wherein Bzl is a benzyl group.

In addition the above methods for improving the therapeutic ratio of PDE4 inhibitors through reduction or elimination of emetogenic properties while allowing retention of PDE activity, the present invention provides PDE4 inhibitors having benzyl groups.

In one aspect, the present invention provides a C-benzylated ROLIPRAM™ or analog thereof compound of the formula

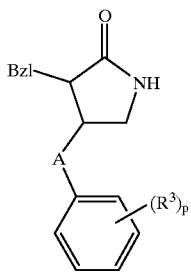

and isolated stereoisomers, salts and solvates thereof, wherein Bzl is a benzyl group of the formula

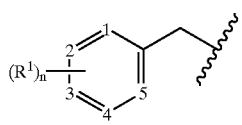

wherein each of the numerals 1, 2, 3, 4 and 5 may be carbon or nitrogen, with the proviso that the ring is aromatic and contains at least 3 carbon atoms; n is 5 and $R^1$ at each occurrence is independently selected from halogen, nitro, $R^2$, $NR^2_{(m)}$, and $OR^2$ wherein m=0, 1, 2, or 3 and $R^2$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^2$ group may be optionally substituted with one or more fluorine atoms, hydroxyl or $C_1$–$C_8$alkoxy; and the aryl portion of an $R^2$ group may be optionally substituted with $C_1$–$C_8$alkyl, $C_1$–$C_8$alkoxy or halogen; A is selected from a direct bond, optionally substituted $C_1$–$C_5$alkylene, optionally substituted $C_2$–$C_5$alkenyl and optionally substituted phenylene; p is 5 and $R^3$ at each occurrence is independently selected from halogen, nitro, $R^4$, $NR^2_{(q)}$, and $OR^4$ wherein q=0, 1, 2, or 3 and $R^4$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^4$ group may be optionally substituted with one or more fluorine atoms, hydroxyl or $C_1$–$C_8$alkoxy; and the aryl portion of an $R^4$ group may be optionally substituted with $C_1$–$C_8$alkyl, $C_1$–$C_8$alkoxy or halogen. Optionally, A is selected from a direct bond, $C_1$–$C_5$alkylene, $C_2$–$C_5$alkenyl and phenylene. Optionally, A is a direct bond; and in at least one occurrence, $R^3$ is $OR^1$ wherein $R^2$ is selected from $C_1$–$C_8$alkyl, $C_3$–$C_7$cycloalkyl, and $C_6$–$C_9$polycycloalkyl. In a preferred embodiment, $R^3$ at the para position relative to A is alkoxy, and $R^3$ at one meta position is selected from alkyl having at least 3 carbons and alkoxy having at least 3 carbons.

For example, the present invention provides a compound having the formula

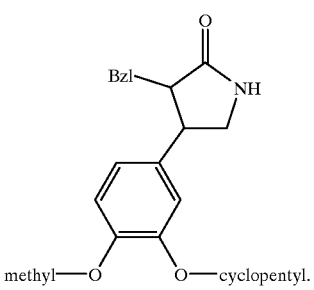

In another aspect the present invention provides an N-benzylated ROLIPRAM™ or analog thereof compound of the formula

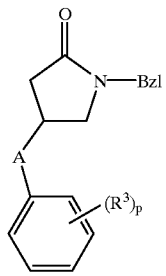

and isolated stereoisomers, salts and solvates thereof, wherein Bzl is a benzyl group of the formula

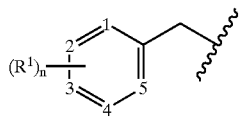

wherein each of the numerals 1, 2, 3, 4 and 5 may be carbon or nitrogen, with the proviso that the ring is aromatic and contains at least 3 carbon atoms; n is 5 and $R^1$ at each occurrence is independently selected from halogen, nitro, $R^2$, $NR^2{}_{(m)}$, and $OR^2$ wherein m=0, 1, 2, or 3 and $R^2$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^2$ group may be optionally substituted with one or more fluorine atoms, hydroxyl or $C_1$–$C_8$alkoxy; and the aryl portion of an $R^2$ group may be optionally substituted with $C_1$–$C_8$alkyl, $C_1$–$C_8$alkoxy or halogen; A is selected from a direct bond, optionally substituted $C_1$–$C_5$alkylene, optionally substituted $C_2$–$C_5$alkenyl and optionally substituted phenylene; p is 5 and $R^3$ at each occurrence is independently selected from halogen, nitro, $R^4$, $NR^2{}_{(q)}$, and $OR^4$ wherein q=0, 1, 2, or 3 and $R^4$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, C6–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^4$ group may be optionally substituted with one or more fluorine atoms, hydroxyl or $C_1$–$C_8$alkoxy; and the aryl portion of an $R^4$ group may be optionally substituted with $C_1$–$C_8$alkyl, $C_1$–$C_8$alkoxy or halogen. Optionally, A is a direct bond; and in at least one occurrence, $R^3$ is $OR^4$ wherein $R^4$ is selected from $C_1$–$C_8$alkyl, $C_3$–$C_7$cycloalkyl, and $C_6$–$C_9$polycycloalkyl. In another optional embodiment at least one $R^1$ is $OR^2$. In a preferred embodiment, at the meta position relative to the A group on the $R^3$-substituted phenyl ring, $R^3$ is alkoxy having at least three carbon atoms, excluding cyclopentyloxy, and at the para position $R^1$ is not hydrogen. In one embodiment, A is selected from a direct bond, $C_1$–$C_5$alkylene, $C_2$–$C_5$alkenyl and phenylene.

In another aspect the present invention provides an N-benzylated ROLIPRAM™ or analog thereof compound of the formula

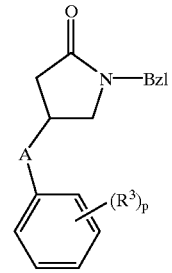

and isolated stereoisomers, salts and solvates thereof, wherein Bzl is a benzyl group of the formula

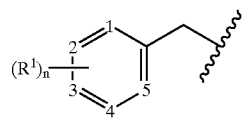

wherein each of the numerals 1, 2, 3, 4 and 5 may be carbon or nitrogen, with the proviso that the ring is aromatic and contains at least 3 carbon atoms; n is 5 and $R^1$ at each occurrence is independently selected from halogen and $OR^2$ wherein $R^2$ at each occurrence is independently selected from H and $C_1$–$C_8$alkyl; with the provisos that the benzyl ring contain no more than three hydrogen substituents and no more than one methoxy substituent; A is selected from a direct bond, optionally substituted C1-C5alkylene, optionally substituted $C_2$–$C_5$alkenyl and optionally substituted phenylene; p is 5 and $R^3$ at each occurrence is independently selected from halogen, nitro, $R^4$, $NR^2{}_{(q)}$, and $OR^4$ wherein q=0, 1, 2, or 3 and $R^4$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^4$ group may be optionally substituted with one or more fluorine atoms, hydroxyl or $C_1$–$C_8$alkoxy; and the aryl portion of an $R^4$ group may be optionally substituted with $C_1$–$C_8$alkyl, $C_1$–$C_8$alkoxy or halogen. Optionally, A is a direct bond; and in at least one occurrence, $R^3$ is $OR^4$ wherein $R^4$ is selected from $C_1$–$C_8$alkyl, $C_3$–$C_7$cycloalkyl, and $C_6$–$C_9$polycycloalkyl. In another optional embodiment at least one $R^1$ is $OR^2$. In a preferred embodiment, at the meta position relative to the A group on the $R^3$-substituted phenyl ring, $R^3$ is alkoxy having at least three carbon atoms, excluding cyclopentyloxy, and at the para position $R^1$ is not hydrogen. In one embodiment, A is selected from a direct bond, $C_1$–$C_5$alkylene, $C_2$–$C_5$alkenyl and phenylene.

For instance, the present invention provides a compound having the formula

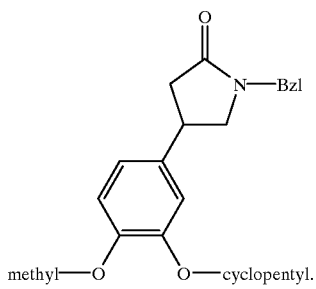

In another aspect the present invention provides a benzylated ARIFLO™ or analog thereof compound of the formulae

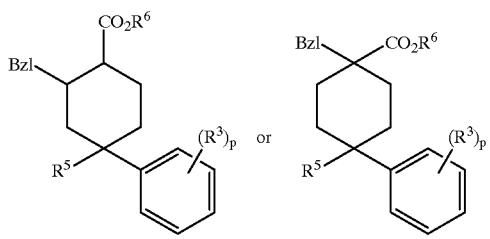

and isolated stereoisomers, salts and solvates thereof, wherein Bzl is a benzyl group of the formula

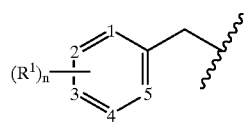

wherein each of the numerals 1, 2, 3, 4 and 5 may be carbon or nitrogen, with the proviso that the ring is aromatic and contains at least 3 carbon atoms; n is 5 and $R^1$ at each occurrence is independently selected from halogen, nitro, $R^2$, $NR^2_{(m)}$, and $OR^2$ wherein m=0, 1, 2, or 3 and $R^2$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^2$ group may be optionally substituted with one or more fluorine atoms, hydroxyl or $C_1$–$C_8$alkoxy; and the aryl portion of an $R^2$ group may be optionally substituted with $C_1$–$C_8$alkyl, $C_1$–$C_8$alkoxy or halogen; p is 5; and $R^3$ at each occurrence is independently selected from halogen, nitro, $R^4$, $NR^2_{(q)}$, and $OR^4$ wherein q=0, 1, 2, or 3 and $R^4$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^4$ group may be optionally substituted with one or more fluorine atoms, hydroxyl or $C_1$–$C_8$alkoxy; and the aryl portion of an $R^4$ group may be optionally substituted with $C_1$–$C_8$alkyl, $C_1$–$C_8$alkoxy or halogen; $R^5$ is selected from H, halogen, cyano, $C_1$–$C_8$alkyl, and $C_1$–$C_8$alkoxy; and $R^6$ is selected from H, positively charged species, and $C_1$–$C_8$alkyl. Optionally, in at least one occurrence, $R^3$ is $OR^4$ wherein $R^4$ is selected from $C_1$–$C_8$alkyl, $C_3$–$C_7$cycloalkyl, and $C_5$–$C_9$bicycloalkyl; and $R^6$ is selected from H and positively charged species.

For instance, the present invention provides compounds having the formulae

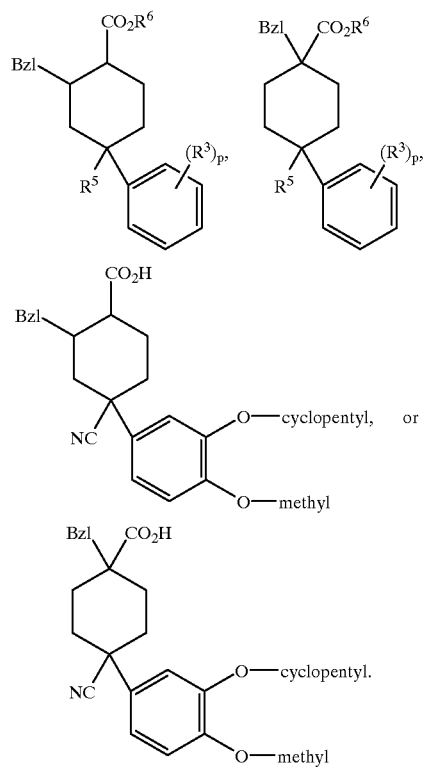

In another aspect the present invention provides a benzylated WAY-PDA-641 or analog thereof compound of the formula:

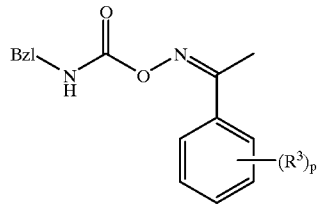

and isolated stereoisomers, salts and solvates thereof, wherein Bzl is a benzyl group of the formula

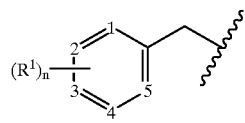

wherein each of the numerals 1, 2, 3, 4 and 5 may be carbon or nitrogen, with the proviso that the ring is aromatic and contains at least 3 carbon atoms; n is 5 and $R^1$ at each occurrence is independently selected from halogen, nitro, $R^2$, $NR^2_{(m)}$, and $OR^2$ wherein m=0, 1, 2, or 3 and $R^2$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^2$ group may be optionally substituted with one or more fluorine atoms, hydroxyl or $C_1$–$C_8$alkoxy; and the aryl portion of an $R^2$ group may be optionally substituted with $C_1$–$C_8$alkyl, $C_1$–$C_8$alkoxy or halogen; p is 5; and $R^3$ at each occurrence is independently selected from halogen, nitro, $R^4$, $NR^2_{(q)}$, and $OR^4$ wherein q=0, 1, 2, or 3 and $R^4$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^4$ group may be optionally substituted with one or more fluorine atoms, hydroxyl or $C_1$–$C_8$alkoxy; and the aryl portion of an $R^4$ group may be optionally substituted with $C_1$–$C_8$alkyl, $C_1$–$C_8$alkoxy or halogen. Optionally, in at least one occurrence, $R^3$ is $OR^4$ wherein $R^4$ is selected from $C_1$–$C_8$alkyl, $C_3$–$C_7$cycloalkyl, and $C_6$–$C_9$polycycloalkyl. For instance, the present invention provides compound having the formula:

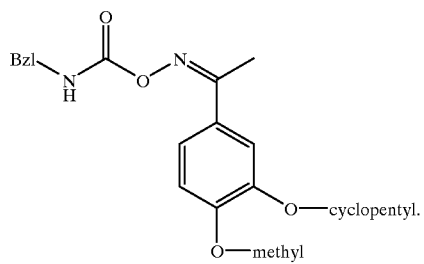

In another aspect the present invention provides a benzylated Ro-20-1724 or analog thereof compound of the formulae:

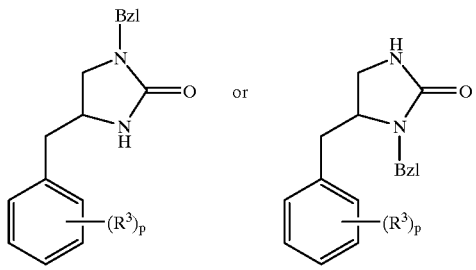

and isolated stereoisomers, salts and solvates thereof, wherein Bzl is a benzyl group of the formula

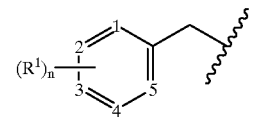

wherein each of the numerals 1, 2, 3, 4 and 5 may be carbon or nitrogen, with the proviso that the ring is aromatic and contains at least 3 carbon atoms; n is 5 and $R^1$ at each occurrence is independently selected from halogen, nitro, $R^2$, $NR^2_{(m)}$, and $OR^2$ wherein m=0, 1, 2, or 3 and $R^2$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^2$ group may be optionally substituted with one or more fluorine atoms, hydroxyl or $C_1$–$C_8$alkoxy; and the aryl portion of an $R^2$ group may be optionally substituted with $C_1$–$C_8$alkyl, $C_1$–$C_8$alkoxy or halogen; p is 5; and $R^3$ at each occurrence is independently selected from halogen, nitro, $R^4$, $NR^2_{(q)}$, and $OR^4$ wherein q=0, 1, 2, or 3 and $R^4$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^4$ group may be optionally substituted with one or more fluorine atoms, hydroxyl or $C_1$–$C_8$alkoxy; and the aryl portion of an $R^4$ group may be optionally substituted with $C_1$–$C_8$alkyl, $C_1$–$C_8$alkoxy or halogen. Optionally, in at least one occurrence, $R^3$ is $OR^4$ wherein $R^4$ is selected from $C_1$–$C_8$alkyl, $C_3$–$C_7$cycloalkyl, and $C_5$–$C_9$bicycloalkyl.

In a preferred embodiment, relative to the methylene bridge to the heterocyclic ring, $R^3$ at the para position is alkoxy, and $R^3$ at a meta position is alkoxy having at least three carbon atoms. For example, the present invention provides a compound having the formulae

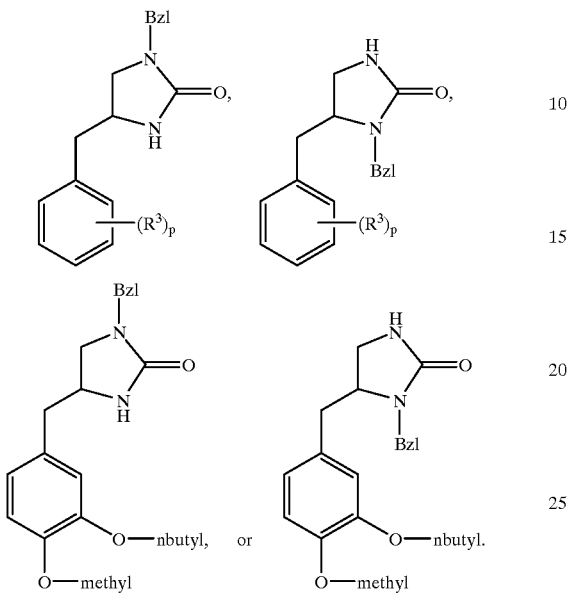

In another aspect the present invention provides a benzylated RP 73401 or analog thereof compound of the formula:

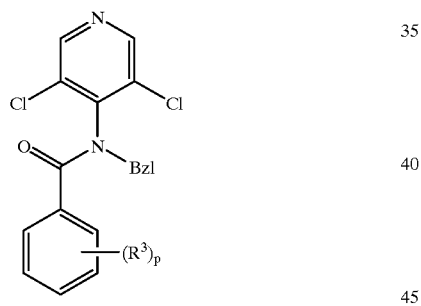

and isolated stereoisomers, salts and solvates thereof, wherein Bzl is a benzyl group of the formula

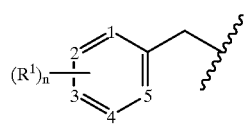

wherein each of the numerals 1, 2, 3, 4 and 5 may be carbon or nitrogen, with the proviso that the ring is aromatic and contains at least 3 carbon atoms; n is 5 and $R^1$ at each occurrence is independently selected from halogen, nitro, $R^2$, $NR^2_{(m)}$, and $OR^2$ wherein m=0, 1, 2, or 3 and $R^2$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^2$ group may be optionally substituted with one or more fluorine atoms, hydroxyl or $C_1$–$C_8$alkoxy; and the aryl portion of an $R^2$ group may be optionally substituted with $C_1$–$C_8$alkyl, $C_1$–$C_8$alkoxy or halogen; p is 5; and $R^3$ at each occurrence is independently selected from halogen, nitro, $R^4$, $NR^2_{(q)}$, and $OR^4$ wherein q=0, 1, 2, or 3 and $R^4$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^4$ group may be optionally substituted with one or more fluorine atoms, hydroxyl or $C_1$–$C_8$alkoxy; and the aryl portion of an $R^4$ group may be optionally substituted with $C_1$–$C_8$alkyl, $C_1$–$C_8$alkoxy or halogen. Optionally, in at least one occurrence, $R^3$ is $OR^4$ wherein $R^4$ is selected from $C_1$–$C_8$alkyl, $C_3$–$C_7$cycloalkyl, and $C_6$–$C_9$polycycloalkyl. For example, the present invention provides a compound having the formula:

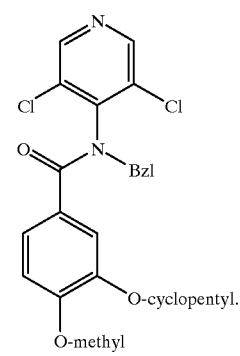

In another aspect the present invention provides a benzylated CP-80,633-A or analog thereof compound of the formula:

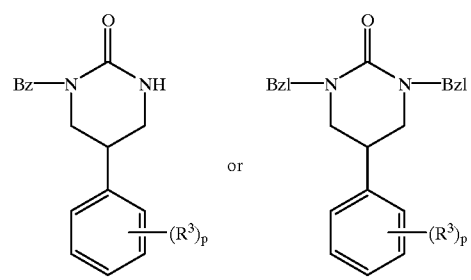

and isolated stereoisomers, salts and solvates thereof, wherein Bzl is a benzyl group of the formula

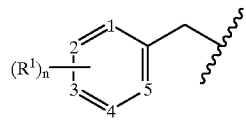

wherein each of the numerals 1, 2, 3, 4 and 5 may be carbon or nitrogen, with the proviso that the ring is aromatic and contains at least 3 carbon atoms; n is 5 and $R^1$ at each occurrence is independently selected from halogen, nitro, $R^2$, $NR^2_{(m)}$, and $OR^2$ wherein m=0, 1, 2, or 3 and $R^2$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^2$ group may be optionally substituted with one or more fluorine atoms, hydroxyl or $C_1$–$C_8$alkoxy; and the aryl portion of an $R^2$ group may be optionally substituted with $C_1$–$C_8$alkyl, $C_1$–$C_8$alkoxy or halogen; p is 5; and $R^3$ at each occurrence is independently selected from nitro, $R^4$, $NR^2_{(q)}$, and $OR^4$ wherein q=0, 1, 2, or 3 and $R^4$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^4$ group may be optionally substituted with one or more fluorine atoms, hydroxyl or $C_1$–$C_8$alkoxy; and the aryl portion of an $R^4$ group may be optionally substituted with $C_1$–$C_8$alkyl, $C_1$–$C_8$alkoxy or halogen. Optionally, in at least one occurrence, $R^3$ is $OR^4$ wherein $R^4$ is selected from $C_1$–$C_8$alkyl, $C_3$–$C_7$cycloalkyl, and $C_6$–$C_9$polycycloalkyl. In a preferred embodiment, not more than four of the $R_3$ groups are hydrogen. For example, the present invention provides a compound having the formula:

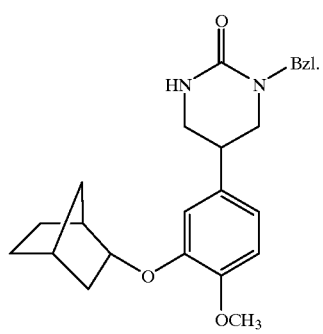

In another aspect the present invention provides a benzylated AROFYLLINE™ or analog thereof of the formulae:

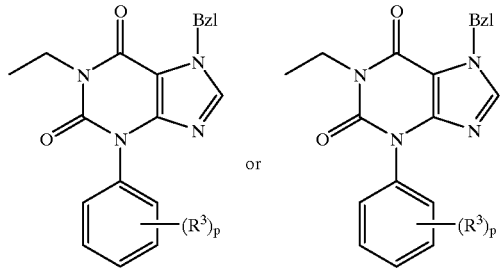

and isolated stereoisomers, salts and solvates thereof, wherein Bzl is a benzyl group of the formula

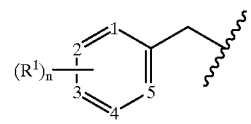

wherein each of the numerals 1, 2, 3, 4 and 5 may be carbon or nitrogen, with the proviso that the ring is aromatic and contains at least 3 carbon atoms; n is 5 and $R^1$ at each occurrence is independently selected from halogen, nitro, $R^2$, $NR^2_{(m)}$, and $OR^2$ wherein m=0, 1, 2, or 3 and $R^2$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^2$ group may be optionally substituted with one or more fluorine atoms, hydroxyl or $C_1$–$C_8$alkoxy; and the aryl portion of an $R^2$ group may be optionally substituted with $C_1$–$C_8$alkyl, $C_1$–$C_8$alkoxy or halogen; p is 5; and $R^3$ at each occurrence is independently selected from halogen, nitro, $R^4$, $NR^2_{(q)}$, and $OR^4$ wherein q=0, 1, 2, or 3 and $R^4$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^4$ group may be optionally substituted with one or more fluorine atoms, hydroxyl or $C_1$–$C_8$alkoxy; and the aryl portion of an $R^4$ group may be optionally substituted with $C_1$–$C_8$alkyl, $C_1$–$C_8$alkoxy or halogen. Optionally, in at least one occurrence, $R^3$ is halogen or $OR^4$ wherein $R^4$ is selected from $C_1$–$C_8$alkyl, $C_3$–$C_7$cycloalkyl, and $C_6$–$C_9$polycycloalkyl. For example, the present invention provides a benzylated AROFYLLINE™ or analog thereof compound having the formulae:

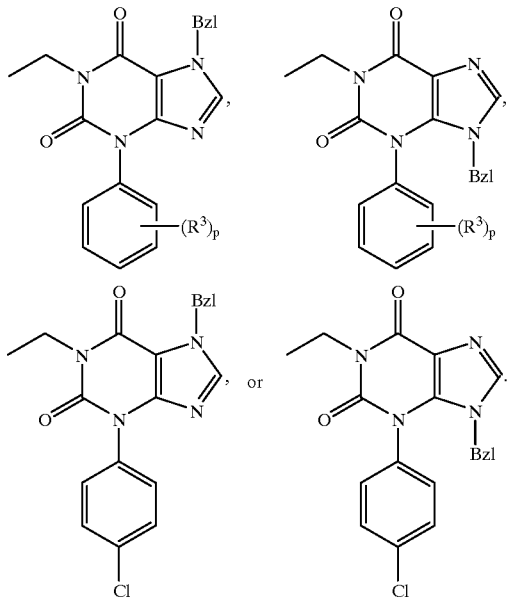

In another aspect the present invention provides a benzylated CIPAMFYLLINE™ or analog thereof compound of the formulae:

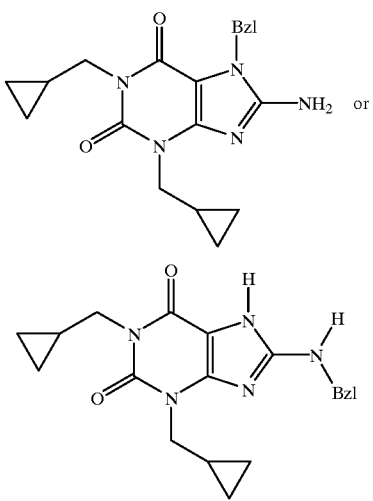

and isolated stereoisomers, salts and solvates thereof, wherein Bzl is a benzyl group of the formula

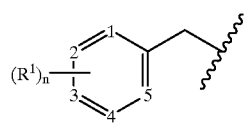

wherein each of the numerals 1, 2, 3, 4 and 5 may be carbon or nitrogen, with the proviso that the ring is aromatic and contains at least 3 carbon atoms; n is 5 and $R^1$ at each occurrence is independently selected from halogen, nitro, $R^2$, $NR^2_{(m)}$, and $OR^2$ wherein m=0, 1, 2, or 3 and $R^2$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^2$ group may be optionally substituted with one or more fluorine atoms, hydroxyl or $C_1$–$C_8$alkoxy; and the aryl portion of an $R^2$ group may be optionally substituted with $C_1$–$C_8$alkyl, $C_1$–$C_8$alkoxy or halogen. For example, the present invention provides a benzylated CIPAMFYLLINE™ or analog thereof compound of the formula:

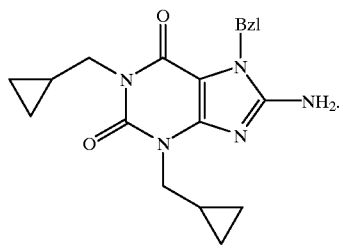

As another example, the present invention provides a benzylated CIPAMFYLLINE™ or analog thereof compound of the formula:

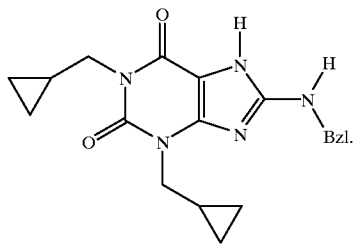

In addition to the above-mentioned method for improving the therapeutic ratio of PDE4 inhibitors through reduction or elimination of emetogenic properties while allowing retention of PDE activity, and the compounds of the present invention, the present invention also provides for inventive pharmaceutical compositions comprising a compound of the present invention and a pharmaceutically acceptable carrier, diluent or excipient. Furthermore, the present invention provides various methods for treating and/or preventing various biological, e.g., medical, conditions, where those methods employ a compound of the present invention, or a pharmaceutical composition of the present invention. Those methods for treating and/or preventing various biological conditions include the following.

A method for treating or preventing an inflammatory condition or disease in a patient, comprising administering to the patient in need thereof an amount of a benzylated PDE4 inhibitor, where the amount is effective to treat or prevent the inflammatory condition or disease of the patient, and where the benzylated PDE4 inhibitor is prepared by a benzylation method described herein. In addition, the present invention provides a method for treating or preventing an inflammatory condition or disease in a patient, comprising administering to the patient in need thereof an amount of a benzylated compound as described herein, where the amount is effective to treat or prevent the inflammatory condition or disease of the patient. In one aspect, the PDE4 inhibitor inhibits an enzyme selected from phosphodiesterase 4 A, B, C or D or any combination thereof including all splice variants of PDE4 A, B, C and D. In various aspects, the inflammatory condition or disease is an autoimmune condition or disease; or involves acute or chronic inflammation of bone and/or cartilage compartments of joints; or is an arthritis selected from rheumatoid arthritis, gouty arthritis or juvenile rheumatoid arthritis; or is asthma; or is associated with the disregulation of T-cells; or the inflammatory condition or disease is multiple sclerosis; or the inflammatory condition or disease is pulmonary sarcadosis; or the inflammatory condition or disease is ocular inflammation or allergy; or the inflammatory condition or disease is an inflammatory bowel disease, where the inflammatory bowel disease may be Crohn's disease or ulcerative colitis; or the inflammatory condition or disease is an inflammatory cutaneous disease, where the inflammatory cutaneous disease may be psoriasis or dermatitis; or the inflammatory condition or disease is chronic obstructive pulmonary disease (COPD), bronchitis, emphysema or acute respiratory distress syndrome (ARDS). In another aspect, the inflammatory condition or disease is associated with elevated levels of inflammatory cytokines. In various aspects, the inflammatory cytokine is IL-2, IL-4 or IL-5; or the inflammatory cytokine is IFN-γ; or the inflammatory cytokine is TNF-α.

A method for treating or preventing a disease or condition in a patient, where the disease or condition is associated with pathological conditions that are modulated by inhibiting enzymes associated with secondary cellular messengers, the method comprising administering to the patient in need thereof an amount of a benzylated PDE4 inhibitor, wherein the amount is effective to treat or prevent a disease or condition associated with pathological conditions that are modulated by inhibiting enzymes associated with secondary cellular messengers, and wherein the benzylated PDE4 inhibitor is prepared by a benzylation process according to the present invention. In addition, the present invention provides a method for treating or preventing a disease or condition in a patient, where the disease or condition is associated with pathological conditions that are modulated by inhibiting enzymes associated with secondary cellular messengers, the method comprising administering to the patient in need thereof an amount of a benzylated compound according to the present invention, or a pharmaceutical composition containing a benzylated compound according to the present invention, wherein the amount is effective to treat or prevent a disease or condition associated with pathological conditions that are modulated by inhibiting enzymes associated with secondary cellular messengers. In various aspects, the enzyme is a cyclic AMP phosphodiesterase; or the enzyme is phosphodiesterase 4.

A method of treating or preventing transplant rejection in a patient, the method comprising administering to the patient in need thereof an amount of a benzylated PDE4 inhibitor, where the amount is effective to treat or prevent transplant rejection in the patient, and wherein the benzylated PDE4 inhibitor is prepared by a benzylation process according the present invention. In addition, the present invention provides a method of treating or preventing transplant rejection in a patient, the method comprising administering to the patient in need thereof an amount of a benzylated compound according to the present invention, or a composition comprising a compound according to the present invention and a pharmaceutically acceptable carrier, diluent and excipient, where the amount is effective to treat or prevent transplant rejection in the patient. In one aspect the rejection is due to graft versus host disease.

A method of treating or preventing uncontrolled cellular proliferation in a patient, the method comprising administering to the patient in need thereof an amount of a benzylated PDE4 inhibitor, where the amount is effective to treat or prevent uncontrolled cellular proliferation in the patient, and wherein the benzylated PDE4 inhibitor is prepared by a process according to the present invention. In addition, the present invention provides a method of treating or preventing uncontrolled cellular proliferation in a patient, the method comprising administering to the patient in need thereof an amount of a benzylated compound according to the present invention, or a composition comprising a benzylated compound according to the present invention and a pharmaceutically acceptable carrier, diluent or excipient, where the amount is effective to treat or prevent uncontrolled cellular proliferation in the patient. In one aspect, the uncontrolled cellular proliferation is caused by a cancer selected from leukemia and solid tumors.

A method of treating or preventing conditions associated with the central nervous system (CNS) in a patient, the method comprising administering to the patient in need thereof an amount of a benzylated PDE4 inhibitor, where the amount is effective to treat or prevent conditions associated with the central nervous system (CNS) in the patient, and wherein the benzylated PDE4 inhibitor is prepared by a process according to the present invention. In addition, the present invention provides a method of treating or preventing conditions associated with the central nervous system (CNS) in a patient, the method comprising administering to the patient in need thereof an amount of a benzylated compound according to the present invention, or a composition comprising a benzylated compound according to the present invention and a pharmaceutically acceptable carrier, diluent or excipient, where the amount is effective to treat or prevent conditions associated with the central nervous system (CNS) in the patient. In one aspect, the condition associated with the central nervous system (CNS) is depression. In another aspect, the condition is long-term memory ostentation and learning enhancement.

A method of treating or preventing diseases in a patient, the disease associated with viral infection, the method comprising administering to the patient in need thereof an amount of a benzylated PDE4 inhibitor, where the amount is effective to treat or prevent diseases associated with viral infection in the patient, and wherein the benzylated PDE4 inhibitor is prepared by a process according to the present invention. In addition, the present invention provides a method of treating or preventing diseases in a patient, the disease associated with viral infection, the method comprising administering to the patient in need thereof an amount of a benzylated compound according to the present invention, or a composition comprising a pharmaceutically acceptable carrier, diluent or excipient in combination with a benzylated compound of the present invention, where the amount is effective to treat or prevent diseases associated with viral infection in the patient. In one aspect, the viral infection is due to the human immunodeficiency virus (HIV) and the disease is acquired immunodeficiency syndrome (AIDS).

A method of treating or preventing diseases in a patient, the disease associated with infection by a parasite, the method comprising administering to the patient in need thereof an amount of a benzylated PDE4 inhibitor, where the amount is effective to treat or prevent diseases associated with infection of the patient by a parasite, and wherein the benzylated PDE4 inhibitor is prepared by a process according to the present invention. In another aspect, the present invention provides a method of treating or preventing diseases in a patient, the disease associated with infection by a parasite, the method comprising administering to the patient in need thereof an amount of a benzylated compound according to the present invention, or a composition comprising a pharmaceutically acceptable carrier, diluent or excipient in combination with a benzylated compound of the present invention, where the amount is effective to treat or prevent diseases associated with infection of the patient by a parasite. In one aspect, the parasitic infection is due to the trypanosome Bruce and the disease is African sleeping sickness disease.

A method of treating or preventing cystic fibrosis in a patient, the method comprising administering to the patient in need thereof an amount of a benzylated PDE4 inhibitor, where the amount is effective to treat or prevent cystic fibrosis in the patient, where the amount is effective to treat or prevent cystic fibrosis, and wherein the benzylated PDE4 inhibitor is prepared by a benzylation process according to the present invention. In addition, the present invention provides a method of treating or preventing cystic fibrosis in a patient, the method comprising administering to the patient in need thereof an amount of a benzylated compound according to the present invention, or a composition comprising a pharmaceutically acceptable carrier, diluent or excipient in combination with a benzylated compound of the present invention, where the amount is effective to treat or prevent cystic fibrosis.

DETAILED DESCRIPTION OF THE INVENTION

It has been surprisingly discovered that compounds exhibiting PDE4 inhibitory activity and emetogenic effects will exhibit reduced emetogenic effects when the compound contains certain chemical substitution, and in particular certain chemical substitution including a benzyl group.

Definitions

As used herein, and unless otherwise specified, a benzyl group (Bzl, sometimes referred to as Bn) refers to a group of the formula

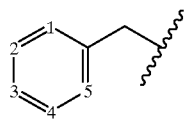

wherein each of the numerals 1, 2, 3, 4 and 5 may be carbon or nitrogen, and when a numeral is carbon then that numeral may be substituted with an organic or inorganic group.

In one aspect, a benzyl group (Bzl) refers to a group of the formula

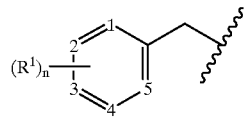

wherein each of the numerals 1, 2, 3, 4 and 5 may be carbon or nitrogen, with the proviso that the ring is aromatic and contains at least 3 carbon atoms;
n is 5 and $R^1$ at each occurrence is independently selected from halogen, nitro, $R^2$, $NR^2_{(m)}$, and $OR^1$ wherein m=0, 1, 2, or 3 and $R^2$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^2$ group may be optionally substituted with one or more fluorine atoms, hydroxyl or $C_1$–$C_8$alkoxy; and the aryl portion of an $R^2$ group may be optionally substituted with $C_1$–$C_8$alkyl, $C_1$–$C_8$alkoxy or halogen.

In one aspect, a benzyl group (Bzl) refers to a group of the formula

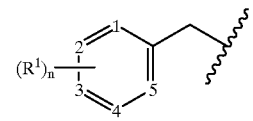

wherein each of the numerals 1, 2, 3, 4 and 5 may be carbon or nitrogen, with the proviso that the ring is aromatic and contains at least 4 carbon atoms;
n is 5 and $R^1$ at each occurrence is independently selected from halogen, nitro, $R^2$, and $OR^2$ wherein and $R^2$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, phenyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^2$ group may be optionally substituted with one or more fluorine atoms, hydroxyl or $C_1$–$C_8$alkoxy; and the phenyl portion of an $R^2$ group may be optionally substituted with $C_1$–$C_8$alkyl, $C_1$–$C_8$alkoxy or halogen.

In one aspect, a benzyl group (Bzl) refers to a group of the formula

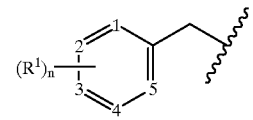

wherein each of the numerals 1, 2, 3, 4 and 5 may be carbon or nitrogen, with the proviso that the ring is aromatic and contains at least 3 carbon atoms;
n is 5 and $R^1$ at each occurrence is independently selected from halogen, nitro, $R^2$, $NR^2_{(m)}$, and $OR^2$ wherein m=0, 1, 2, or 3 and $R^2$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^2$ group may be optionally substituted with one or more fluorine atoms, hydroxyl or $C_1$–$C_8$alkoxy; and the aryl portion of an $R^2$ group may be optionally substituted with $C_1$–$C_8$alkyl, $C_1$–$C_8$alkoxy or halogen; with the proviso that at least one $R^1$ is $OR^2$.

In one aspect, a benzyl group (Bzl) refers to a group of the formula

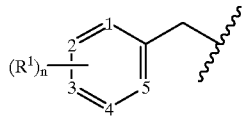

wherein each of the numerals 1, 2, 3, 4 and 5 is carbon; n is 5 and $R^1$ at each occurrence is independently selected from halogen, nitro, $R^2$, $NR^2_{(m)}$, and $OR^2$ wherein m=0, 1, 2, or 3 and $R^2$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^2$ group may be optionally substituted with one or more fluorine atoms, hydroxyl or $C_1$–$C_8$alkoxy; and the aryl portion of an $R^2$ group may be optionally substituted with $C_1$–$C_8$alkyl, $C_1$–$C_8$alkoxy or halogen; with the proviso that at least one $R^1$ is halogen.

In one embodiment, each of the aromatic ring atoms of the benzyl group is a carbon atom, so that the benzyl group has the formula

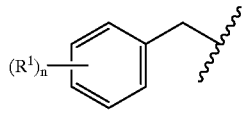

wherein n is 0, 1, 2, 3 or 4, and independently at each occurrence,
$R^1$ is selected from halogen, nitro, $R^2$, $NR^2_{(m)}$, and $OR^2$ wherein m=0, 1, 2, or 3 and $R^2$ is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^2$ group may be optionally substituted with one or more fluorine atoms, hydroxyl or $C_1$–$C_8$alkoxy; and the aryl portion of an $R^2$ group may be optionally substituted with $C_1$–$C_8$alkyl, $C_1$–$C_8$alkoxy or halogen.

In any of the above embodiments, in a further embodiment of the present invention, n is 1, 2 or 3 and in at least one occurrence $R^1$ is halogen.

In a compound as disclosed herein, when any variable occurs more than one time in any constituent or in a benzylated compound, its definition on each occurrence is independent of its definition at every other occurrence. Combinations of substituents and/or variables are permissible only if such combinations result in stable compounds. The compounds useful in the methods and compositions of the present invention, as well as the compounds of the present invention, may have asymmetric centers and occur as racemates, racemic mixtures and as individual diastereomers, or enantiomers with all isomeric forms being included in the present invention. A racemate or racemic mixture does not imply a 50:50 mixture of stereoisomers. Also, unless otherwise indicated, the terms "a" and "an" refer to one, or more than one, of the indicated items. For example, "a compound" includes one and more than one compound, and "an" isomer refers to one and more than one isomer.

In the benzylated compounds, a salt is preferably a pharmaceutically acceptable salt, where salts includes acid addition salts and base addition salts. A "pharmaceutically acceptable salt" and "salts thereof" means organic or inorganic salts of the pharmaceutically important molecule. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically important organic molecule may have more than one charged atom in its structure. Situations where multiple charged atoms are part of the molecule may have multiple counterions. Hence, the molecule of a pharmaceutically acceptable salt may contain one or more than one charged atoms and may also contain, one or more than one counterion. The desired charge distribution is determined according to methods of drug administration. Examples of pharmaceutically acceptable salts are well known in the art but, without limiting the scope of the present invention, exemplary presentations can be found in the Physician's Desk Reference, The Merck Index, The Pharmacopoeia and Goodman & Gilman's The Pharmacological Basis of Therapeutics.

Acid addition salts refer to those salts formed from benzylated compounds of the present invention and inorganic acids such as hydrochloric acid, hydrobromic acid, sulfuric acid, nitric acid, phosphoric acid and the like, and/or organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

Base addition salts include those salts derived from benzylated compounds of the present invention and inorganic bases such as sodium, potassium, lithium, ammonium, calcium, magnesium, iron, zinc, copper, manganese, aluminum salts and the like. Suitable salts include the ammonium, potassium, sodium, calcium and magnesium salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, trimethylamine, dicyclohexylamine, lysine, arginine, histidine, caffeine, procaines, hydrabamine, choline, betaine, ethylenediamine, glucosamine, methylglucamine, theobromine, purines, piperazine, piperidine, N-ethylpiperidine, and the like.

"Alkoxy" refers to alkyl-O—, where "O" represents oxygen and alkyl is defined below.

"Alkoxyalkyl" refers to alkyl$^1$-O-alkyl$^2$-, where "O" represents oxygen and alkyl$^1$ represents the alkoxy portion, i.e., alkyl[1]-O is alkoxy, while alkyl[2] represents the alkyl portion of the alkoxyalkyl group. In an alkoxyalkyl group, each of alkyl[1] and alkyl[2] is an alkyl group as defined below, with the comment that alkyl[1] is monovalent as it has one open valence site that is bound to oxygen, while alkyl[2] is divalent, as it is bound to both oxygen and the remainder of the molecule.

"Alkyl" refers to an acyclic chain of carbon atoms that may be branched or unbranched (linear). Methyl, ethyl, propyl (including n-propyl and iso-propyl) butyl (including n-butyl, iso-butyl, sec-butyl, and t-butyl), pentyl (including numerous isomers) and hexyl (including numerous isomers) are alkyl groups having 1 to 6 carbon atoms (commonly referred to as lower alkyl groups), and are exemplary of alkyl groups of the invention. As referred to herein, an alkyl group may have unsaturation between any two carbons, i.e., the alkyl group may have double and/or triple bonds. Thus, the term alkyl encompasses alkenyl groups, which are unsaturated aliphatic groups having at least one double bond, as well as alkynyl groups, which are unsaturated aliphatic groups which may be either straight- or branched-chain and have one or more triple bonds. In various embodiments the alkyl groups have no more than about 20 carbons atoms, or no more than about 18, or 16, or 14, or 12, or 10 carbons atoms, and may be ethyl, propynyl, 4-methylpentynyl and so on, and structural isomers thereof. In addition, the term alkyl encompasses monovalent as well as polyvalent alkyl groups, where methyl ($CH_3$—) is an exemplary monovalent alkyl group, while methylene (—$CH_2$—) is an exemplary polyvalent, and more specifically a divalent alkyl group. In one embodiment, alkyl excludes methyl. In another embodiment, the alkyl group has at least 3 carbon atoms.

"Alkylamide" refers to an amide group wherein either or both of the carbon and nitrogen atoms are bonded to alkyl group(s).

"Alkylcarboxyl" refers to a divalent alkyl group wherein one of the open valence sites is bonded to a carboxyl group, while the remaining open valence site is bonded to the remainder of the molecule.

"Alkylcarboxylate" refers to a divalent alkyl group wherein one of the open valence sites is bonded to a carboxylate group, while the remaining open valence site is bonded to the remainder of the molecule.

"Alkylcycloalkyl" refers to a cycloalkyl group that is bonded both to an alkyl group and to the remainder of the molecule. Each of alkyl and cycloalkyl are defined herein.

"Amide" refers to a group of the formula

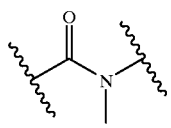

where the amide group may be joined to the remainder of the molecule through either the carbonyl group or the nitrogen atom.

"Aryl" refers to an aromatic hydrocarbon ring system. The ring system may be monocyclic or fused polycyclic (e.g., bicyclic, tricyclic, etc.). In various embodiments, the monocyclic aryl ring is C5-C10, or C5-C7, or C5-C6, where these carbon numbers refer to the number of carbon atoms that make up the ring system. A C6 ring system, i.e., a phenyl ring, is a preferred aryl ring. In various embodiments, the polycyclic ring is a bicyclic aryl ring, where preferred bicyclic aryl rings are C8-C12, or C9-C10. A naphthyl ring, which has 10 carbon atoms, is a preferred polycyclic aryl ring. Aryl rings may be substituted or unsubstituted. In one embodiment, the aryl ring is unsubstituted. In another embodiment, the aryl ring is substituted with 1 substituent (i.e., the aryl ring is monosubstituted), or 1–2 substituents, or 1–3 substituents, or 1–4 substituents, etc.

"Carboxylate" refers to a group of the formula

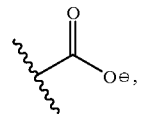

i.e., —$COO^-$, where there is a positively charged counterion present.

"Carboxyl" or "Carboxylic acid" refers to a protonated carboxylate.

"Cycloalkyl" refers to a cyclic alkyl group. Suitable cycloalkyl groups include, for example, cyclohexyl, cyclopropyl, cyclopentyl, and cycloheptyl. Cycloalkenyl is an example of a cycloalkyl group, where suitable cycloalkenyl groups include, for example, cyclopentenyl and cyclohexenyl.

"Halogen" refers to fluorine, chlorine, bromine and iodine.

"Heteroalkyl" refers to a saturated or unsaturated, straight or branched, chain containing carbon and at least one heteroatom. The heteroalkyl group may, in various embodiments, have one heteroatom, or 1–2 heteroatoms, or 1–3 heteroatoms, or 1–4 heteroatoms. Heteroalkyl chains may contain from 1 to 18 (i.e., 1–18) member atoms (carbon and heteroatoms) in the chain, and in various embodiments contain 1–12, or 1–6, or 1–4 member atoms. Independently, in various embodiments, the heteroalkyl group has zero branches (i.e., is a straight chain), one branch, two branches, or more than two branches. Independently, in one embodiment, the heteroalkyl group is saturated. In another embodiment, the heteroalkyl group is unsaturated. In various embodiments, the unsaturated heteroalkyl may have one double bond, two double bonds, more than two double bonds, and/or one triple bond, two triple bonds, or more than two triple bonds. Heteroalkyl chains may be substituted or unsubstituted. In one embodiment, the heteroalkyl chain is unsubstituted. In another embodiment, the heteroalkyl chain is substituted. A substituted heteroalkyl chain may have 1 substituent (i.e., be monosubstituted), or may have 1–2 substituents, or 1–3 substituents, or 1–4 substituents, etc. Exemplary heteroalkyl groups include esters (—C(=O)—OR) and ketones (—C(=O)—). In another embodiment, the heteroalkyl group is not substituted.

"Heteroaryl" is an aromatic ring system or a semi-aromatic system of rings or a pseudo aromatic ring or rings containing carbon and at least one heteroatom in at least one of the rings. The heteroaryl group may, in various embodiments, have one heteroatom, or 1–2 heteroatoms, or 1–3 heteroatoms, or 1–4 heteroatoms in the ring. The heteroaryl group may further include more than one ring system, which in various embodiments may include one heteroatom or 1–2 heteroatoms, or 1–3 heteroatoms, or 1 heteroatom in each ring system, or 1–4 heteroatoms in each ring system. The heteroaryl group which comprises more than one ring system may, in various embodiments have one or more than one of the ring systems aromatic. Heteroaryl rings may be monocyclic or polycyclic, where the polycyclic ring may contain fused, spiro or bridged ring junctions. In one embodiment, the heteroaryl is selected from monocyclic and bicyclic. Monocyclic heteroaryl rings may contain from about 5 to about 10 member atoms (carbon and heteroatoms), preferably from 5–7, and most preferably from 5–6 member atoms in the ring. Bicyclic heteroaryl rings may contain from about 8–12 member atoms, or 9–10 member atoms in the ring. The heteroaryl ring may be unsubstituted or substituted. In one embodiment, the heteroaryl ring is unsubstituted. In another embodiment, the heteroaryl ring is substituted. The substituted heteroaryl ring may contain 1 substituent, or 1–2 substituents, or 1–3 substituents, or 1–4 substituents, etc. Exemplary heteroaryl rings include benzofuran, benzothiophene, furan, imidazole, indole, isothiazole, oxazole, pyrazine, pyrazole, pyridazine, pyridine, pyrimidine, pyrrole, quinoline, thiazole and thiophene. In one embodiment, the heteroaryl group does not have any substituents.

"Heteroatom" is a nitrogen, sulfur, oxygen or silicon atom. Groups containing more than one heteroatom may contain different heteroatoms.

"Heterocycloalkyl" refers to a saturated or unsaturated, monocyclic or polycyclic (e.g., bicyclic, tricyclic, etc.) ring containing carbon and at least one heteroatom. Heterocyclic aliphatic rings are not aromatic per se but may be pseudo-aromatic and/or readily be made aromatic through methods known in the art. The heterocyclic aliphatic ring may, in various embodiments, have one heteroatom, or 1–2 heteroatoms, or 1–3 heteroatoms, or 1–4 heteroatoms, etc. In one embodiment, the heterocyclic aliphatic ring is monocyclic, where the monocyclic ring may have 3–10, or 4–7, or 5–6 member atoms. In another embodiment, the heterocyclic aliphatic ring is polycyclic, where in various embodiments, the ring may be bicyclic, or may be tricyclic, or may be either bicyclic or tricyclic. A polycyclic ring system may have one or more fused, spiro or bridged ring systems. The polycyclic heterocyclic aliphatic ring system may have 6–12, or 9–10 member atoms. The heterocyclic ring may be unsubstituted or substituted. In one embodiment, the heterocyclic ring is unsubstituted. In another embodiment, the heterocyclic ring is substituted. The substituted heterocyclic ring may contain 1 substituent, or 1–2 substituents, or 1–3 substituents, or 1–4 substituents, etc. Exemplary heterocyclic aliphatic rings include piperazyl, morpholinyl, tetrahydrofuranyl, tetrahydropyranyl and piperidyl. In another embodiment, the heterocycloalkyl is not substituted.

"Hydroxyalkyl" refers to an alkyl group that is bonded to both a hydroxy (HO—) group and to the remainder of the molecule. In other words, a group that may be represented as HO-alkyl-.

"Indanyl" refers to an indane group, i.e., a group of the structure

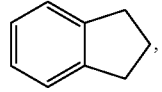

wherein one of the carbons of the indane group is bonded to the remainder of the molecule.

"Phenoxyalkyl" refers to phenyl-O-alkyl-, where "phenyl-O" is the phenoxy portion of the phenoxyalkyl group, and "alkyl" is the alkyl portion of the phenoxyalkyl group. The alkyl portion of the phenoxyalkyl group is defined above, with the comment that in a phenoxyalkyl radical, the alkyl group is divalent.

"Phenylalkyl" refers to phenyl-alkyl-, where "pheny" is the phenyl portion of the phenylalkyl group, and "alkyl" is the alkyl portion of the phenylalkyl group. The alkyl portion of the phenylalkyl group is defined above, with the comment that in a phenylalkyl radical, the alkyl group is divalent.

"Polycycloalkyl" refers to an arrangement of carbon atoms wherein at least one carbon atom is a part of at least two separately identifiable rings. The polycycloalkyl group may contain bridging between two carbon atoms, where bicyclo[1.1.0]butyl, bicyclo[3.2.1]octyl, bicyclo[5,2.0]nonyl, tricycl[2.2.1.0$^1$]heptyl, norbornyl and pinanyl are representative examples. The polycycloalkyl group may contain one or more fused ring systems, where decalinyl (radical from decalin) and perhydroanthracenyl are representative examples. The polycycloalkyl group may contain a spiro union, in which a single atom is the only common member of two rings. Spiro[3.4]octyl, spiro[3.3]heptyl and spiro[4.5]decyl are representative examples. Polycycloalkyl groups having 6, 7, 8 or 9 carbon atoms, i.e., $C_6$–$C_9$polycycloalkyl, are a preferred polycycloalkyl group of the present invention.

In describing the present invention, the following abbreviations may be used, where these abbreviations have the meaning as indicated in the following Table.

| Abbreviation | Full name |
|---|---|
| 5-ASA | 5-aminosalicylic acid |
| Ab | Antibody |
| ABTS | 2,2'-azino-di-[3-ethylbenzthiazoline sulphonate] |
| ACD | Acid citrate dextrose |
| AcOH | Acetic Acid |
| ACVP | American College of Veterinary Practice |
| ANOVA | Analysis of Variance |
| Ar | Argon |
| BCR-ABL | Oncogene in chromosome 9:22 translocation in CML |
| BINAP | 2,2'-Bis(diphenylphosphino)-1,1'-binaphthyl |
| Bn | Benzyl |
| BnBr | Benzyl Bromide |
| BOC | tert-Butoxycarbonyl |
| cAMP | Cyclic adenosine 3'-5'-monophosphate |
| cat | Catalytic |
| CD | Cluster designation |
| CFA | Complete Freund's adjuvant |
| cGMP | Cyclic guanosine 3'-5'-monophosphate |
| CIA | Collagen Induced Arthritis |
| CLL | Chronic lymphocytic leukemia |
| CML | Chronic myelogenous leukemia |
| CNS | Central Nervous System |
| Con A | Concanavalin A |
| COX | Cyclooxygenase |
| cPent | Cyclopentyl |
| cPentBr | Cyclopentyl bromide |
| CRE | cAMP response element |
| CsA | Cyclosporin A |
| DMAP | 4-Dimethylaminopyridine |
| DMARD | Disease modifying anti-rheumatic drug |
| DMF | N,N-Dimethylformamide |
| DMSO | dimethylsulfoxide |
| DNA | Deoxyriboneucleic acid |
| DNBS | 2,4-Dinitrobenzene sulphoric acid |
| dppf | 1,1'-Bis(diphenylphosphino)ferrocene |
| dppp | 1,3'-Bis(diphenylphosphino)propane |
| $EC_{50}$ | Concentration at which a 50% of maximum observable effect is noted |
| EDTA | Ethylenediaminotetraacetic acid |
| ELISA | Enzyme-linked immunosorbent assay |
| EtOAc | Ethyl acetate |
| EtOH | Ethyl alcohol |
| FBS | Fetal bovine serum |
| FCS | Fetal calf serum |
| fMLP | Formyl-methionyl leucine phenylalanine |
| g.i. | Gastrointestinal |
| H & E | Haematoxylin and eosin |
| HARBS | High affinity rolipram binding site |
| HBSS | Hanks Balanced Salt Solution |
| HMPA | Hexamethylphosphoramide |
| HPLC | High pressure liquid chromatography |
| i.p. | intraperitoneal |
| IBD | Inflammatory bowel disease |
| IBMX | 3-isobutyl-1-methylxanthine |
| IC | Inhibitory concentration |
| $IC_{50}$ | Concentration at which 50% inhibition is observed |
| IFA | Incomplete Freund's adjuvant |
| IFN-γ | Interferon gamma |
| IL | Interleukin |
| LAH | Lithium aluminum hydride |
| LDA | Lithium diisopropylamide |

-continued

| Abbreviation | Full name |
|---|---|
| LN | Lymph node |
| LPS | lipopolysaccharide |
| LTB4 | Leukotriene B4 |
| luc | luciferase |
| Me | Methyl |
| MeOH | Methyl alcohol |
| MHC | Major histocompatibility class |
| MLR | Mixed lymphocyte reaction |
| MPO | myeloperoxidase |
| Ms | Methanesulfonyl |
| MsCl | Methanesulfonyl chloride |
| NBS | N-Bromosuccinimide |
| n-BuLi | n-Butyllithium |
| n-BuSH | n-Butanethiol |
| NF-κB | Nuclear factor kappa B |
| NSAID | Non-steroidal anti-inflammatory drug |
| p.t. | Post-transplant |
| PBS | Phosphate buffered saline |
| Pcc | Pigeon cytochrome C |
| PDE | Phosphodiesterase |
| PEG | Polyethylene glycol |
| PG | Prostaglandin |
| PMS | Phenazine methosulfate |
| PMSF | Phenyl methyl sulfonyl fluoride |
| pTsOH | p-Toluenesulfonic acid monohydrate |
| Py | Pyridine |
| RA | Rheumatoid arthritis |
| RF | Rheumatoid factor |
| $R_f$ | Retardation factor |
| ROS | Reactive oxygen species |
| RPMI | Rosewell Park Memorial Institute |
| RTX | Resiniferitoxin |
| SAR | Structure activity relationship |
| TBAF | Tetrabutylammonium fluoride |
| TBDMS | tert-Butyldimethylsilyl |
| TBDMSCl | tert-Butyldimethylsilyl chloride |
| TCR | T-cell receptor |
| TEA | Triethylamine |
| Tf | Trifluoromethanesulfonyl |
| TFA | Trifluoroacetic acid |
| Th | T helper |
| THF | Tetrahydrofuran |
| TNBS | Trinitrobenzene sulfonic acid |
| TNF-α | Tumour necrosis factor alpha |
| Trolox ® | 6-hydroxy-2.5.7.8-tetramethylchroman-2-carboxylic acid |
| TsOH | p-Toluenesulfonic acid monohydrate |
| XTT | 2,3-bis[2-methoxy-4-nitro-5-sulfo-phenyl]-2H-tetrazolium 5-carboxanilide inner salt |
| μM | Micro molar |

Method of the Present Invention

In one aspect, the present invention is directed to a method for improving the therapeutic ratio of PDE4 inhibitors through reduction or elimination of emetogenic properties while allowing retention of PDE activity. The method comprises benzylation of a PDE4 inhibitor, wherein the benzylation places a benzyl group on a carbon (referred to herein as C-benzylation) or nitrogen (referred to herein as N-benzylation) atom of a PDE4 inhibitor, to provide a benzylated PDE4 inhibitor. In one aspect of the invention, the benzylation places a benzyl group on a carbon atom of a PDE4 inhibitor. In another aspect of the invention, the benzylation places a benzyl group on a nitrogen atom of a PDE4 inhibitor. In one aspect of the invention, the benzylation places a benzyl group on a carbon atom or a nitrogen atom of a PDE4 inhibitor. In another aspect, the benzylation places two benzyl groups on a PDE4 inhibitor.

The addition of a benzyl group to a PDE4 inhibitor is readily accomplished by reacting the PDE4 inhibitor (or a protected version thereof) with a benzylating agent (or a protected version thereof) under conditions such that the benzylating agent forms a covalent bond to a carbon or nitrogen atom of the PDE4 inhibitor. As used herein, a benzylating agent includes a benzyl group as defined herein having a leaving group attached to the methylene carbon of the benzyl group, i.e., a leaving group alpha to the aromatic ring. Suitable leaving groups include halogens, e.g., chloride and bromide, and sulfonates, e.g., mesylate and tosylate. Such a benzylating agent has the general formula as shown below.

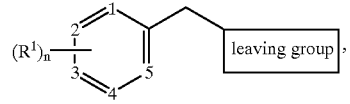

wherein n is 0, 1, 2, 3 or 4, and independently at each occurrence, $R^1$ is selected from halogen, nitro, $R^2$, $NR^2_{(m)}$, and $OR^2$ wherein m=0, 1, 2, or 3 and $R^2$ is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^2$ group may be optionally substituted with one or more fluorine atoms, hydroxyl or $C_1$–$C_8$alkoxy; and the aryl portion of an $R^2$ group may be optionally substituted with $C_1$–$C_8$alkyl, $C_1$–$C_8$alkoxy or halogen.

Reaction conditions whereby a PDE4 inhibitor will react with a benzylating agent so as to form a benzylated PDE4 inhibitor include basic conditions. In the presence of basic conditions, the one or more extractable hydrogens of the PDE4 inhibitor will react with base so that the PDE4 inhibitor forms the corresponding nucleophilic anion. The nucleophilic center will then react with the benzylating agent with concomitant displacement of the leaving group, so as to join the PDE4 inhibitor to the benzyl group. Benzylation chemistry in general is well known in the art, and may be applied to the goal of benzylating PDE4 inhibitors according to the present invention.

The basic conditions are created by combining the PDE4 inhibitor with a base, typically in a suitable solvent. Suitable bases must be selected based on the acidity of the hydrogen atom being removed from the PDE4 inhibitor. That is, a relatively more basic compound must be employed when the hydrogen being removed from the PDE4 inhibitor is relatively less extractable. Suitable bases for most instances include sodium hydride, potassium hydride, metal amine salts such as lithium amine salts, e.g., lithium diisopropylamide, and sodium amine salts, lithium hydroxide, sodium hydroxide, potassium hydroxide, sodium alkoxide or potassium alkoxide where alkoxide refers to O-alkyl and alkyl is defined herein.

Scheme 1 depicts general synthetic methodology that may be used for the introduction of a benzyl group at a location alpha to a carbonyl group. Scheme 1 depicts this methodology with an ester-containing molecule, and more specifically with a lactone, however, the same methodology may be used when the carbonyl group is part of a lactam or other amide-containing molecule, or when the carbonyl group is part of a non-lactone ester group or ketone group or carboxylic acid group. As discussed in more detail below, this general methodology may be applied to a carbonyl-containing compound that has substitution and/or when the benzylating agent has substitution.

Scheme 1

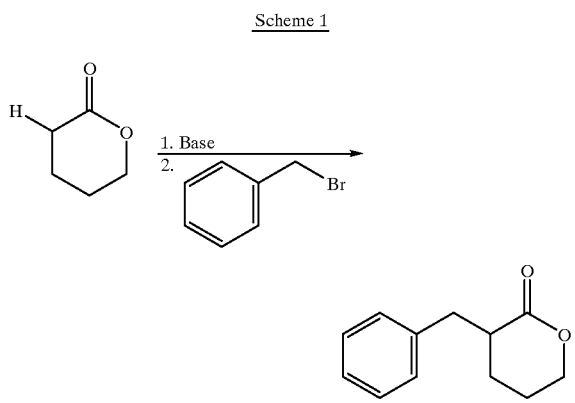

Although Scheme 1 illustrates one methodology that may be employed according to the present invention using an unsubstituted benzylation agent (and, more specifically, benzyl bromide, abbreviated as BnBr) to afford a benzylated product, any number of substituted benzylation agents can be used to generate a benzylated product with various substitution patterns on the benzyl ring. Substituted benzyl bromides are available commercially or may be generated from the corresponding substituted benzyl alcohol, benzaldehyde, benzoic acid or benzoic ester.

For example, substituted benzyl bromides can be prepared as outlined in Scheme 2. Thus, treatment of commercially available benzyl alcohol 1 with benzyl bromide and potassium carbonate in toluene gives the corresponding benzyloxy derivative 2, which is treated, without purification, with $PBr_3$ in diethyl ether to give the desired bromide compound 3 in quantitative yield. Any number of compounds related to compound 3 could be produced using similar methodology but starting with a different substituted benzyl alcohol.

Scheme 2

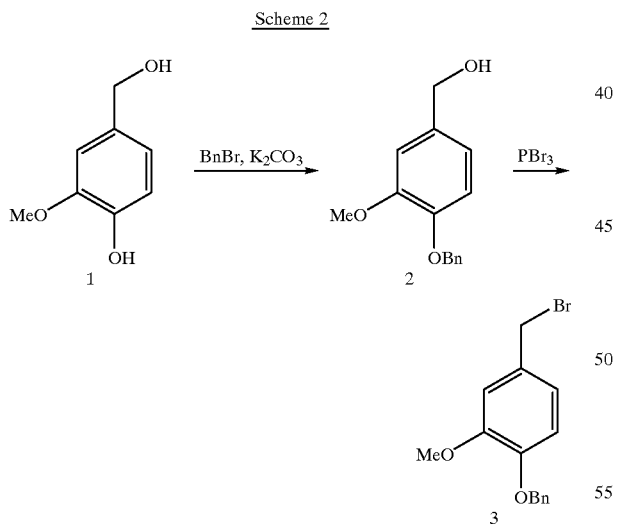

Substituted benzyl bromide compounds can also be prepared from commercially available substituted benzaldehydes, benzoic acids and benzoic esters by first converting these compounds to the corresponding alcohol. Benzyl aldehydes may be reduced to the corresponding alcohol by standard reducing conditions, e.g., sodium borohydride in methanol. In some instances, it may be necessary to protect other functionality on the benzyladehyde compound in order that the other functionality is not undesirably modified by the reduction conditions.

It may be necessary to protect certain reactive groups present in the PDE4 inhibitor from the benzylation reaction. Suitable protecting groups and methods for their use are described in "Protective Groups in Organic Synthesis", 3$^{rd}$ Edition, by Greene, T. W. and Wuts, P. G. M., John Wiley & Sons, 1999.

As for selection of the PDE4 inhibitor, many of these are known in the art and may be advantageously benzylated according to the present invention. Suitable PDE4 inhibitors include, without limitation, ROLIPRAM™, ARIFLO™, WAY-PDA-641, Ro-20-1724, RP 73401, CP-80,633-A, AROFYLLINE™, and CIPAMFYLLINE™. In a preferred embodiment, benzylation of a PDE4 inhibitor occurs by placing a benzyl group on a carbon atom of the PDE4 inhibitor. PDE4 inhibitors suitable for benzylation on a carbon atom include, without limitation, ROLIPRAM™ and ARIFLO™. In another aspect, the present invention employs PDE4 inhibitors suitable for benzylation on a nitrogen atom, where such PDE4 inhibitors include, without limitation, WAY-PDA-641, Ro-20-1724, RP 73401, CP-80, 633-A, AROFYLLINE™, and CIPAMFYLLINE™. The following literature references, in addition to those provided in the Background of the present specification, describe various PDE4 inhibitors and methodology to identify a PDE4 inhibitor: PCT International Publication No. WO92/12961; *J. Med. Chem.* 1997, 40, 1417–1421; *Organic Process Research & Development* 1998, 2, 157–168; *J. Med. Chem.*, 1994, 37, 1696–1703; and U.S. Pat. Nos. 5,124,455; 5,814,651; 3,636,039; 4,308,278; 5,223,504; 5,734,051.

In one aspect of the present invention, the benzylated PDE4 inhibitor comprises a benzyl group, and independently of the benzyl group the benzylated PDE4 inhibitor further comprises the group

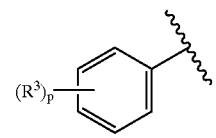

wherein p is 5; and $R^3$ at each occurrence is independently selected from halogen, nitro, $R^4$, $NR^2_{(q)}$, and $OR^4$ wherein q=0, 1, 2, or 3 and $R^4$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^4$ group may be optionally substituted with one or more fluorine atoms, hydroxyl or $C_1$–$C_8$alkoxy; and the aryl portion of an $R^4$ group may be optionally substituted with $C_1$–$C_8$alkyl, $C_1$–$C_8$alkoxy or halogen. In one aspect of the invention $R^3$ is $OR^4$ in at least one occurrence wherein $R^4$ is selected from $C_1$–$C_8$alkyl, $C_3$–$C_7$cycloalkyl, and $C_6$–$C_9$polycycloalkyl.

C-Benzylation of PDE4 Inhibitors

In one aspect of the invention, the benzylation may provide a benzyl group attached to a carbon atom of the PDE4 inhibitor. In various embodiments of this aspect of the invention, the benzyl group being added to the PDE4 inhibitor has one of the following definitions:

A benzyl group (Bzl) of the formula

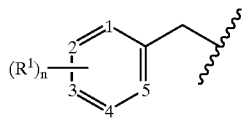

wherein each of the numerals 1, 2, 3, 4 and 5 may be carbon or nitrogen, with the proviso that the ring is aromatic and contains at least 3 carbon atoms; n is 5 and $R^1$ at each occurrence is independently selected from halogen, nitro, $R^2$, $NR^2_{(m)}$, and $OR^2$ wherein m=0, 1, 2, or 3 and $R^2$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, C6–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^2$ group may be optionally substituted with one or more fluorine atoms, hydroxyl or $C_1$–$C_8$alkoxy; and the aryl portion of an $R^2$ group may be optionally substituted with $C_1$–$C_8$alkyl, $C_1$–$C_8$alkoxy or halogen; or A benzyl group (Bzl) of the formula

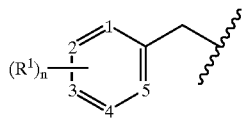

wherein each of the numerals 1, 2, 3, 4 and 5 may be carbon or nitrogen, with the proviso that the ring is aromatic and contains at least 4 carbon atoms; n is 5 and $R^1$ at each occurrence is independently selected from halogen, nitro, $R^2$, and $OR^2$ wherein and $R^2$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, phenyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^2$ group may be optionally substituted with one or more fluorine atoms, hydroxyl or $C_1$–$C_8$alkoxy; and the phenyl portion of an $R^2$ group may be optionally substituted with $C_1$–$C_8$alkyl, $C_1$–$C_8$alkoxy or halogen; or A benzyl group (Bzl) of the formula

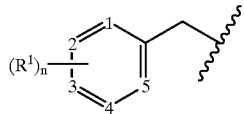

wherein each of the numerals 1, 2, 3, 4 and 5 may be carbon or nitrogen, with the proviso that the ring is aromatic and contains at least 3 carbon atoms; n is 5 and $R^1$ at each occurrence is independently selected from halogen, nitro, $R^2$, $NR^2_{(m)}$, and $OR^2$ wherein m=0, 1, 2, or 3 and $R^2$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^2$ group may be optionally substituted with one or more fluorine atoms, hydroxyl or $C_1$–$C_8$alkoxy; and the aryl portion of an $R^2$ group may be optionally substituted with $C_1$–$C_8$alkyl, $C_1$–$C_8$alkoxy or halogen; with the proviso that either (a) at least one $R^1$ is $OR^2$, or (b) the benzyl ring contains at least two $R^1$ groups that are not hydrogen.

A benzyl group (Bzl) of the formula

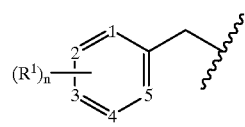

wherein each of the numerals 1, 2, 3, 4 and 5 may be carbon or nitrogen, with the proviso that the ring is aromatic and contains at least 3 carbon atoms; n is 5 and $R^1$ at each occurrence is independently selected from halogen, nitro, $R^2$, $NR^2_{(m)}$, and $OR^2$ wherein m=0, 1, 2, or 3 and $R^2$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^2$ group may be optionally substituted with one or more fluorine atoms, hydroxyl or $C_1$–$C_8$alkoxy; and the aryl portion of an $R^2$ group may be optionally substituted with $C_1$–$C_8$alkyl, $C_1$–$C_8$alkoxy or halogen; with the proviso that $R_1$ is hydrogen at either 1, 2, or 3 occurrences of n, but not 4 or 5 occurrences.

In one aspect of the invention, the PDE4 inhibitor is ROLIPRAM™ or an analog thereof. In one embodiment, the benzylated ROLIPRAM™ or analog thereof according to the inventive method has the formula:

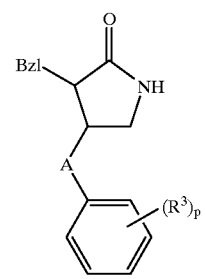

and isolated stereoisomers, salts and solvates thereof, wherein Bzl is a benzyl group; A is selected from a direct bond, optionally substituted $C_1$-$C_5$alkylene, optionally substituted $C_2$-$C_5$alkenyl and optionally substituted phenylene; p is 5; and $R^3$ at each occurrence is independently selected from halogen, nitro, $R^4$, $NR^2_{(q)}$, and $OR^4$ wherein q=0, 1, 2, or 3 and $R^4$ at each occurrence is independently selected from H, $C_1$-$C_8$alkyl, alkoxyalkyl having 3–7 carbons in the alkoxy portion and 2–4 carbons in the alkyl portion, phenoxyalkyl having 2–6 carbons in the alkyl portion, $C_3$-$C_7$cycloalkyl, $C_6$-$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$-$C_4$alkyl and indanyl; wherein the alkyl portion of an $R^4$ group may be optionally substituted with one or more fluorine atoms, hydroxyl or $C_1$-$C_8$alkoxy; and the aryl portion of an $R^4$ group may be optionally substituted with $C_1$-$C_8$alkyl, $C_1$-$C_8$alkoxy or halogen. In one aspect of the invention $R^3$ is $OR^4$ in at least one occurrence wherein $R^4$ is selected from $C_1$-$C_8$alkyl, $C_3$-$C_7$cycloalkyl, and $C_6$-$C_9$polycycloalkyl. In another embodiment, A is a direct bond; p is 1, 2, or 3; and in at least one occurrence, $R^3$ is $OR^4$ wherein $R^4$ is selected from $C_1$-$C_8$alkyl, $C_3$-$C_7$cycloalkyl, and $C_6$-$C_9$polycycloalkyl. In another embodiment, the benzylated ROLIPRAM™ or analog thereof has the formula:

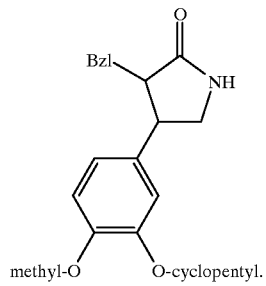

In a different aspect, the PDE4 inhibitor undergoing the benzylation reaction of the present invention is ARIFLO™ or an analog thereof. In one embodiment, the benzylated ARIFLO™ or analog thereof produced the present invention has the formula

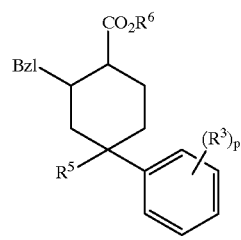

and isolated stereoisomers, salts and solvates thereof, wherein Bzl is a benzyl group; p is 5; and $R^3$ at each occurrence is independently selected from halogen, nitro, $R^4$, $NR^2_{(q)}$, and $OR^4$ wherein q=0, 1, 2, or 3 and $R^4$ at each occurrence is independently selected from H, $C_1$-$C_8$alkyl, alkoxyalkyl having 3–7 carbons in the alkoxy portion and 2–4 carbons in the alkyl portion, phenoxyalkyl having 2–6 carbons in the alkyl portion, $C_3$-$C_7$cycloalkyl, $C_6$-$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$-$C_4$alkyl and indanyl; wherein the alkyl portion of an $R^4$ group may be optionally substituted with one or more fluorine atoms, hydroxyl or $C_1$-$C_8$alkoxy; and the aryl portion of an $R^4$ group may be optionally substituted with $C_1$-$C_8$alkyl, $C_1$-$C_8$alkoxy or halogen; $R^6$ is selected from H, positively charged species, and $C_1$-$C_8$alkyl; and $R^5$ is selected from H, halogen, nitro, cyano, $C_1$-$C_8$alkyl, and $C_1$-$C_8$alkoxy. In one aspect of the invention $R^3$ is $OR^4$ in at least one occurrence wherein $R^4$ is selected from $C_1$-$C_8$alkyl, $C_3$-$C_7$cycloalkyl, and $C_6$-$C_9$polycycloalkyl; $R^6$ is selected from H, positively charged species, and $C_1$-$C_8$alkyl; and $R^5$ is selected from H, halogen, nitro, cyano, $C_1$-$C_8$alkyl, and $C_1$-$C_8$alkoxy. In one embodiment, p is 1, 2 or 3; and in at least one occurrence, $R^3$ is $OR^4$ wherein $R^4$ is selected from $C_1$-$C_8$alkyl, $C_3$-$C_7$cycloalkyl, and $C_5$-$C_9$bicycloalkyl, $R^6$ is selected from H and positively charged species; and $R^5$ is selected from H, halogen, nitro, cyano, $C_1$-$C_3$alkyl, and $C_1$-$C_3$alkoxy. In another embodiment, the benzylated ARIFLO™ or analog thereof has the formula

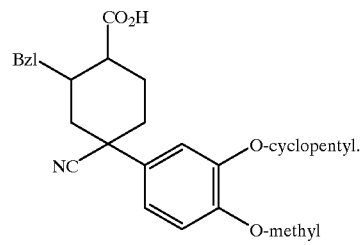

In another embodiment, the benzylated ARIFLO™ or analog thereof has the formula

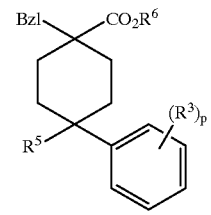

and isolated stereoisomers, salts and solvates thereof, wherein Bzl is a benzyl group; p is 5; and $R^3$ at each occurrence is independently selected from halogen, nitro, $R^4$, $NR^2_{(q)}$, and $OR^4$ wherein q=0, 1, 2, or 3 and $R^4$ at each occurrence is independently selected from H, $C_1$-$C_8$alkyl, alkoxyalkyl having 3–7 carbons in the alkoxy portion and 2–4 carbons in the alkyl portion, phenoxyalkyl having 2–6 carbons in the alkyl portion, $C_3$-$C_7$cycloalkyl, $C_6$-$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^4$ group may be optionally substituted with one or more fluorine atoms, hydroxyl or $C_1$–$C_8$alkoxy; and the aryl portion of an $R^4$ group may be optionally substituted with $C_1$–$C_8$alkyl, $C_1$–$C_8$alkoxy or halogen. In one embodiment, p is 1, 2 or 3; and in at least one occurrence, $R^3$ is $OR^4$ wherein $R^4$ is selected from $C_1$–$C_8$alkyl, $C_3$–$C_7$cycloalkyl, and $C_6$–$C_9$polycycloalkyl, $R^6$ is selected from H and positively charged species; and $R^5$ is selected from H, halogen, cyano, $C_1$–$C_3$alkyl, and $C_1$–$C_3$alkoxy. In one embodiment, the benzylated ARIFLO™ or analog thereof has the formula

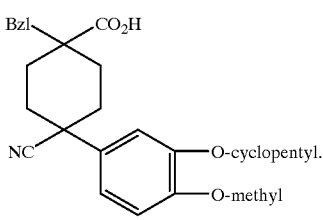

N-Benzylation of PDE4 Inhibitors

In one aspect of the invention, the benzylation may provide a benzyl group attached to a nitrogen atom of the PDE4 inhibitor. In a preferred embodiment of this aspect of the invention, the benzyl group has the following definition:

A benzyl group (Bzl) of the formula

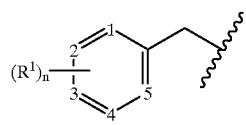

wherein each of the numerals 1, 2, 3, 4 and 5 may be carbon or nitrogen, with the proviso that the ring is aromatic and contains at least 3 carbon atoms; n is 5 and $R^1$ at each occurrence is independently selected from halogen, nitro, $R^2$, $NR^2_{(m)}$, and $OR^2$ wherein m=0, 1, 2, or 3 and $R^2$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^2$ group may be optionally substituted with one or more fluorine atoms, hydroxyl or $C_1$–$C_8$alkoxy; and the aryl portion of an $R^2$ group may be optionally substituted with $C_1$–$C_8$alkyl, $C_1$–$C_8$alkoxy or halogen; with the proviso that either (a) at least one $R^1$ is $OR^2$, or (b) the benzyl ring contains at least two $R^1$ groups that are not hydrogen.

A benzyl group (Bzl) of the formula

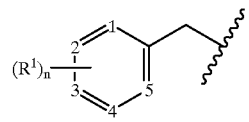

wherein each of the numerals 1, 2, 3, 4 and 5 is carbon, n is 5 and $R^1$ at each occurrence is independently selected from halogen, nitro, $R^2$, $NR^2_{(m)}$, and $OR^2$ wherein m=0, 1, 2, or 3 and $R^2$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^2$ group may be optionally substituted with one or more fluorine atoms, hydroxyl or $C_1$–$C_8$alkoxy; and the aryl portion of an $R^2$ group may be optionally substituted with $C_1$–$C_8$alkyl, $C_1$–$C_8$alkoxy or halogen.

A benzyl group (Bzl) of the formula

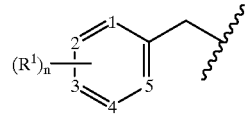

n is 5 and $R^1$ at each occurrence is independently selected from halogen, nitro, $R^2$, $NR^2_{(m)}$, and $OR^2$ wherein m=0, 1, 2, or 3 and $R^2$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, phenyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^2$ group may be optionally substituted with one or more fluorine atoms, hydroxyl or $C_1$–$C_8$alkoxy; and the phenyl portion of an $R^2$ group may be optionally substituted with $C_1$–$C_8$alkyl, $C_1$–$C_8$alkoxy or halogen.

In another aspect, the benzylated PDE4 inhibitor comprises at least one benzyl group (Bzl) of the formula

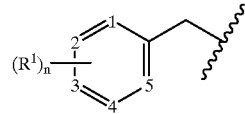

wherein each of the numerals 1, 2, 3, 4 and 5 may be carbon or nitrogen, with the proviso that the ring is aromatic and contains at least 3 carbon atoms; n is 5 and $R^1$ at each occurrence is independently selected from halogen, nitro, $R^2$, $NR^2_{(m)}$, and $OR^2$ wherein m=0, 1, 2, or 3 and $R^2$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^2$ group may be optionally substituted with one or more fluorine atoms, hydroxyl or $C_1$–$C_8$alkoxy; and the aryl portion of an $R^2$ group may be optionally substituted with $C_1$–$C_8$alkyl, $C_1$–$C_8$alkoxy or halogen; with the proviso that either (a) at least one $R^1$ is $OR^2$, or (b) the benzyl ring contains at least two $R^1$ groups that are not hydrogen.

In another aspect, the benzylated PDE4 inhibitor comprises at least one benzyl group (Bzl) of the formula

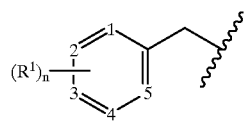

wherein each of the numerals 1, 2, 3, 4 and 5 is carbon; n is 5 and $R^1$ at each occurrence is independently selected from halogen, nitro, $R^2$, $NR^2_{(m)}$, and $OR^2$ wherein m=0, 1, 2, or 3 and $R^2$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^2$ group may be optionally substituted with one or more fluorine atoms, hydroxyl or $C_1$–$C_8$alkoxy; and the aryl portion of an $R^2$ group may be optionally substituted with $C_1$–$C_8$alkyl, $C_1$–$C_8$alkoxy or halogen; with the proviso that $R_1$ is hydrogen at either 1, 2, or 3 occurrences of n, but not 4 or 5 occurrences.

In another aspect, the benzylated PDE4 inhibitor comprises at least one benzyl group (Bzl) of the formula

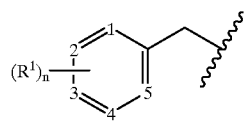

wherein each of the numerals 1, 2, 3, 4 and 5 may be carbon or nitrogen, with the proviso that the ring is aromatic and contains at least 3 carbon atoms; n is 5 and $R^1$ at each occurrence is independently selected from halogen and $OR^2$ wherein $R^2$ at each occurrence is independently selected from H and $C_1$–$C_8$alkyl; with the provisos that the benzyl ring contain no more than three hydrogen substituents and no more than one methoxy substituent.

In one aspect of the present invention where benzylation provides an N-benzylated PDE4 inhibitor, the PDE4 inhibitor is ROLIPRAM™ or analog thereof and the N-benzylated ROLIPRAM™ has the formula:

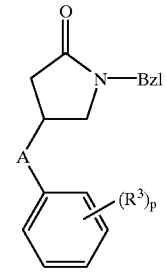

and isolated stereoisomers, salts and solvates thereof, wherein Bzl is a benzyl group; A is selected from a direct bond, optionally substituted $C_1$ -$C_5$alkylene, optionally substituted $C_2$–$C_5$alkenyl and optionally substituted phenylene; p is 5; and $R^3$ at each occurrence is independently selected from halogen, nitro, $R^4$, $NR^4_{(q)}$, and $OR^4$ wherein q=0, 1, 2, or 3 and $R^4$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^4$ group may be optionally substituted with one or more fluorine atoms, hydroxyl or $C_1$–$C_8$alkoxy; and the aryl portion of an $R^4$ group may be optionally substituted with $C_1$–$C_8$alkyl, $C_1$–$C_8$alkoxy or halogen. In one embodiment, A is a direct bond; p is 1, 2, or 3; and in at least one occurrence, $R^3$ is $OR^4$ wherein $R^4$ is selected from $C_1$–$C_8$alkyl, $C_3$–$C_7$cycloalkyl, and $C_6$–$C_9$polycycloalkyl. In one embodiment, benzylated ROLIPRAM™ or analog thereof has the formula

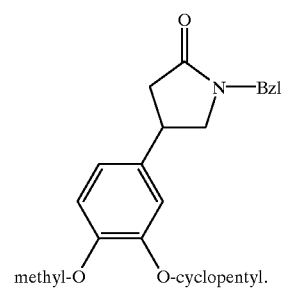

methyl-O    O-cyclopentyl.

In one aspect of the present invention where benzylation provides an N-benzylated PDE4 inhibitor, the PDE4 inhibitor is WAY-PDA-641 or an analog thereof. See, e.g., U.S. Pat. No. 5,124,455. In one embodiment, the benzylated WAY-PDA-641 or analog thereof has the formula:

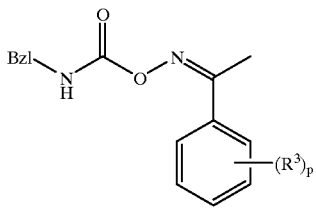

and isolated stereoisomers, salts and solvates thereof, wherein Bzl is a benzyl group; p is 5; and $R^3$ at each occurrence is independently selected from halogen, nitro, $R^4$, $NR^2_{(q)}$, and $OR^4$ wherein q=0, 1, 2, or 3 and $R^4$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^4$ group may be optionally substituted with one or more fluorine atoms, hydroxyl or $C_1$–$C_8$alkoxy; and the aryl portion of an $R^4$ group may be optionally substituted with $C_1$–$C_8$alkyl, $C_1$–$C_8$alkoxy or halogen. In one embodiment, p is 1, 2 or 3; and in at least one occurrence, $R^3$ is $OR^4$ wherein $R^4$ is selected from $C_1$–$C_8$alkyl, $C_3$–$C_7$cycloalkyl, and $C_6$–$C_9$polycycloalkyl. In another embodiment, the benzylated WAY-PDA-641 or analog thereof has the formula:

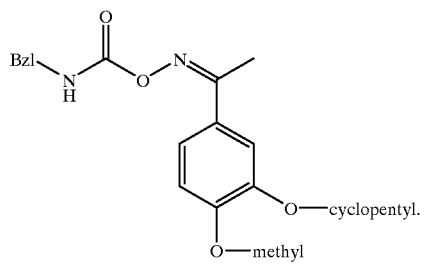

In one aspect of the present invention where benzylation provides an N-benzylated PDE4 inhibitor, the PDE4 inhibitor is Ro-20-1724 or an analog thereof. See, e.g., U.S. Pat. Nos. 3,636,039 and 4,308,278. In one embodiment, the benzylated Ro-20-1724 or analog thereof has the formula:

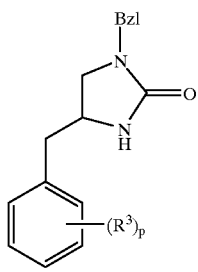

and isolated stereoisomers, salts and solvates thereof, wherein Bzl is a benzyl group; p is 5; and $R^3$ at each occurrence is independently selected from halogen, nitro, $R^4$, $NR^4_{(q)}$, and $OR^4$ wherein q=0, 1, 2, or 3 and $R^4$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^4$ group may be optionally substituted with one or more fluorine atoms, hydroxyl or $C_1$–$C_8$alkoxy; and the aryl portion of an $R^4$ group may be optionally substituted with $C_1$–$C_8$alkyl, $C_1$–$C_8$alkoxy or halogen. In one embodiment, p is 1, 2 or 3; and in at least one occurrence, $R^3$ is $OR^4$ wherein $R^4$ is selected from $C_1$–$C_8$alkyl, $C_3$–$C_7$cycloalkyl, and $C_5$–$C_9$bicycloalkyl. In one embodiment, the benzylated Ro-20-1724 or analog thereof has the formula:

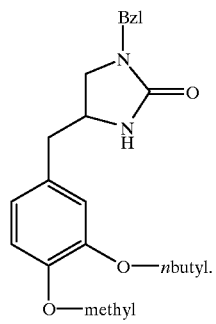

In another embodiment, the benzylated Ro-20-1724 or analog thereof has the formula:

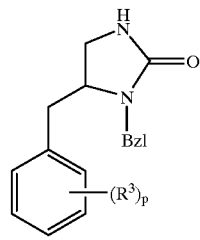

and isolated stereoisomers, salts and solvates thereof, wherein Bzl is a benzyl group; p is 5; and $R^3$ at each occurrence is independently selected from halogen, nitro, $R^4$, $NR^2_{(q)}$, and $OR^4$ wherein q=0, 1, 2, or 3 and $R^4$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^4$ group may be optionally substituted with one or more fluorine atoms, hydroxyl or $C_1$–$C_8$alkoxy; and the aryl portion of an $R^4$ group may be optionally substituted with $C_1$–$C_8$alkyl, $C_1$–$C_8$alkoxy or halogen. In one embodiment, p is 1, 2 or 3; and in at least one occurrence, $R^3$ is $OR^4$ wherein $R^4$ is selected from $C_1$–$C_8$alkyl, $C_3$–$C_7$cycloalkyl, and $C_6$–$C_9$polycycloalkyl. In another embodiment, the benzylated Ro-20-1724 or analog thereof has the formula:

In one aspect of the present invention where benzylation provides an N-benzylated PDE4 inhibitor, the PDE4 inhibitor is RP 73401 or an analog thereof. See, e.g., PCT International Publication No. 92/12961; Organic Process Research & Development 1998, 2, 157–168; and *J. Med. Chem.* 1994, 37, 1696–1703. In one embodiment, the benzylated RP 73401 or analog thereof has the formula:

and isolated stereoisomers, salts and solvates thereof, wherein Bzl is a benzyl group; p is 5; and $R^3$ at each occurrence is independently selected from halogen, nitro, $R^4$, $NR^2_{(q)}$, and $OR^4$ wherein q=0, 1, 2, or 3 and $R^4$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^4$ group may be optionally substituted with one or more fluorine atoms, hydroxyl or $C_1$–$C_8$alkoxy; and the aryl portion of an $R^4$ group may be optionally substituted with $C_1$–$C_8$alkyl, $C_1$–$C_8$alkoxy or halogen. In one embodiment, p is 1, 2 or 3; and in at least one occurrence, $R^3$ is $OR^4$ wherein $R^4$ is selected from $C_1$–$C_8$alkyl, $C_3$–$C_7$cycloalkyl, and $C_6$–$C_9$polycycloalkyl. In another embodiment, the benzylated RP 73401 or analog thereof has the formula:

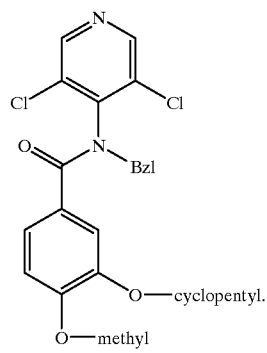

In one aspect of the present invention where benzylation provides an N-benzylated PDE4 inhibitor, the PDE4 inhibitor is CP-80,633-A or an analog thereof. See, e.g., U.S. Pat. No. 5,814,651. In one embodiment, the benzylated CP-80,633-A or analog thereof has the formula:

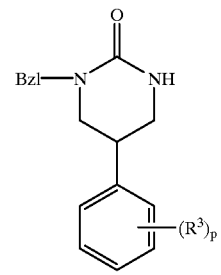

and isolated stereoisomers, salts and solvates thereof, wherein Bzl is a benzyl group; p is 5; and $R^3$ at each occurrence is independently selected from halogen, nitro, $R^4$, $NR^4_{(q)}$, and $OR^4$ wherein q=0, 1, 2, or 3 and $R^4$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^4$ group may be optionally substituted with one or more fluorine atoms, hydroxyl or $C_1$–$C_8$alkoxy; and the aryl portion of an $R^4$ group may be optionally substituted with $C_1$–$C_8$alkyl, $C_1$–$C_8$alkoxy or halogen. In one embodiment, p is 1, 2 or 3; and in at least one occurrence, $R^3$ is $OR^4$ wherein $R^4$ is selected from $C_1$–$C_8$alkyl, $C_3$–$C_7$cycloalkyl, and $C_6$–$C_9$polycycloalkyl. In one embodiment, the benzylated CP-80,633-A or analog thereof has the formula:

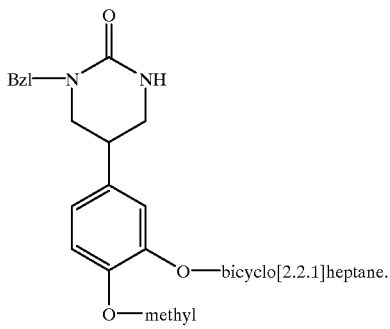

A benzylated compound as disclosed herein includes stereoisomers in admixture and isolated form. Shown below are two stereoisomers of benzylated CP-80,633-A according to the invention.

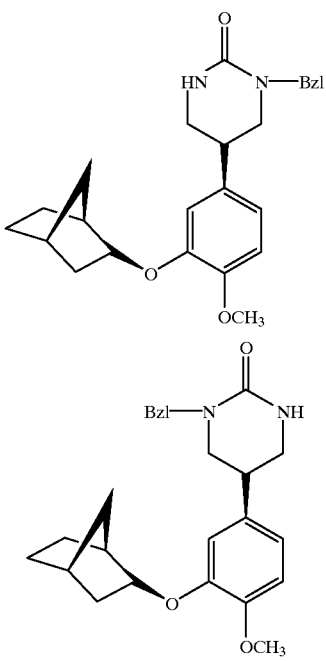

In one aspect of the present invention where benzylation provides an N-benzylated PDE4 inhibitor, the PDE4 inhibitor is AROFYLLINE™ or an analog thereof. In one embodiment, the benzylated AROFYLLINE™ or analog thereof has the formulae:

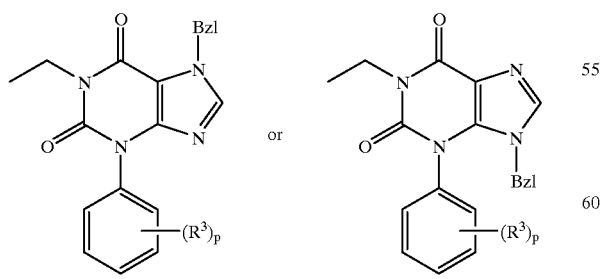

and isolated stereoisomers, salts and solvates thereof, wherein Bzl is a benzyl group; p is 5; and $R^3$ at each occurrence is independently selected from halogen, nitro, $R^4$, $NR^2_{(q)}$, and $OR^4$ wherein q=0, 1, 2, or 3 and $R^4$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^4$ group may be optionally substituted with one or more fluorine atoms, hydroxyl or $C_1$–$C_8$alkoxy; and the aryl portion of an $R^4$ group may be optionally substituted with $C_1$–$C_8$alkyl, $C_1$–$C_8$alkoxy or halogen. In one embodiment, p is 1, 2 or 3; and in at least one occurrence, $R^3$ is halogen or $OR^4$ wherein $R^4$ is selected from $C_1$–$C_8$alkyl, $C_3$–$C_7$cycloalkyl, and $C_6$–$C_9$polycycloalkyl. In one embodiment, the benzylated AROFYLLINE™ or analog thereof has the formula:

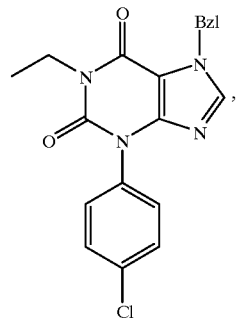

while in another embodiment, the benzylated AROFYLLINE™ or analog thereof has the formula:

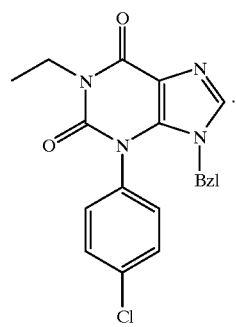

In one aspect of the present invention where benzylation provides an N-benzylated PDE4 inhibitor, the PDE4 inhibitor is CIPAMFYLLINE™ or an analog thereof. In one embodiment, the benzylated CIPAMFYLLINE™ or analog thereof is selected from the formulae:

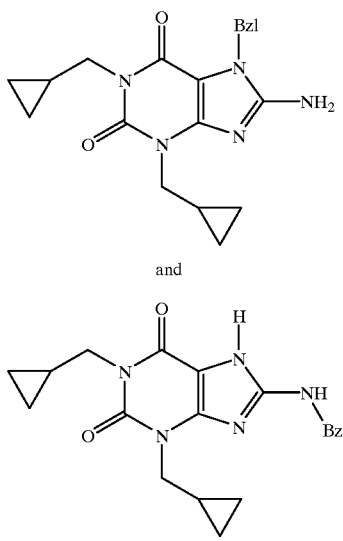

and and isolated stereoisomers, salts and solvates thereof, wherein Bzl is a benzyl group.

Benzylated PDE4 Inhibitors

In various aspects, the present invention provides the following specific benzylated PDE4 inhibitors.

A C-benzylated ROLIPRAM™ or analog thereof compound of the formula

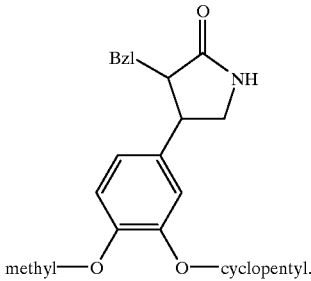

and isolated stereoisomers, salts and solvates thereof, wherein Bzl is a benzyl group; A is selected from a direct bond, optionally substituted $C_1$–$C_5$alkylene, optionally substituted $C_2$–$C_5$alkenyl and optionally substituted phenylene; p is 5; and $R^3$ at each occurrence is independently selected from halogen, nitro, $R^4$, $NR^2_{(q)}$, and $OR^4$ wherein q=0, 1, 2, or 3 and $R^4$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an R group may be optionally substituted with one or more fluorine atoms, hydroxyl or $C_1$–$C_8$alkoxy; and the aryl portion of an $R^4$ group may be optionally substituted with $C_1$–$C_8$alkyl, $C_1$–$C_8$alkoxy or halogen. In a further embodiment, A is a direct bond; p is 1, 2, or 3; and in at least one occurrence, $R^3$ is $OR^4$ wherein $R^4$ is selected from $C_1$–$C_8$alkyl, $C_3$–$C_7$cycloalkyl, and $C_6$–$C_9$polycycloalkyl. In a preferred embodiment, $R^3$ at the para position relative to A is alkoxy, and $R^3$ at one meta position is selected from alkyl having at least 3 carbons and alkoxy having at least 3 carbons. In a further embodiment, the benzylated PDE4 inhibitor has the formula:

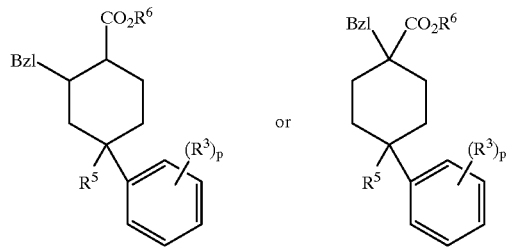

A benzylated ARIFLO™ or analog thereof compound of the formulae

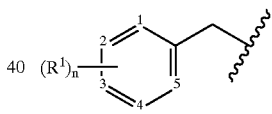

and isolated stereoisomers, salts and solvates thereof, wherein Bzl is a benzyl group of the formula $(R^1)_n$— wherein each of the numerals 1, 2, 3, 4 and 5 may be carbon or nitrogen, with the proviso that the ring is aromatic and contains at least 3 carbon atoms; n is 5 and $R^1$ at each occurrence is independently selected from halogen, nitro, $R^2$, $NR^2_{(m)}$, and $OR^2$ wherein m=0, 1, 2, or 3 and $R^2$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^2$ group may be optionally substituted with one or more fluorine atoms, hydroxyl or $C_1$–$C_8$alkoxy; and the aryl portion of an $R^2$ group may be optionally substituted with $C_1$–$C_8$alkyl, $C_1$–$C_8$alkoxy or halogen; p is 5; and $R^3$ at each occurrence is independently selected from halogen, nitro, $R^4$, $NR^2_{(q)}$, and $OR^4$ wherein q=0, 1, 2, or 3 and $R^4$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^4$ group may be optionally substituted with one or more fluorine atoms, hydroxyl or $C_1$–$C_8$alkoxy; and the aryl portion of an $R^4$ group may be optionally substituted with $C_1$–$C_8$alkyl, $C_1$–$C_8$alkoxy or halogen; $R^5$ is selected from H, halogen, cyano, $C_1$–$C_8$alkyl, and $C_1$–$C_8$alkoxy; and $R^6$ is selected from H, positively charged species, and $C_1$–$C_8$alkyl. Optionally, in at least one occurrence, $R^3$ is $OR^4$ wherein $R^4$ is selected from $C_1$–$C_8$alkyl, $C_3$–$C_7$cycloalkyl, and $C_5$–$C_9$bicycloalkyl; and $R^6$ is selected from H and positively charged species.

In one aspect, the benzylated ARIFLO™ or analog thereof compound has a formula,

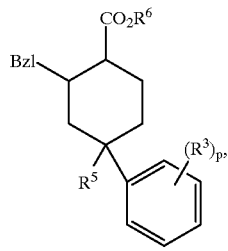

In another aspect, the benzylated ARIFLO™ or analog thereof compound has a formula,

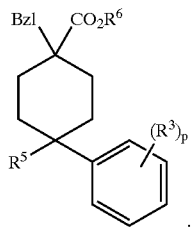

In another aspect, the benzylated ARIFLO™ or analog thereof compound has a formula,

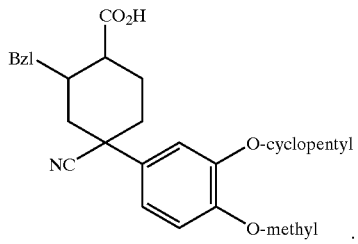

In another aspect, the benzylated ARIFLO™ or analog thereof compound has a formula,

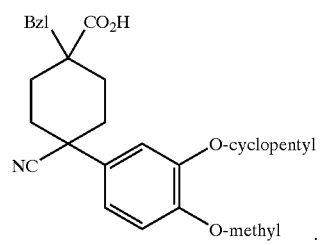

In other embodiments, the benzylated ARIFLO™ or analog thereof compound has specific stereochemistry. Certain specific stereochemistries are shown below:

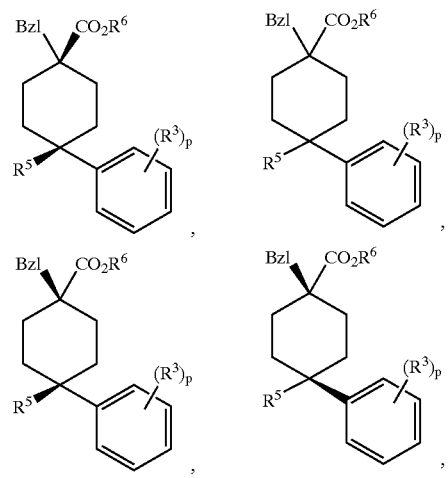

In another aspect, the present invention provides an N-benzylated ROLIPRAM™ or analog thereof compound of the formula

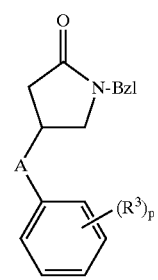

and isolated stereoisomers, salts and solvates thereof, wherein

Bzl is a benzyl group of the formula

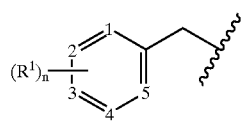

wherein each of the numerals 1, 2, 3, 4 and 5 may be carbon or nitrogen, with the proviso that the ring is aromatic and contains at least 3 carbon atoms;

n is 5 and $R^1$ at each occurrence is independently selected from halogen, nitro, $R^2$, $NR^2_{(m)}$, and $OR^2$ wherein m=0, 1, 2, or 3 and $R^2$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^2$ group may be optionally substituted with one or more fluorine atoms, hydroxyl or $C_1$–$C_8$alkoxy; and the aryl portion of an $R^2$ group may be optionally substituted with $C_1$–$C_8$alkyl, $C_1$–$C_8$alkoxy or halogen;

A is selected from a direct bond, optionally substituted $C_1$–$C_5$alkylene, optionally substituted $C_2$–$C_5$alkenyl and optionally substituted phenylene;

p is 5 and $R^3$ at each occurrence is independently selected from halogen, nitro, $R^4$, $NR^2_{(q)}$, and $OR^4$ wherein q=0, 1, 2, or 3 and $R^4$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^4$ group may be optionally substituted with one or more fluorine atoms, hydroxyl or $C_1$–$C_8$alkoxy; and the aryl portion of an $R^4$ group may be optionally substituted with $C_1$–$C_8$alkyl, $C_1$–$C_8$alkoxy or halogen; with the provisos that, at the meta position relative to the A group on the $R^3$-substituted phenyl ring, $R^3$ is alkoxy having at least three carbon atoms, excluding cyclopentyloxy, and at the para position $R^1$ is not hydrogen.

In a different aspect, the present invention provides an N-benzylated ROLIPRAM™ or analog thereof compound of the formula

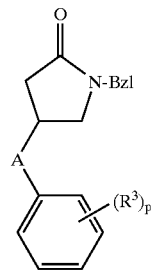

and isolated stereoisomers, salts and solvates thereof, wherein

Bzl is a benzyl group of the formula

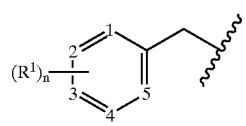

wherein each of the numerals 1, 2, 3, 4 and 5 may be carbon or nitrogen, with the proviso that the ring is aromatic and contains at least 3 carbon atoms;

n is 5 and $R^1$ at each occurrence is independently selected from halogen and $OR^2$ wherein $R^2$ at each occurrence is independently selected from H and $C_1$–$C_8$alkyl; with the provisos that the benzyl ring contain no more than three hydrogen substituents and no more than one methoxy substituent;

A is selected from a direct bond, optionally substituted $C_1$-C5alkylene, optionally substituted $C_2$–$C_5$alkenyl and optionally substituted phenylene;

p is 5 and $R^3$ at each occurrence is independently selected from halogen, nitro, $R^4$, $NR^2_{(q)}$, and $OR^4$ wherein q=0, 1, 2, or 3 and $R^4$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^4$ group may be optionally substituted with one or more fluorine atoms, hydroxyl or $C_1$–$C_8$alkoxy; and the aryl portion of an $R^4$ group may be optionally substituted with $C_1$–$C_8$alkyl, $C_1$–$C_8$alkoxy or halogen.

In a further embodiment, the PDE4 inhibitor is an N-benzylated PDE4 inhibitor having the formula

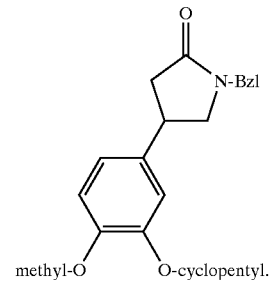

In another aspect, the present invention provides an N-benzylated WAY-PDA-641 or analog thereof compound of the formula:

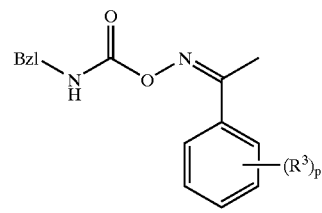

and isolated stereoisomers, salts and solvates thereof, wherein Bzl is a benzyl group; and $(R^3)_p$ is as defined herein. Optionally, p is 1, 2 or 3; and in at least one occurrence, $R^3$ is $OR^4$ wherein $R^4$ is selected from $C_1$–$C_8$alkyl, $C_3$–$C_7$cycloalkyl, and $C_6$–$C_9$polycycloalkyl. In a further embodiment, the PDE4 inhibitor is an N-benzylated PDE4 inhibitor having the formula

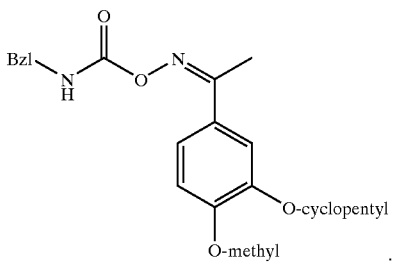

In another aspect, the present invention provides an N-benzylated Ro-20-1724 or analog thereof compound of the formulae:

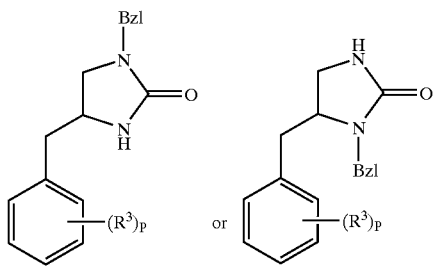

and isolated stereoisomers, salts and solvates thereof, wherein Bzl is a benzyl group; p is 5; and $R^3$ at each occurrence is independently selected from halogen, nitro, $R^4$, $NR^2_{(q)}$, and $OR^4$ wherein q=0, 1, 2, or 3 and $R^4$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^4$ group may be optionally substituted with one or more fluorine atoms, hydroxyl or $C_1$–$C_8$alkoxy; and the aryl portion of an $R^4$ group may be optionally substituted with $C_1$–$C_8$alkyl, $C_1$–$C_8$alkoxy or halogen. In a preferred embodiment, relative to the methylene bridge to the heterocyclic ring, $R^3$ at the para position is alkoxy, and $R^3$ at a meta position is alkoxy having at least three carbon atoms. Optionally, p is 1, 2 or 3; and in at least one occurrence, $R^3$ is $OR^4$ wherein $R^4$ is selected from $C_1$–$C_8$alkyl, $C_3$–$C_7$cycloalkyl, and $C_5$–$C_9$bicycloalkyl. In another embodiment the invention provides an N-benzylated Ro-20-1724 or analog thereof compound having the formula

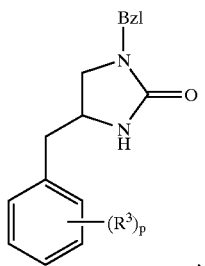

while in another embodiment the invention provides an N-benzylated Ro-20-1724 or analog thereof compound having the formula

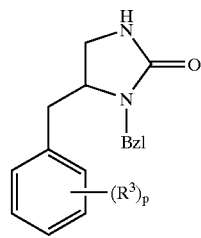

while in another embodiment the invention provides an N-benzylated Ro-20-1724 or analog thereof compound having the formula

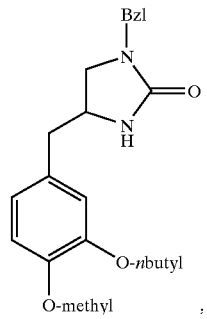

while in another embodiment the invention provides an N-benzylated Ro-20-1724 or analog thereof compound having the formula

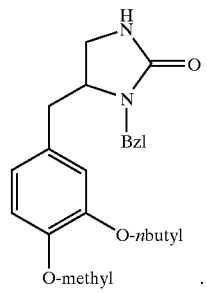

In another aspect, the present invention provides an N-benzylated RP 73401 or analog thereof compound of the formula:

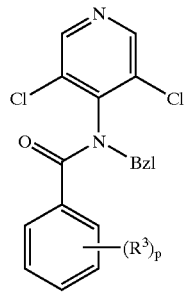

and isolated stereoisomers, salts and solvates thereof, wherein Bzl is a benzyl group; and $(R^3)_p$ is as defined herein. Optionally, p is 1, 2 or 3; and in at least one occurrence, $R^3$ is $OR^4$ wherein $R^4$ is selected from $C_1$–$C_8$alkyl, $C_3$–$C_7$cycloalkyl, and $C_6$–$C_9$polycycloalkyl. In one embodiment, the N-benzylated RP 73401 or analog thereof compound has the formula:

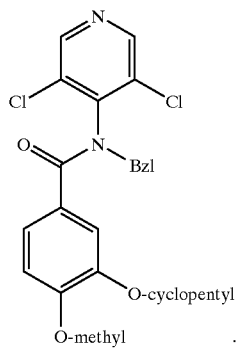

In another aspect, the present invention provides an N-benzylated CP-80,633-A or analog thereof compound of the formulae:

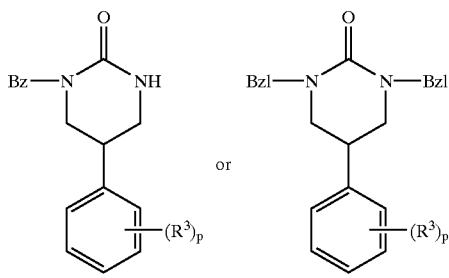

and isolated stereoisomers, salts and solvates thereof, wherein Bzl is a benzyl group; p is 5; and $R^3$ at each occurrence is independently selected from nitro, $R^4$, $NR^2_{(q)}$, and $OR^4$ wherein q=0, 1, 2, or 3 and $R^4$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an $R^4$ group may be optionally substituted with one or more fluorine atoms, hydroxyl or $C_1$–$C_8$alkoxy; and the aryl portion of an $R^4$ group may be optionally substituted with $C_1$–$C_8$alkyl, $C_1$–$C_8$alkoxy or halogen. In a preferred embodiment, not more than 4 of the $R^3$ groups are hydrogen. Optionally, p is 1, 2 or 3; and in at least one occurrence, $R^3$ is $OR^4$ wherein $R^4$ is selected from $C_1$–$C_8$alkyl, $C_3$–$C_7$cycloalkyl, and $C_6$–$C_9$polycycloalkyl. In one embodiment, the N-benzylated In one embodiment the N-benzylated CP-80,633-A or analog thereof compound has the formula:

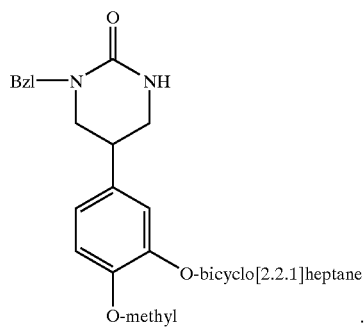

In another aspect, the present invention provides an N-benzylated AROFYLLINE™ or analog thereof of the formula:

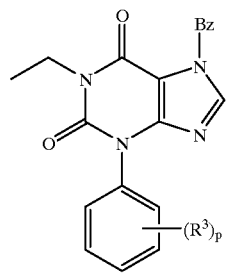

and isolated stereoisomers, salts and solvates thereof, wherein Bzl is a benzyl group; and $(R^3)^p$ is as defined above. Optionally, p is 1, 2 or 3; and in at least one occurrence, $R^3$ is halogen or $OR^4$ wherein $R^4$ is selected from $C_1$–$C_8$alkyl, $C_3$–$C_7$cycloalkyl, and $C_6$–$C_9$polycycloalkyl. In another embodiment, the N-benzylated AROFYLLINE™ or analog thereof has the formula

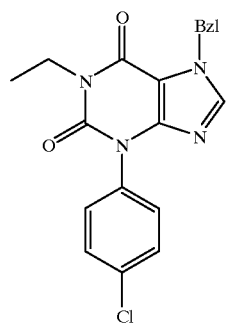

while in another embodiment the N-benzylated AROFYLLINE or analog thereof has the formula

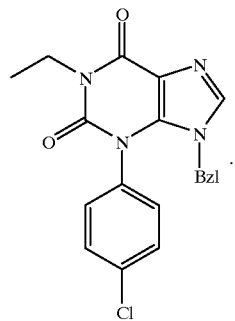

In another aspect, the present invention provides an N-benzylated CIPAMFYLLINE™ or analog thereof compound of the formula

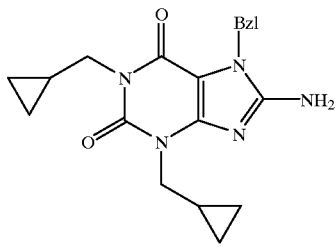

and isolated stereoisomers, salts and solvates thereof, wherein Bzl is a benzyl group.

Pharmaceutical Compositions

In another embodiment, the present invention provides pharmaceutical compositions containing a benzylated compound of the invention, i.e., a C- or N-benzylated compound as described herein and/or made according to the method of the present invention, in combination with a pharmaceutically-acceptable carrier, diluent or excipient. These compositions may be used for the treatment of inflammation or other conditions as disclosed herein. These compositions may also be formed into a medicament, which may used in the treatment of, for example, inflammation.

In addition, these compositions are useful as, for example, assay standards, convenient means of making bulk shipments, or pharmaceutical compositions. An assayable amount of a compound of the invention is an amount which is readily measurable by standard assay procedures and techniques as are well known and appreciated by those skilled in the art. Assayable amounts of a compound of the invention will generally vary from about 0.001 wt % to about 98 wt % of the entire weight of the composition. Inert carriers include any material which does not degrade or otherwise covalently react with a compound of the present invention. Examples of suitable inert carriers are water; aqueous buffers, such as those which are generally useful in High Performance Liquid Chromatography (HPLC) analysis; organic solvents, such as acetonitrile, ethyl acetate, hexane and the like; and pharmaceutically acceptable carriers.

"Pharmaceutically acceptable carriers" for therapeutic use are well known in the pharmaceutical art, and are described, for example, in Remingtons Pharmaceutical Sciences, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id.

Thus, the present invention provides a pharmaceutical or veterinary composition (hereinafter, simply referred to as a pharmaceutical composition) containing a benzylated compound of the invention as described above, in admixture with a pharmaceutically acceptable carrier. The invention further provides a composition, preferably a pharmaceutical composition, containing an effective amount of a compound of the present invention, as described above, in association with a pharmaceutically acceptable carrier.

The pharmaceutical compositions of the present invention may be in any form which allows for the composition to be administered to a patient. For example, the composition may be in the form of a solid, liquid or gas (aerosol). Typical routes of administration include, without limitation, oral, topical, parenteral, sublingual, rectal, vaginal, intranasal, and inhalation. The term parenteral as used herein includes subcutaneous injections, intravenous, intramuscular, intrastemal injection or infusion techniques. Pharmaceutical composition of the invention are formulated so as to allow the active ingredients contained therein to be bioavailable upon administration of the composition to a patient. Compositions that will be administered to a patient take the form of one or more dosage units, where for example, a tablet may be a single dosage unit, and a container of a compound of the present invention in aerosol form may hold a plurality of dosage units.

Materials used in preparing the pharmaceutical compositions should be pharmaceutically pure and non-toxic in the amounts used. It will be evident to those of ordinary skill in the art that the optimal dosage of the active ingredient(s) in the pharmaceutical composition will depend on a variety of factors. Relevant factors include, without limitation, the type of subject (e.g., human), the particular form of the active ingredient, the manner of administration and the composition employed.

In general, the pharmaceutical composition includes a benzylated compound as described herein, in admixture with one or more carriers. The carrier(s) may be particulate, so that the compositions are, for example, in tablet or powder form. The carrier(s) may be liquid, with the compositions being, for example, an oral syrup or injectable liquid. In addition, the carrier(s) may be gaseous, so as to provide an aerosol composition useful in, e.g., inhalatory administration.

When intended for oral administration, the composition is preferably in either solid or liquid form, where semi-solid, semi-liquid, suspension and gel forms are included within the forms considered herein as either solid or liquid.

As a solid composition for oral administration, the composition may be formulated into a powder, granule, compressed tablet, pill, capsule, chewing gum, wafer or the like form. Such a solid composition will typically contain one or more inert diluents or edible carriers. In addition, one or more of the following adjuvants may be present: binders such as carboxymethylcellulose, ethyl cellulose, microcrystalline cellulose, or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent.

When the composition is in the form of a capsule, e.g., a gelatin capsule, it may contain, in addition to materials of the above type, a liquid carrier such as polyethylene glycol, cyclodextrin or a fatty oil.

The composition may be in the form of a liquid, e.g., an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or digylcerides which may serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid composition intended for either parenteral or oral administration should contain an amount of a compound of the present invention such that a suitable dosage will be obtained. Typically, this amount is at least 0.01% of a compound of the invention in the composition. When intended for oral administration, this amount may be varied to be between 0.001% and about 97% of the weight of the composition. Preferred oral compositions contain between about 0.1% and about 50% of the active compound of the present invention. Preferred compositions and preparations according to the present invention are prepared so that a parenteral dosage unit contains between 0.1% to 5% by weight of active compound.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, beeswax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of a benzylated compound of the present invention of from about 0.01% to about 10% w/v (weight per unit volume).

The composition may be intended for rectal administration, in the form, e.g., of a suppository which will melt in the rectum and release the drug. The composition for rectal administration may contain an oleaginous base as a suitable nonirritating excipient. Such bases include, without limitation, lanolin, cocoa butter and polyethylene glycol.

The composition may include various materials which modify the physical form of a solid or liquid dosage unit. For example, the composition may include materials that form a coating shell around the active ingredients. The materials which form the coating shell are typically inert, and may be selected from, for example, sugar, shellac, and other enteric coating agents. Alternatively, the active ingredients may be encased in a gelatin capsule.

The composition in solid or liquid form may include an agent which binds to the active component(s) and thereby assists in the delivery of the active components. Suitable agents which may act in this capacity include a monoclonal or polyclonal antibody, a protein or a liposome.

The pharmaceutical composition of the present invention may consist of gaseous dosage units, e.g., it may be in the form of an aerosol. The term aerosol is used to denote a variety of systems ranging from those of colloidal nature to systems consisting of pressurized packages. Delivery may be by a liquefied or compressed gas or by a suitable pump system which dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, spacers and the like, which together may form a kit. Preferred aerosols may be determined by one skilled in the art, without undue experimentation.

Whether in solid, liquid or gaseous form, the pharmaceutical composition of the present invention may contain one or more known pharmacological agents used in the treatment of inflammation (including arthritis).

The pharmaceutical compositions may be prepared by methodology well known in the pharmaceutical art.

A composition intended to be administered by injection can be prepared by combining a benzylated compound as described herein with water so as to form a solution. A surfactant may be added to facilitate the formation of a homogeneous solution or suspension. Surfactants are compounds that non-covalently interact with the benzylated compounds of the invention so as to facilitate dissolution or homogeneous suspension of the active compound in the aqueous delivery system.

In a preferred embodiment, a benzylated PDE4 inhibitor according to the present invention, or a benzylated PDE4 inhibitor prepared according to the present invention, has an $IC_{50}$ of 600 nM (nanomolar) or less, more preferably 400 nM or less.

Methods for Assessment of PDE4 Activity, HARBS Activity and Emetogenic Potential Various in vitro tests, which are well known to one of ordinary skill in the art, may be used to determine whether a particular compound is a PDE inhibitor. Some tests are specific to a particular PDE isozyme or conformer, while other tests are less specific. A few of these tests are described below. The identification of other testing protocols is readily achieved by reviewing the scientific and patent literature, including Burnouf, C. et al. "Phosphodiesterase 4 Inhibitors" *Annual Reports in Medicinal Chemistry*, Vol. 33, Chap. 10, pp 91–109, 1998 (Bristol, J. A., ed.); Essayan, D. M. "Cyclic Nucleotide Phosphodiesterase (PDE) Inhibitors and Immunomodulation" *Biochemical Pharmacology* 57:965–973, 1999; Souness, J. E. and Foster, M. "Potential of phospodiesterase type IV inhibitors in the treatment of rheumatoid arthritis" *Idrugs* 1(5):541–553, 1998; Souness, J. E. et al. "Immunosuppressive and anti-inflammatory effect of cAMP phosphodiesterase (PDE) type 4 inhibitors" *Immunopharmacology* 47: 127–162, 2000; and Torphy, T. J. "Phosphodiesterase Isozymes" *Am J. Respir. Crit. Care Med.* 157:351–370, 1998, as well as the numerous references cited in these articles.

A test compound may be screened for activity against 11 of the major classes of mammalian cyclic nucleotide phosphodiesterase (termed PDE 1 through 11). These PDE's may use cAMP or cGMP or both cyclic nucleotides as substrates. The broad specificity PDE inhibitor 3-isobutyl-1-methylxanthine (IBMX; Sigma; Catalogue No. 17018) or like compound may be used as a positive control in most assays. PDE's for some of the various assays may be fully or partially purified from the following cells/tissues: PDE 1 (bovine heart), PDE 2 (human platelets), PDE 3 (human platelets), PDE4 (human promonocytic U937 cells) and PDE 5 (human platelets).

In the following descriptions, amounts are exemplary, and may be varied. U937 cytoplasmic extracts may be prepared by sonicating U937 cells (ATCC: Catalogue No. CRL-159) in lysis buffer (M-PER mammalian protein extraction reagent, Pierce catalog # 78501 containing 10% Protease Inhibitor Cocktail For Use with Mammalian Cell and Tissue Extracts, Sigma catalog # P8340). Sonicated cell extracts are then centrifuged at 70,000 g for 30 minutes and supernatants removed. Sucrose is added to a final concentration of 0.25 M, then the extracts are aliquoted and stored at −80° C.

PDE reactions are performed using the Phosphodiesterase [$^3$H] cAMP SPA enzyme assay as described by the manufacturer (Amersham Pharmacia Biotech; http://www.apbiotech.com; catalog # 7090). Briefly, the assay is run for 60 minutes at room temperature in 50 μL volumes in 1 μM [$^3$M] cAMP, 50 mM Tris Cl, 10 mM $MgCl_2$ pH 7.5. U937 extract is added such that less than 10% of substrate was consumed. Test compound or vehicle is added to the desired concentration. Typically, compounds are tested at six 10-fold dilutions ranging from 100 µM to 1 nM. Reactions are performed in duplicate. Reactions are terminated with 50 µl of Yttrium SPA beads and then counted on a Packard Scintillation counter (TopCount™) for 1 minute.

Utilizing the PDE assay conditions described above with PDE4, typical PDE4 inhibitors such as ROLIPRAM™ and Ro-20-1724 (Calbiochem: Catalogue No. 557502) give $IC_{50}$ values in agreement with those found in the literature (reviewed in Schudt et al., 1996).

Inhibition of PDE4 (or more accurately, specific isoforms of PDE4) with subsequent elevation of intracellular cAMP and protein kinase A activation is a therapeutic target in inflammatory or autoimmune diseases where the causal cells or tissues involved predominantly express this PDE isoform. With respect to rheumatoid arthritis, the PDE4 inhibitor ROLIPRAM™ has been shown to be active in animal models of the disease such as collagen-induced arthritis in the rat (Nyman et al., *Clin. Exp. Immunol.* 108(3), 415–419, 1997).

Compounds including a benzyl group according to the process of the present invention typically demonstrate PDE4 inhibition with reduced emetogenic potential, relative to the corresponding non benzylated analog. The efficacy of a compound as a PDE4 inhibitor with diminished emetogenic potential may be measured by determining the extent to which the compound displaces ROLIPRAM™ from its preferred binding site (known as the High Affinity Binding Site, or HARBs) on PDE4. Animal models have shown that a compound's antiinflammatory efficacy as a PDE4 inhibitor is highly correlated with its potency at inhibiting PDE4 catalytic activity rather than its ability to displace [$^3$H]-ROLIPRAM™ from a high affinity binding site from cells within the brain and central nervous system (Duplantier 1996, Barnette 1996). Compounds having benzyl groups according to the present invention displayed a low affinity for the HARBS conformer of PDE4 suggesting that these compounds are not likely to be plagued by mechanism-associated side-effects associated with first generation PDE4 inhibitors such as ROLIPRAM™.

In order to perform this assay, female CD1 mice are sacrificed via the intraperitoneal injection of 100 µL ethanol, and the brain tissue is homogenized in 5 mL of ice-cold Tris-HCl, pH 8.00 supplemented with 1.2 mM $MgCl_2$, 1 mM benzamidine (Sigma; Catalogue No. B 6506) and 0.1 mM PMSF (Sigma; Catalogue No. P 7626). The suspension is centrifuged twice at 30,000×G at 4° C. and then the supernatant discarded. The pellet is resuspended in buffer, and adjusted to a protein concentration of 0.5 mg/mL. Compounds to be tested are dissolved in DMSO and pipetted in triplicate into a 96 well microplate at concentrations ranging from 1 to 30,000 nM. 10 mL of membrane preparation is supplemented with 100 µL of 0.235 µM [$^3$H]-ROLIPRAM™ in DMSO, and 100 µL is dispensed into each well of the microplate. The plate is incubated at 4° C. for 1 hour. Contents of the plate are aspirated through a Whatman GF/C filterplate, and rinsed with 4×200 µL ice-cold buffer. The plate is dried overnight, and then 30 µL of Microscint 20 (Packard; Catalogue No. 6013621) is added to each well, and plate is read in the scintillation counter with a sampling time of 2 minutes/well. Values representing non-specific binding (defined by counts obtained using 20 µM ROLIPRAM™) are subtracted from all data points. Triplicate determinations should be performed at each concentration. The PDE4:HARBS value indicates the ratio of the $IC_{50}$ concentration required to inhibit catalytic activity to the concentration required to displace 50% of ROLIPRAM™ from the high affinity binding site.

Under these assay conditions ROLIPRAM™ is able to displace $^3$H-ROLIPRAM™ from a high-affinity binding site in mouse brain with an $IC_{50}$ of about 6 nM (data not shown).

Thus, ROLIPRAM™ binds with 65 fold greater affinity to its high affinity site than the concentration required for half-maximal inhibition of PDE4 catalytic activity. This preferential affinity for HARBS over the catalytic conformer has been correlated with the negative side effects of first generation PDE4 inhibitors; namely emesis and CNS effects.

Benzylated compounds according to the present invention are less potent at binding to this HARBS site than ROLIPRAM™. For example, see the LPDE4:HPDE4 ratio reported for compound 25 in Table 1 in the Example below. Thus, compounds of the present invention may display in-vivo emetogenic effects that are much less than ROLIPRAM™, Ro 20-1724 or other first generation PDE4 inhibitors.

Utility of Compounds and Compositions of the Present Invention

The compounds disclosed herein, or compositions comprising one of more of these compounds and a pharmaceutically acceptable carrier, diluent or excipient, may be used in a method for various treatments and prophylactic effects. For instance, the compounds of the invention may be used for treating or preventing an inflammatory condition or disease in a patient, where the method comprises administering to the patient in need thereof an amount of a compound or composition according to the present invention, where the amount is effective to treat or prevent the inflammatory condition or disease of the patient. The compounds and compositions of the present invention are particularly advantageous in that they provide the desired activity, e.g., treatment of inflammation, without attendant undesirable emetogenic side-effects.

The inflammatory condition or disease may be an autoimmune condition or disease; the inflammatory condition or disease may involve acute or chronic inflammation of bone and/or cartilage compartments of joints; the inflammatory condition or disease may be an arthritis selected from rheumatoid arthritis, gouty arthritis or juvenile rheumatoid arthritis; the inflammatory condition or disease may be asthma; the condition or disease may be associated with the disregulation of T-cells; the condition or disease may be associated with elevated levels of inflammatory cytokines (e.g., wherein the inflammatory cytokine is IL-2, IL-4, IL-5, or Il-12, or wherein the inflammatory cytokine is IFN-γ, or wherein the inflammatory cytokine is TNF-α); the inflammatory condition or disease may be multiple sclerosis; the inflammatory condition or disease may be pulmonary sarcadosis; the inflammatory condition or disease may be ocular inflammation or allergy; the inflammatory condition or disease may be an inflammatory bowel disease (e.g., Crohn's disease or ulcerative colitis); and the inflammatory condition or disease may be an inflammatory cutaneous disease (e.g., psoriasis or dermatitis).

Furthermore, the present invention provides a method for modulating intracellular cyclic adenosine 3',5'-monophosphate levels within a patient, comprising administering to a patient in need thereof an amount of a compound or composition according to the present invention, wherein the amount is effective to modulate the intracellular cyclic adenosine 3',5'-monophosphate levels of the patient. The patient may have an inflammatory condition or disease.

Furthermore, the present invention provides a method for treating or preventing a disease or condition in a patient, where the disease or condition is associated with pathological conditions that are modulated by inhibiting enzymes associated with secondary cellular messengers, the method comprising administering to a patient in need thereof an amount of a compound or a composition of the present invention, wherein the amount is effective to treat or prevent a disease or condition associated with pathological conditions that are modulated by inhibiting enzymes associated with secondary cellular messengers. The enzyme may be a cyclic AMP phosphodiesterase; or the enzyme may be a phosphodiesterase 4.

Furthermore, the present invention provides a method of treating or preventing transplant rejection in a patient, comprising administering to a patient in need thereof an amount of a compound or composition of the present invention, where the amount is effective to treat or prevent transplant rejection in the patient. The rejection may be due to graft versus host disease.

Furthermore, the present invention provides a method of treating or preventing uncontrolled cellular proliferation in a patient, comprising administering to a patient in need thereof an amount of a compound or composition according to the present invention, where the amount is effective to treat or prevent uncontrolled cellular proliferation in the patient. The uncontrolled cellular proliferation may be caused by a cancer selected from leukemia and solid tumors.

Furthermore, the present invention provides a method of treating or preventing conditions associated with the central nervous system (CNS) in a patient, comprising administering to a patient in need thereof an amount of a compound or composition according to the present invention, where the amount is effective to treat or prevent conditions associated with the central nervous system (CNS) in the patient. The condition associated with the central nervous system (CNS) may be depression.

In one aspect the present invention provides a method for treating or preventing an inflammatory condition or disease in a patient. The method includes administering to the patient in need thereof an amount of a benzylated PDE4 inhibitor or composition containing a benzylated PDE4 inhibitor as described in the various inventive aspects and embodiments described herein, where the amount is effective to treat or prevent the inflammatory condition or disease of the patient. Optionally, the benzylated PDE4 inhibitor inhibits an enzyme selected from phosphodiesterase 4 A, B, C or D or any combination thereof including all splice variants of PDE4 A, B, C and D. In one aspect, the inflammatory condition or disease is an autoimmune condition or disease. In another aspect, the inflammatory condition or disease involves acute or chronic inflammation of bone and/or cartilage compartments of joints. In another aspect, the inflammatory condition or disease is an arthritis selected from rheumatoid arthritis, gouty arthritis or juvenile rheumatoid arthritis. In another aspect, the inflammatory condition or disease is asthma. In another aspect, the inflammatory condition or disease is associated with the disregulation of T-cells. In another aspect, the inflammatory condition or disease is associated with elevated levels of inflammatory cytokines. Optionally, the inflammatory cytokine is IL-2, IL-4, IL-5, or IL-12. Optionally, the inflammatory cytokine is IFN-γ. Optionally, the inflammatory cytokine is TNF-α. In another aspect, the inflammatory condition or disease is multiple sclerosis. In another aspect, the inflammatory condition or disease is pulmonary sarcadosis. In another aspect, the inflammatory condition or disease is ocular inflammation or allergy. In another aspect, the inflammatory condition or disease is an inflammatory bowel disease. Optionally, the inflammatory bowel disease is Crohn's disease or ulcerative colitis. In another aspect, the inflammatory condition or disease is an inflammatory cutaneous disease. Optionally, the inflammatory cutaneous disease is psoriasis or dermatitis. In another aspect, the inflammatory condition or disease is chronic obstructive pulmonary disease (COPD), bronchitis, emphysema or acute respiratory distress syndrome (ARDS).

In another aspect the present invention provides a method for treating or preventing a disease or condition in a patient, where the disease or condition is associated with pathological conditions that are modulated by inhibiting enzymes associated with secondary cellular messengers. The inventive method includes administering to the patient in need thereof an amount of a benzylated PDE4 inhibitor or composition containing a benzylated PDE4 inhibitor as described in the various inventive aspects and embodiments described herein, wherein the amount is effective to treat or prevent a disease or condition associated with pathological conditions that are modulated by inhibiting enzymes associated with secondary cellular messengers. In one aspect, the enzyme is a cyclic AMP phosphodiesterase. In another aspect, the enzyme is phosphodiesterase 4.

In another aspect the present invention provides a method for treating or preventing transplant rejection in a patient. The inventive method includes administering to the patient in need thereof an amount of a benzylated PDE4 inhibitor or composition containing a benzylated PDE4 inhibitor as described in the various inventive aspects and embodiments described herein, where the amount is effective to treat or prevent transplant rejection in the patient. In one aspect, the rejection is due to graft versus host disease.

In another aspect the present invention provides a method for treating or preventing uncontrolled cellular proliferation in a patient. The method includes administering to the patient in need thereof an amount of a benzylated PDE4 inhibitor or composition containing a benzylated PDE4 inhibitor as described in the various inventive aspects and embodiments described herein, where the amount is effective to treat or prevent uncontrolled cellular proliferation in the patient. In one aspect, the uncontrolled cellular proliferation is caused by a cancer selected from leukemia and solid tumors.

In another aspect, the present invention provides a method of treating or preventing conditions associated with the central nervous system (CNS) in a patient. The method includes administering to the patient in need thereof an amount of a benzylated PDE4 inhibitor or composition containing a benzylated PDE4 inhibitor as described in the various inventive aspects and embodiments described herein, where the amount is effective to treat or prevent conditions associated with the central nervous system (CNS) in the patient. In one aspect, the condition associated with the CNS is depression. In another aspect, the condition associated with the CNS is long-term memory potentiation and learning enhancement.

In another aspect, the present invention provides a method of treating or preventing diseases in a patient, where the disease is associated with viral infection. The method includes administering to the patient in need thereof an amount of a benzylated PDE4 inhibitor or composition containing a benzylated PDE4 inhibitor as described in the various inventive aspects and embodiments described herein, where the amount is effective to treat or prevent diseases associated with viral infection in the patient. In one aspect, the viral infection is due to the human immunodeficiency virus (HIV) and the disease is acquired immunodeficiency syndrome (AIDS).

In another aspect, the present invention provides a method of treating or preventing diseases in a patient, where the disease is associated with infection by a parasite. The method includes administering to the patient in need thereof an amount of a benzylated PDE4 inhibitor or composition containing a benzylated PDE4 inhibitor as described in the various inventive aspects and embodiments described herein, where the amount is effective to treat or prevent diseases associated with infection of the patient by a parasite. In one aspect, the parasitic infection is due to the *trypanosoma brucei* and the disease is African sleeping sickness disease.

In another aspect, the present invention provides a method of treating or preventing cystic fibrosis in a patient. The method includes administering to the patient in need thereof an amount of a benzylated PDE4 inhibitor or composition containing a benzylated PDE4 inhibitor as described in the various inventive aspects and embodiments described herein, where the amount is effective to treat or prevent cystic fibrosis in the patient.

In a method of the present invention, a benzylated compound, or a composition comprising one or more benzylated and a pharmaceutically acceptable carrier, diluent or excipient, may, although need not, achieve one or more of the following desired results in the subject to whom has been administered a benzylated compound as defined above, or a composition containing one of these compounds and a pharmaceutically acceptable carrier, diluent or excipient:

1. Inhibition of cyclic-AMP phosphodiesterase 4;
2. Low ratio of $IC_{50}$ PDE4(cat):$IC_{50}$PDE4(HARBS);
3. Inhibition of TNF-α production;
4. Inhibition of edema;
5. Inhibition of reactive oxygen species generation from primary neutrophils;
6. Oxygen radical scavenging;
7. Potentiate induction of CRE-mediated transcription activity in human monocytic cells;
8. Inhibition of PDE, preferably PDE4, PDE3, or PDE3 and PDE4;
9. Inhibition of cytokine production by activated T-cell subsets;
10. Inhibition of neutrophil myeloperoxidase release;
11. Inhibition of neutrophil chemotaxis;
12. Inhibition of graft rejection;
13. Inhibition of clinical and histopathological parameters of disease in inflammatory bowel disease;
14. Inhibition of clinical and histopathological parameters of arthritis in a murine collage-induced arthritis model; and
15. Inhibition of clinical and histopathological parameters of disease in an allergan-induced guinea-pig model of acute bronchoconstriction.

Thus, the inventive method may be used to treat inflammation, including both acute and chronic inflammation as well as certain proliferative disorders (cancers). As used herein, inflammation includes, without limitation, ankylosing spondylitis, arthritis (where this term encompasses over 100 kinds of rheumatic diseases), asthma, Crohn's disease, fibromyalgia syndrome, gout, inflammations of the brain (including multiple sclerosis, AIDS dementia, Lyme encephalopathy, herpes encephalitis, Creutzfeld-Jakob disease, and cerebral toxoplasmosis), emphysema, inflammatory bowel disease, irritable bowel syndrome, ischemia-reperfusion injury, juvenile erythematosus, pulmonary sarcoidosis, Kawasaki disease, osteoarthritis, pelvic inflammatory disease, psoriatic arthritis (psoriasis), rheumatoid arthritis, psoriasis, tissue/organ transplant, scleroderma, spondyloarthropathies, systemic lupus erythematosus, pulmonary sarcoidosis, and ulcerative colitis. As used herein, proliferative disorders includes, without limitation, all leukemias and solid tumors that are susceptible to undergoing differentiation or apoptosis upon interruption of their cell cycle.

A method of the present invention is the administration of a therapeutically effective amount of a benzylated compound as described herein including salts, compositions etc. thereof. As used herein, the actual amount encompassed by the term "therapeutically effective amount" will depend on the route of administration, the type of warm-blooded animal being treated, and the physical characteristics of the specific warm-blooded animal under consideration. These factors and their relationship to determining this amount are well known to skilled practitioners in the medical arts. This amount and the method of administration can be tailored to achieve optimal efficacy but will depend on such factors as weight, diet, concurrent medication and other factors that those skilled in the medical arts will recognize.

An effective amount of a compound or composition of the present invention will be sufficient to treat inflammation in a warm-blooded animal, such as a human. Methods of administering effective amounts of anti-inflammatory agents are well known in the art and include the administration of inhalation, oral or parenteral forms. Such dosage forms include, but are not limited to, parenteral solutions, tablets, capsules, sustained release implants and transdermal delivery systems; or inhalation dosage systems employing dry powder inhalers or pressurized multi-dose inhalation devices.

The dosage amount and frequency are selected to create an effective level of the agent without harmful effects. It will generally range from a dosage of about 0.001 to 100 mg/Kg/day, and typically from about 0.01 to 10 mg/Kg/day where administered orally or intravenously. Also, the dosage range will be typically from about 0.001 to 1 mg/Kg/day where administered intranasally or by inhalation.

The following examples are offered by way of illustration and not by way of limitation.

Unless otherwise stated, flash chromatography and column chromatography may be accomplished using Merck silica gel 60 (230–400 mesh). Flash chromatography may be carried out according to the procedure set forth in: "Purification of Laboratory Chemicals", 3rd. edition, Butterworth-Heinemann Ltd., Oxford (1988), Eds. D. D. Perrin and W. L. F. Armarego, page 23. Column chromatography refers to the process whereby the flow rate of eluent through a packing material is determined by gravity. In all cases flash chromatography and radial chromatography may be used interchangeably. Radial chromatography is performed using silica gel on a Chromatotron Model # 7924T (Harrison Research, Palo Alto, Calif.). Unless otherwise stated, quoted $R_f$ values are obtained by thin layer chromatography using Silica Gel 60 $F_{254}$ (Merck KGaA, 64271, Darmstadt, Germany).

Also, unless otherwise stated, chemical reactants and reagents were obtained from standard chemical supply houses, such as Aldrich (Milwaukee, Wis.; www.aldrich.sial.com); EM Industries, Inc. (Hawthorne, N.Y.; www.emscience.com); Fisher Scientific Co. (Hampton, N.H.; www.fischer1.com); and Lancaster Synthesis, Inc. (Windham, N.H.; www.lancaster.co.uk). Gases were obtained from Praxair (Vancouver, B.C.). Cell lines, unless otherwise stated, where obtained from public or commercial sources, e.g., American Tissue Culture Collection (ATCC, Rockville, Md.).

EXAMPLES

Example 1

Formulation of Benzylation Agent from Corresponding Benzyl Alcohol

Scheme 2

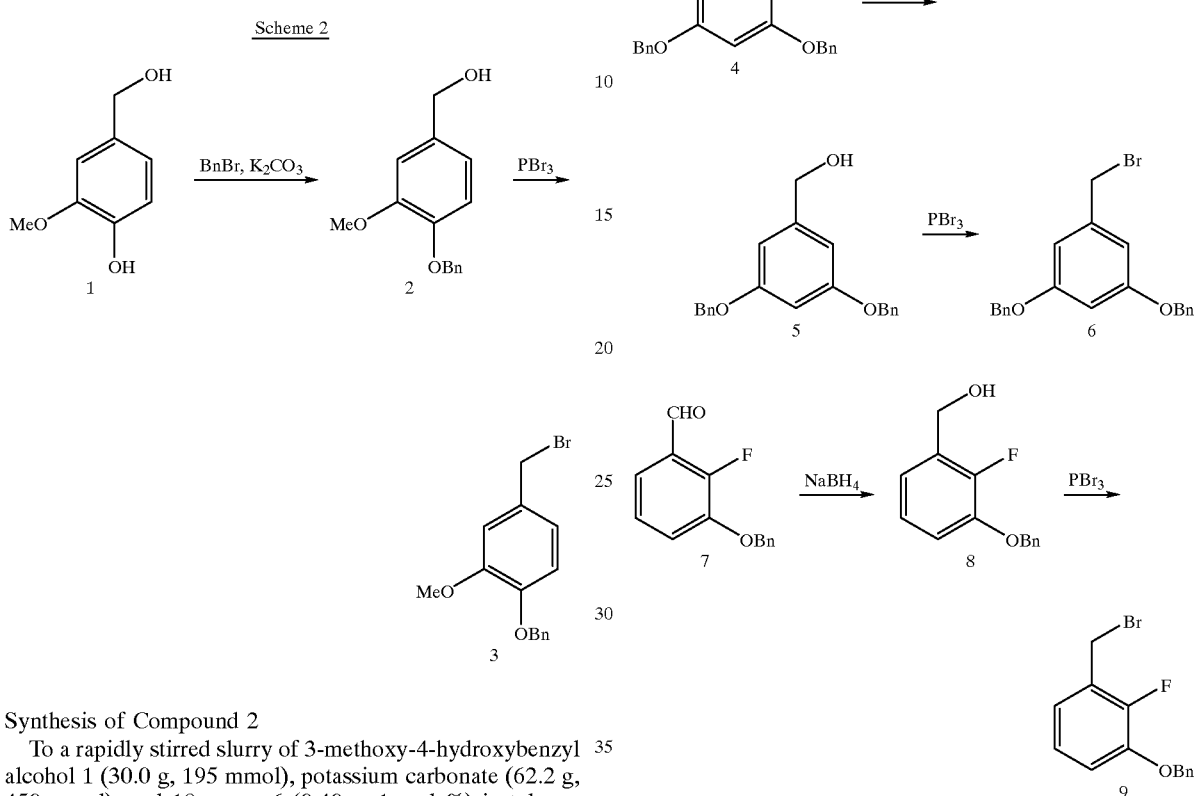

Scheme 3

Synthesis of Compound 2

To a rapidly stirred slurry of 3-methoxy-4-hydroxybenzyl alcohol 1 (30.0 g, 195 mmol), potassium carbonate (62.2 g, 450 mmol), and 18-crown-6 (0.40 g, 1 mol %) in toluene (350 mL) was added a solution of benzyl bromide (BnBr, 25.6 g, 150 mmol) in toluene (150 mL) over 20 min. The reaction mixture was refluxed for 16 hours, after which the mixture was diluted with diethyl ether (400 mL) and washed successively with NaOH (1 N, 2×250 mL), saturated aqueous $NaHCO_3$ (2×250 mL), and brine (2×300 mL). The diethyl ether layer was dried over anhydrous $MgSO_4$, and the solvent was removed to provide a pale yellow solid (42.1 g) which was crystallized with EtOAc and hexanes to give compound 2 (32.7 g, 77%) as a white crystalline solid.

Synthesis of Compound 3

To a solution of alcohol 2 (3.20 g, 13.1 mmol) in anhydrous diethyl ether (15 mL) was added $PBr_3$ (1.77 g, 6.55 mmol) in one portion, and the resulting mixture was stirred at room temperature for 3 hours. The mixture was diluted with diethyl ether (40 mL) and washed with $H_2O$ (2×30 mL), saturated $NaHCO_3$ (2×30 mL), and brine (2×30 mL). The ether layer was dried over anhydrous $MgSO_4$, and the solvent was removed under reduced pressure to afford compound 3 (4.02 g, 100%) as a light yellow solid.

Example 2

Formation of Benzylation Agent from Corresponding Benzyl Aldehyde

Scheme 3 illustrates several procedures for converting commercially available benzyl aldehydes into the corresponding benzyl alcohol. Suitable solvents may be employed in any of these reactions.

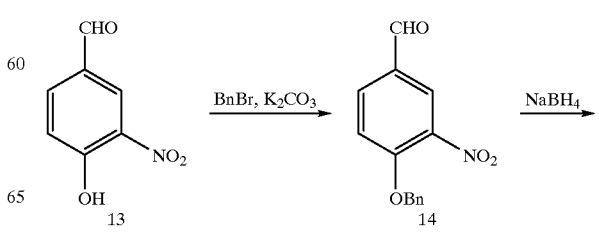

-continued

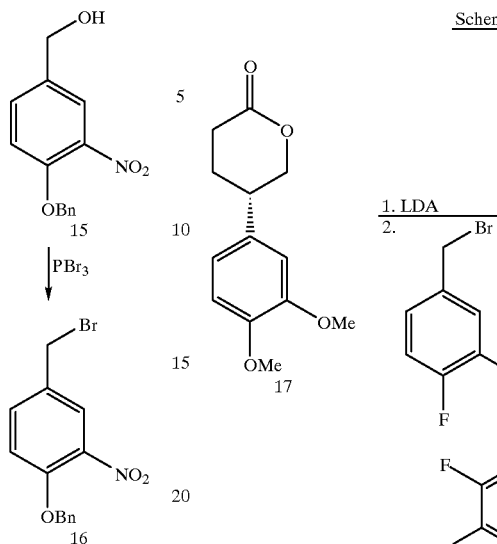

Synthesis of Compound 14

To a suspension of 4-hydroxy-3-nitrobenzaldehyde 13 (3.00 g, 17.95 mmol), potassium carbonate (3.73 g, 26.93 mmol) in DMF (300 mL) was slowly added benzyl bromide (2.85 mL, 23.96 mmol). The reaction mixture was stirred at 65° C. for 18 hours. After cooling to room temperature, the mixture was diluted with water (140 mL) and extracted with diethyl ether (3×150 mL). The combined organic layers were washed with water (150 mL) and brine (150 mL). After drying over anhydrous $MgSO_4$, filtration and evaporation of the filtrate in vacuo gave crude compound 14 (4.39 g, 95%) which was used for the next reaction without further purification.

Synthesis of Compound 15

Compound 14 (4.30 g, 16.72 mmol) was dissolved in $EtOH/CH_2Cl_2$ (1:1, 50 mL) and cooled to 0° C. $NaBH_4$ (0.63 g, 16.72 mmol) was added portionwise. After the addition was completed, the ice-water bath was removed and the reaction mixture was stirred at room temperature for 2 hours. Water (40 mL) was added and the mixture was extracted with $CH_2Cl_2$ (3×60 mL). The combined organic layers were washed with brine (50 mL) and dried over anhydrous $MgSO_4$. Removal of the solvent gave a pale yellow solid which was purified by silica gel column chromatography (hexanes/EtOAc, 1:1) to give compound 15 (4.31 g, 99%) as a pale yellow solid.

Synthesis of Compound 16

To a solution of compound 15 (4.30 g, 16.59 mmol) in anhydrous diethyl ether (40 mL) was slowly added $PBr_3$ (0.79 mL, 8.30 mmol) via syringe, and the resulting mixture was stirred at room temperature for 3 hours. The mixture was diluted with EtOAc (100 mL) and washed with saturated aqueous $NaHCO_3$ (2×50 mL) and brine (2×50 mL). The organic layer was dried over anhydrous $MgSO_4$, and the solvent was removed under reduced pressure to afford compound 16 (5.07 g, 95%) as a pale yellow solid.

Example 3

Formation of Benzylated PDE4 Inhibitor from Benzylation Agent and Corresponding Non-Benzylated Inhibitor A. Benzylation using various halide compounds to provide the desired benzylated products may be achieved as shown in Scheme 4. In Scheme 4, compound 17 is benzylated with commercially available 3,4-difluorobenzyl bromide to give the desired compound 18 in 59% yield.

Synthesis of Compound 18 n-Butyllithium (2.5 M solution in hexanes, 0.56 mL, 1.40 mmol) was added to a solution of diisopropylamine (0.20 mL) in dry THF (10 mL) at −78° C. The mixture was stirred at −78° C. for 1 hour, then HMPA (0.33 mL, 1.91 mmol) was added, followed by addition of a solution of compound 17 (0.30 g, 1.27 mmol) in THF (3 mL). After 1 hour, a solution of 3,4-difluoro benzyl bromide (purchased from Aldrich Chemical Company, Inc., 0.32 mL, 2.54 mmol)) was added in one portion to the reaction, and the resulting mixture was stirred at −78° C. for an additional 4 hours. The excess base was quenched with saturated aqueous $NH_4Cl$ (10 mL), and the resulting solution was extracted with EtOAc (3×20 mL). The combined organic layer was washed with saturated NaCl (2×30 mL), dried over $MgSO_4$, filtered and the filtrate evaporated to dryness. The residue was purified by column chromatography on silica gel (hexanes/EtOAc, 2:1) to give compound 18 (0.27 g, 59%) as a white solid.

B. In Scheme 5, compound 17 is benzylated with 3,4-dibenzyloxy benzyl bromide (prepared by treatment the corresponding alcohol with $PBr_3$), followed by hydrogenation using 10% Pd/C as catalyst to give the desired compound 21 in good yield.

Scheme 5

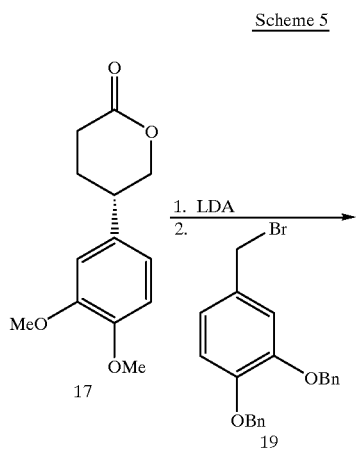

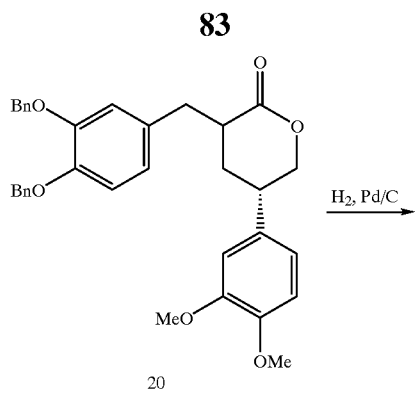

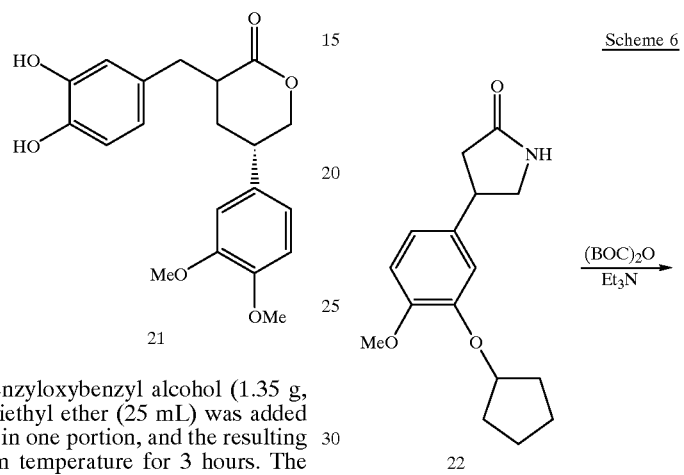

Synthesis of Compound 19

To a solution of 3,4-dibenzyloxybenzyl alcohol (1.35 g, 4.21 mmol) in anhydrous diethyl ether (25 mL) was added $PBr_3$ (0.20 mL, 2.11 mmol) in one portion, and the resulting mixture was stirred at room temperature for 3 hours. The mixture was diluted with diethyl ether (50 mL) and washed with $H_2O$ (2×30 mL), saturated $NaHCO_3$ (2×30 mL), and brine (2×30 mL). The ether layer was dried over anhydrous $MgSO_4$, and the solvent was removed under reduced pressure to afford compound 19 (1.47 g, 91%) as a light yellow oil.

Synthesis of Compound 20 n-Butyllithium (2.5 M solution in hexanes, 0.38 mL, 0.931 mmol) was added to a solution of diisopropylamine (0.14 mL 0.999 mmol) in dry THF (3 mL) at −78° C. The mixture was stirred at −78° C. for 1 hour, then HMPA (0.22 mL, 1.27 mmol) was added, followed by adding a solution of compound 17 (200.0 mg, 0.846 mmol) in THF (3 mL). After 1 hour, a solution of 3,4-dibenzyloxy benzyl bromide (compound 19, 248.5 mg, 0.80 mmol) in THF (1 mL) was added in one portion to the reaction, and the resulting mixture was stirred at −78° C. for an additional 4 hours. The excess base was quenched with saturated aqueous $NH_4Cl$ (10 mL), and the resulting solution was extracted with EtOAc (3×20 mL). The combined organic layer was washed with saturated NaCl (2×30 mL), dried over $MgSO_4$, filtered and the filtrate evaporated to dryness. The residue was purified by column chromatography on silica gel (hexanes/EtOAc, 2:1) to give compound 20 (0.31 g, 67%) as a colorless oil.

Synthesis of Compound 21

A mixture of compound 20 (0.20 g, 0.37 mmol) and 10% Pd/C (25 mg) in EtOAc/AcOH (4:1, 5 mL) was stirred under $H_2$ (balloon) for 2 hours. The mixture was then filtered through a celite plug and the filtrate was evaporated to dryness. The residue was purified by column chromatography on silica gel (hexanes/EtOAc, 3:2) to give compound 21 (0.093 mg, 70%) as a colorless syrup.

Example 4

Formation of Alpha-Benzylated ROLIPRAM™

Further exemplary synthetic methodology to provide a benzylated ROLIPRAM™ compound is described below. For example, as illustrated in Scheme 6, N-protection of 22 (prepared according to the literature procedure: *Journal of Medicinal Chemistry*, 1993, 36, 3274–3277) with di-tert-butyl dicarbonate and triethylamine in dichloromethane provides N-t-butoxycarbonylamide derivative 23. Alkylation of compound 23 with 4-(benzyloxy)-3-methoxybenzyl bromide 3 affords compound 24. Any number of alkylations can be carried out using different halides and the appropriate base such as LDA. Removal of the N-BOC protecting group in with trifluoroacetic acid in dichloromethane gives compound 25. Hydrogenolysis of compound 25 using 10% Pd/C as catalyst provides the desired product 26.

Scheme 6

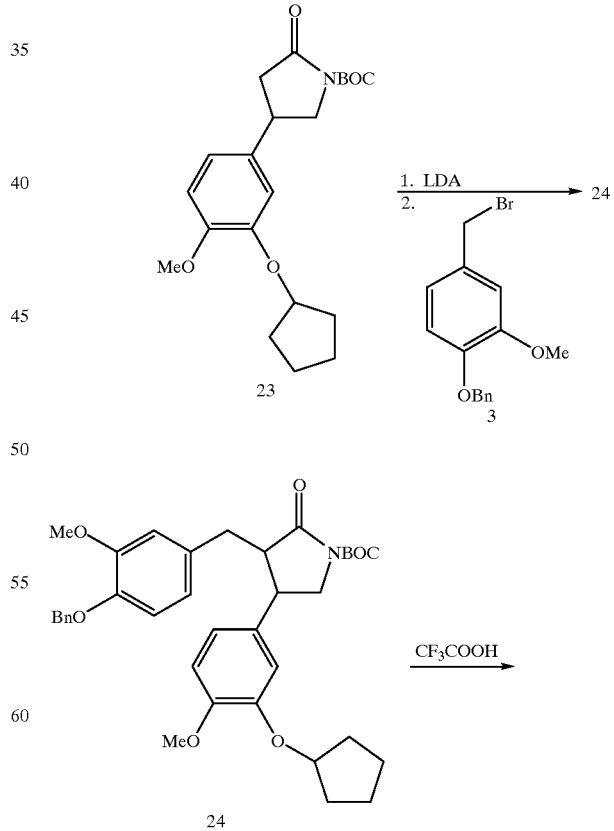

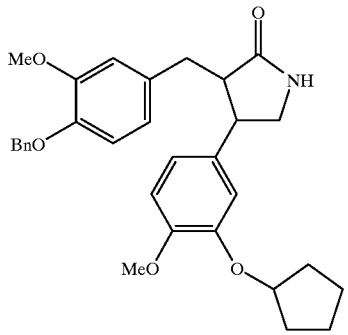

25

↓ H₂, Pd/C

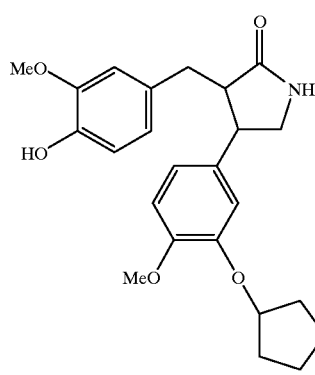

26

Preparation of Compound 23

Di-tert-butyl dicarbonate (0.793 mg, 3.63 mmoles) was added to a solution of compound 22 (0.50 g, 1.82 mmoles), Et₃N (0.50 mL, 3.63 mmoles) and DMAP (0.044 g) in CH₂Cl₂ (14 mL). The mixture was stirred at room temperature for 4 hours. The mixture was concentrated, and the residue was purified by column chromatography on silica gel eluted with hexane/EtOAc (3:2) to afford compound 23 (0.655 g, 96%) as light yellow wax.

Preparation of Compound 24

To a solution of compound 23 (0.649 g, 1.73 mmoles) in dry THF (13 mL) under argon was slowly added LDA [1.20 mmoles, prepared from n-BuLi (0.83 mL, 2.5 M solution in hexane, 1.20 mmoles) and diisopropylamine (0.30 mL, 2.16 mmoles)] in THF (3 mL) at −78° C. The mixture was stirred at −78° C. for one hour, and then DMPU (0.60 mL, 1.50 mmoles) was added to the above mixture via syringe. After 15 minutes, 4-(benzyloxy)-3-methoxybenzyl bromide 3 (1.06 g, 3.46 mmoles) in THF (1.5 mL) was added. The resulting mixture was stirred for an additional 4 hours at −78° C. The excess base was quenched at 0° C. with aqueous saturated NH₄Cl (20 mL), and the resulting solution was extracted with EtOAc (3×30 mL). The combined organic layer was washed with saturated brine (2×30 mL), dried over MgSO₄, filtered and the filtrate was evaporated to dryness. The residue was purified by column chromatography on silica gel eluted with hexanes/EtOAc (7:3) to give compound 24 (0.829 g, 80%) as a white foam.

Preparation of Compound 25

Trifluoroacetic acid (14 mL) was added to a solution of compound 24 (0.820 g, 1.36 mmoles) in CH₂Cl₂ (14 mL). The mixture was stirred at room temperature for 2 hours, diluted with CH₂Cl₂ (100 mL) and washed with saturated NaHCO₃ solution (3×20 mL). The organic layer was dried over MgSO₄, filtered and the filtrate was evaporated to dryness. The residue was purified by column chromatography over silica gel using ethyl acetate as eluent to afford compound 25 (0.510 g, 75%) as white solid.

Preparation of Compound 26

A mixture of compound 25 (0.356 g, 0.710 mmoles) and 10% Pd/C (36 mg) in EtOAc/AcOH (1:1, 12 mL) was stirred under H₂ (balloon pressure) for 18 hours. The mixture was filtered on celite and the filtrate was evaporated to dryness. The residue was purified by column chromatography on silica gel eluted with Hexanes/EtOAc (10:90) to afford compound 26 (0.20 g, 84%) as a white foam.

Example 5

Formation of N-Benzylated ROLIPRAM™

An example of N-benzylation using benzyl halide to provide the desired product 27 is illustrated in Scheme 7. In scheme 7, compound 22 is benzylated with 4-(cyclopentyloxy)-3-methoxybenzyl bromide 44 to provide desire compound 27.

Scheme 7

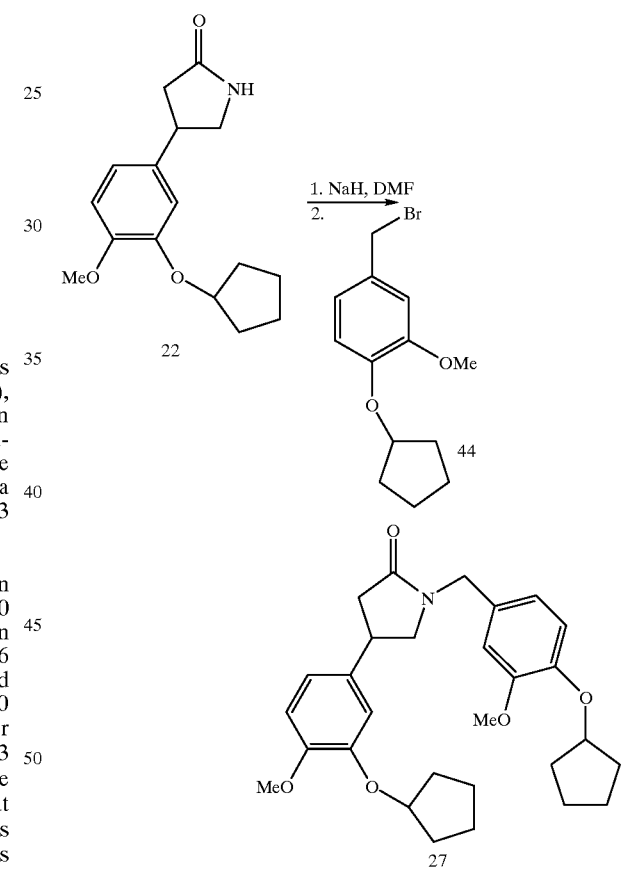

Example 6

Formation of Beta-Benzylated ARIZFLO™ (33)

As illustrated in Scheme 8, compound 28 (prepared according to the literature procedure: *Journal of Medicinal Chemistry*, 1998, 41, 821–835) is alkylated with 4-(benzyloxy)-3-methoxybenzyl bromide 3 to provide compound 29, which is saponified and decarboxylated to cyclohexanone 30 with sodium chloride in hot aqueous DMSO. Cyclohexanone 30 is homologated by a Peterson-type reaction with excess 2-lithio-2-(trimethylsilyl)-1,3-dithiane (prepared from 2-TMF-1,3-dithiane and n-butyl lithium in THF) to provide ketene dithioacetal 31. Methanolysis of compound 31 with mercuric chloride and perchloric acid provides ester 32. Saponification of the ester 32 with potassium hydroxide in a THF/methanol/water solvent mixture, followed by acidification with aqueous HCl, is used to provide the desired product 33.

acid (TsOH) followed by $Pd(OAc)_2$, $Bu_3Sn(OMe)$ and $CH_2CHOCO_2CH_3$. Addition of a benzyl group at the beta position of the cyclohexenone ring may be achieved by a Michael-type addition using commercially available benzylmagnesium chloride as shown in Scheme 9 to yield compound 36. Any number of substituted organomagnesium or organolithium benzyl groups may be prepared and used in Scheme 8

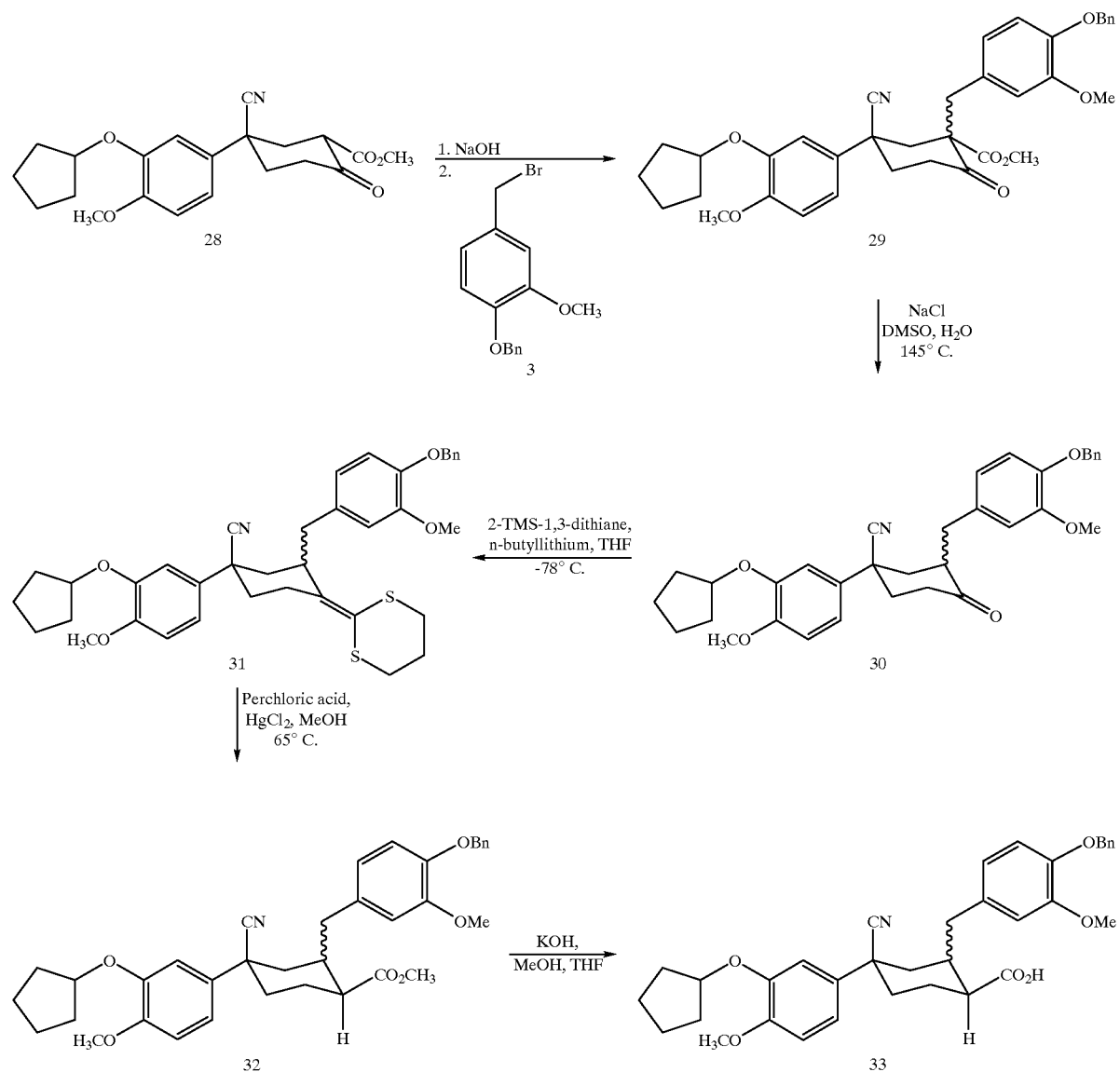

Example 7
Formation of Gamma-Benzylated ARIFLO™ (39)

Exemplary synthetic methodology to introduce a benzyl or substituted benzyl group at the carbon γ to the carbonyl group of a compound of formula (28) is described below. For example, as illustrated in Scheme 9, compound 28 (prepared according to the literature procedure: *Journal of Medicinal Chemistry*, 1998, 41, 821–835) may be saponified and decarboxylated to compound 34 with sodium chloride in hot aqueous DMSO. The cyclohexenone ring may be generated using isopropenyl acetate and p-toluenesulphonic Michael-type reactions according to the methods described in *Comprehensive Organic Transformations, A Guide to Functional Group Preparations*, Second Edition, Richard C. Larock, John Wiley and Sons, Inc., 1999, or referenced therein. Cyclohexanone 36 is homologated by a Peterson-type reaction with excess 2-lithio-2-(trimethylsilyl)-1,3-dithiane to provide ketene dithioacetal 37. Methanolysis of compound 37 with mercuric chloride and perchloric acid provides ester 38. Hydrolysis of the ester 38 with potassium hydroxide in a THF/methanol/water solvent mixture, followed by acidification with aqueous HCl, may provide the desired product 39.

Scheme 9
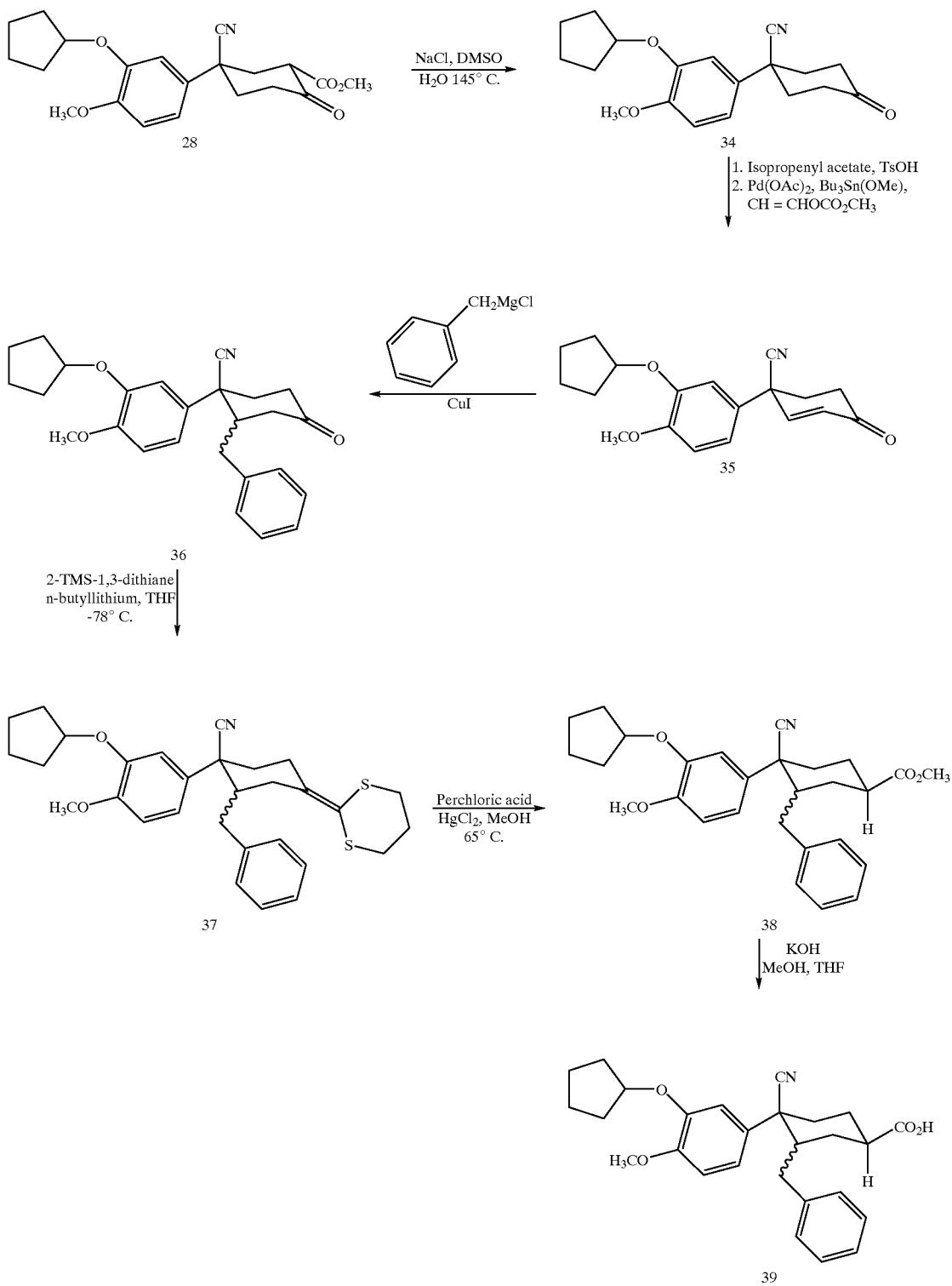
Example 8
Formation of Alpha-Benzylated ARIFLO™ (41)
Treatment of compound 40 (prepared according to the literature procedure: *Journal of Medicinal Chemistry*, 1998, 41, 821–835) with LDA in THF at −78° C., followed by 4-(benzyloxy)-3-methoxybenzyl bromide 44 may provide the desired compound 41. In Scheme 10, Ocyclopentyl represents cyclopentyloxy.

Scheme 10

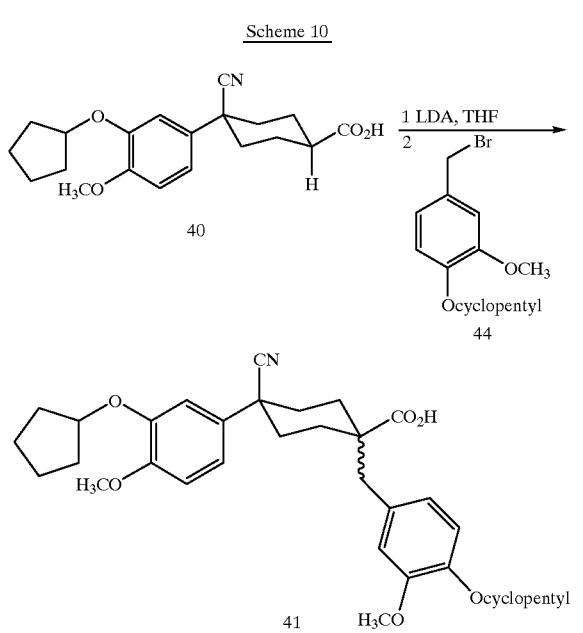

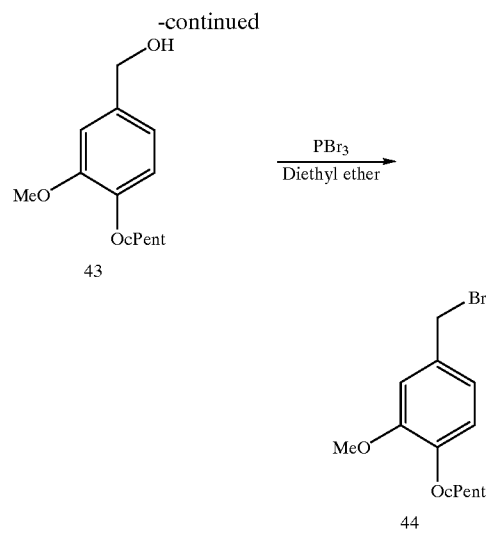

Preparation of Compound 41

To a cooled solution of diisopropylamine in anhydrous THF at −78° C. was added n-butyllithium under argon. The mixture was then stirred at −78° C. for 1 hour. To this was added a solution of compound 40 in a mixture of anhydrous THF and 1,3-dimethyl-3,4,5,6-tetrahydro-2(1H)-pyrimidinone. The reaction mixture was stirred at −78° C. for 1 hour and then 4-(cyclopentyloxy)-3-methoxybenzyl bromide (Compound 44, prepared according to Scheme 11 below) in anhydrous THF was added in one portion. The resulting mixture was stirred at −78° C. for an additional 3 hours, warmed to 0° C., and diluted with 2 N HCl. The aqueous layer was extracted with EtOAc. The combined organic layers were washed with 2 N HCl, followed by brine, and then dried over $MgSO_4$. The mixture was filtered, and the filtrate was evaporated to dryness. The resulting residue was purified by silica gel column chromatography to afford compound 41.

In Scheme 11, treatment of compound 42 with cyclopentyl bromide, potassium iodide and potassium carbonate in DMF gives the corresponding O-cyclopentyl (OcPent) derivative 43, which is treated with $PBr_3$ in diethyl ether to give desired bromide compound 44.

Scheme 11

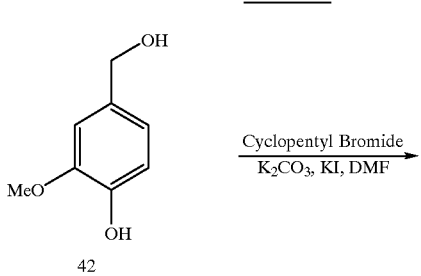

Synthesis of Compound 43

To a suspension of 4-hydroxy-3-methoxybenzyl alcohol 42 (1.00 g, 6.49 mmol), potassium carbonate (1.79 g, 12.98 mmol) and potassium iodide (29.1 mg, 0.175 mmol) in DMF (10 mL) was slowly added cyclopentyl bromide (0.91 mL, 8.44 mmol). The reaction mixture was stirred at 65° C. for 24 hours. After cooling to room temperature, the mixture was diluted with diethyl ether (50 mL) and washed with water (2×25 mL). Drying over anhydrous $MgSO_4$, filtration and evaporation of the filtrate in vacuo gave crude yellow solid which was purified by silica gel column chromatography (hexanes/EtOAc, 3:1) to give compound 43 (0.502 g, 35%) as a pale yellow solid.

Synthesis of Compound 44

To a solution of compound 43 (0.48 g, 2.17 mmol) in anhydrous diethyl ether (8 mL) was slowly added $PBr_3$ (0.10 mL, 1.09 mmol) via syringe, and the resulting mixture was stirred at room temperature for 2 hours. The mixture was diluted with diethyl ether (50 mL) and washed with saturated aqueous $NaHCO_3$ (2×25 mL) and brine (2×25 mL). The organic layer was dried over anhydrous $MgSO_4$, and the solvent was removed under reduced pressure to afford compound 44 (0.577 g, 93%) as a white solid.

Example 9

Formation of N-Benzylated WAY-PDA-641

Exemplary synthetic methodology to introduce a substituted benzyl group into compound 45 is described in Scheme 12. In Scheme 12, compound 45 (i.e., WAY-PDA-641) is treated with NaH in DMF, followed by 3,4-difluorobenzyl bromide to give the desired compound 46 (i.e., benzylated WAY-PDA-641).

93

Scheme 12

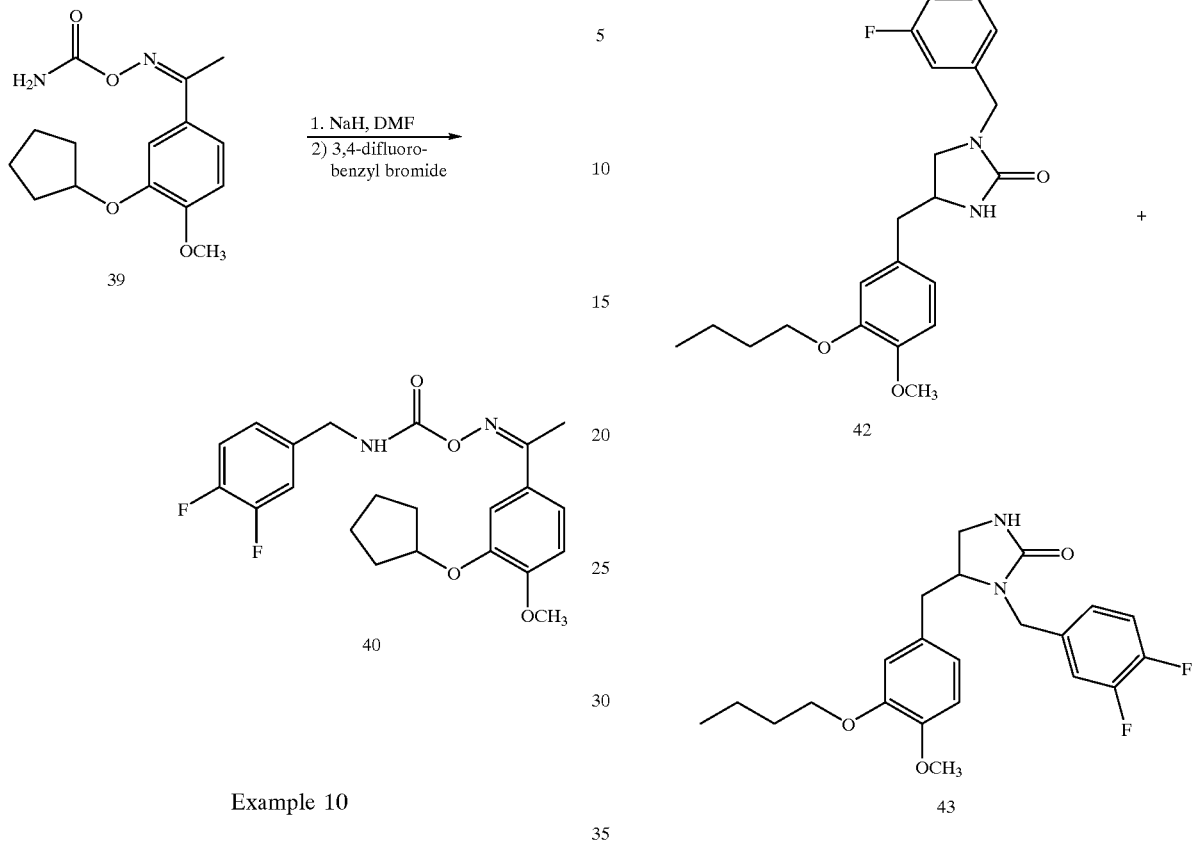

Example 10

Formation of N-Benzylated Ro-20-1724

Exemplary synthetic methodology to introduce a substituted benzyl group into compound 47 is described in Scheme 13. In Scheme 13, compound 47 (i.e., Ro-20-1724) is treated with NaH in DMF, followed by 3,4-difluorobenzyl bromide to give the desired compounds 48 and 49 (i.e., benzylated Ro-20-1724 compounds). Excess NaH and 3,4-difluorobenzyl bromide may be used to provide the compound with benzyl groups on both nitrogens.

94

Example 11

Formation of N-Benzylated RP 73401

Exemplary synthetic methodology to introduce a substituted benzyl group into compound 50 is described in Scheme 14. In Scheme 14, compound 50 (i.e., RP 73401) is treated with NaH in DMF, followed by 3,4-difluorobenzyl bromide to give the desired compound 51 (i.e., benzylated RP 73401).

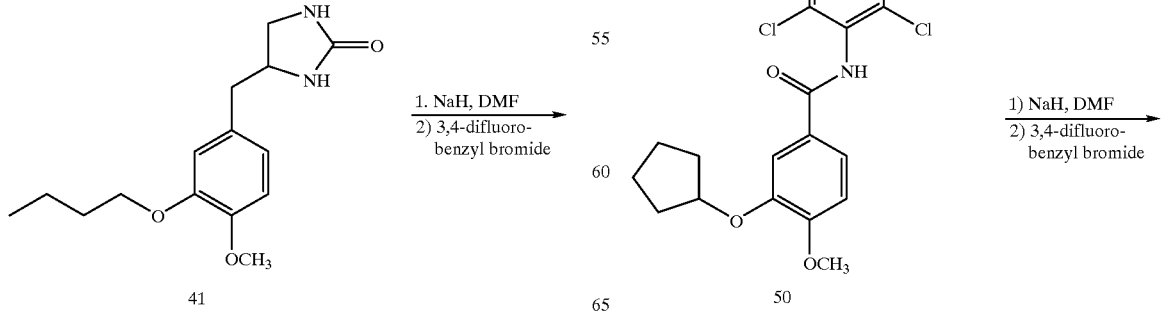

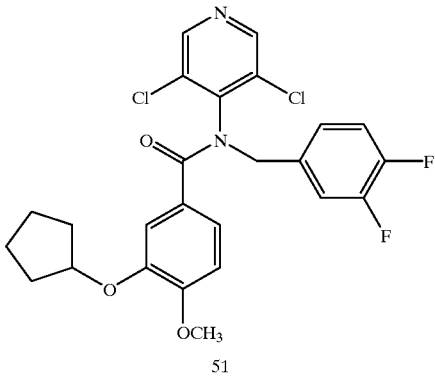

51

Example 12

Formation of N-Benzylated CP-80,633-A

Exemplary synthetic methodology to introduce a substituted benzyl group into compound 52 is described in Scheme 15. In Scheme 15, compound 52 (i.e., CP-80,633-A) is treated with NaH in DMF, followed by 3,4-difluorobenzyl bromide to give the desired compound 53 (i.e., benzylated CP-80,633-A). Excess NaH and 3,4-difluorobenzyl bromide may be used to provide the compound with benzyl groups on both nitrogens.

Scheme 15

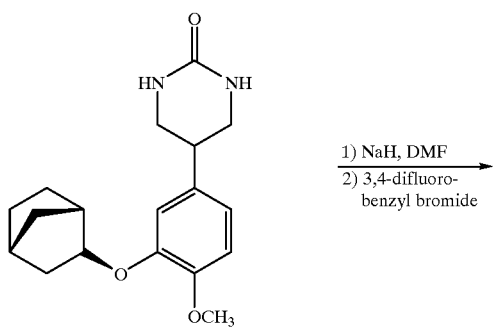

Example 13

Formation of N-Benzylated AROFYLLINE™

Exemplary synthetic methodology to introduce a substituted benzyl group into compound 54 is described in Scheme 16. In Scheme 16, compound 54 (AROFYLLINE™) is treated with NaH in DMF, followed by 3,4-difluorobenzyl bromide to give the desired compound 55 (i.e., benzylated AROFYLLINE™).

Scheme 16

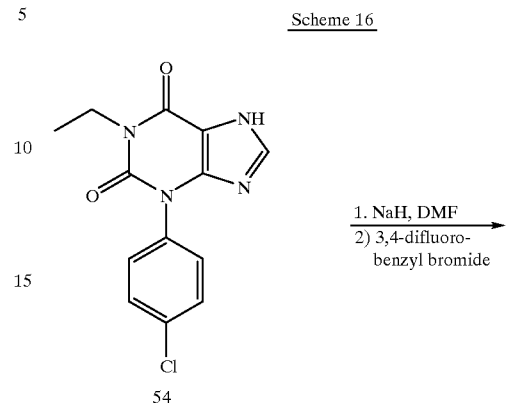

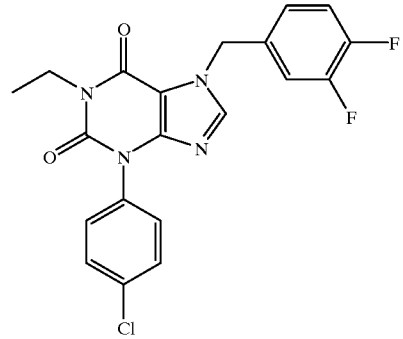

55

Example 14

Formation of N-Benzylated CIPAMFYLLINE™

Exemplary synthetic methodology to introduce a substituted benzyl group into compound 56 is described in Scheme 17. In Scheme 17, compound 56 (i.e., CIPAMFYLLINE™) is treated with KOtBu in DMF, followed by 3,4-difluorobenzyl bromide to give the desired compound 57 (i.e., benzylated CIPAMFYLLINE™).

Scheme 17

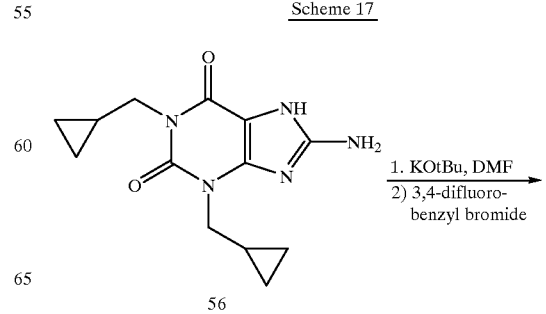

56

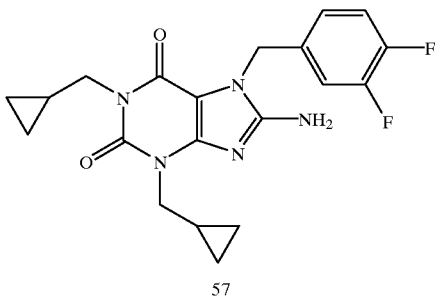

57

Example 15

In vitro Testing for Emetogenic Response

Table 1 shows the PDE4 and HARBS activities of compounds of the present invention compared to that of ROLIPRAM™. Compounds 25 and 26 (see Scheme 6) comprise two different derivatives of ROLIPRAM™ in which the substitution pattern of the added benzyl group at the alpha position differs. As these data clearly show, benzylation at the alpha carbon position of ROLIPRAM™ dramatically reduces the HARBS binding affinity of these derivatives by 92 and 56 fold for compound 26 and 25, respectively. In reducing the HARBS binding affinities the PDE4:HARBS ratios for these compounds is also dramatically reduced to 1.1 and 2.5 for compounds 25 and 26 respectively compared to 65 for ROLIPRAM™. This effect on the HARBS affinities and the ratio of PDE4:HARBS is expected to result in reduced emetogenic potential as well as improved therapeutic window for these compounds.

TABLE 1

EFFECT OF BENZYLATION AT THE ALPHA POSITION OF ROLIPRAM ™ ON POTENCY OF PDE4 INHIBITION AND BINDING TO THE HARBS SITE OF PDE4.

| Compound | α-substitution (+/−benzyl) | PDE4 IC$_{50}$ ($\mu$M) | HARBS IC$_{50}$ ($\mu$M) | Ratio (PDE4/HARBS) |
|---|---|---|---|---|
| ROLIPRAM ™ | No | 0.42 | .0065 | 65.1 |
| 26 | Yes | 1.49 | .6012 | 2.5 |
| 25 | Yes | 0.40 | .3608 | 1.1 |

These data also show that the nature of the alpha-positioned benzyl substituent influences the degree of reduction in HARBS binding as well as the reduction in potency of PDE4 inhibitory activity. The example of compound 25 also shows that the HARBS binding affinity of ROLIPRAM™ may be reduced without affecting the PDE4 inhibitory activity (and anti-inflammatory efficacy) by the correct choice of benzyl substituent.

Table 2 shows the PDE4 and HARBS activities of a compound of the present invention compared to that of ARIFLO™. Compound 41 is a derivative of ARIFLO™ in which a substituted benzyl group has been added to the carbon alpha to the carboxyl group. The data show that benzylation at the alpha position of ARIFLO™ reduces the HARBS binding affinity of this derivative by 7.9 fold relative to that of the parent compound. In this example the potency in inhibition of PDE4 catalytic activity is also reduced 7.5 fold for the benzylated derivative resulting in an improvement in the PDE4/HARBS ratio from 2.4 to 2.2.

TABLE 2

EFFECT OF BENZYLATION AT THE ALPHA POSITION OF ARIFLO ™ ON POTENCY OF PDE4 INHIBITION AND BINDING TO THE HARBS SITE OF PDE4.

| Compound | α-substitution (+/−benzyl) | PDE4 IC$_{50}$ ($\mu$M) | HARBS IC$_{50}$ ($\mu$M) | Ratio (PDE4/HARBS) |
|---|---|---|---|---|
| ARIFLO ™ | No | 0.18 | .076 | 2.4 |
| 41 | Yes | 1.35 | .6012 | 2.2 |

As demonstrated by the above examples for benzylation of ROLIPRAM™, the nature of the added benzyl group (substitution pattern) may strongly influence the degree of improvement of the PDE4:HARBS ratio and therefore a different benzyl group added to the alpha carbon of ARIFLO™ could confer improved ratios relative to the example above.

Additionally, the site of addition of the benzyl group to the PDE4 inhibitor may strongly influence the degree of improvement (reduction) in the PDE 4:HARBS ratio relative to the non-benzylated compound. As such, addition of a benzyl moiety to the beta or gamma carbons of ARIFLO™ may be desirable to that of alpha substitution as in the above example.

Example 16

In vivo Testing for Emetogenic Response

The most recognized pre-clinical animal model for emesis is the ferret. The ferret undergoes a very characteristic, reproducible and well-documented series of behavioral responses, including backward walking, pawing of the mouth, arching of the back, retching and vomiting when dosed with an emetogenic compound. With respect to PDE4 inhibitors their emetogenic potential has been correlated with the ability of compounds to bind to a conformer of the enzyme to which ROLIPRAM™ binds with nanomolar affinity (the HARBS binding site). The central nervous system (CNS) and emetic effects of PDE4 inhibitors are therefore thought in large part to be due to the interaction of these compounds with this particular conformer of PDE4 which is especially prevalent in both the central and peripheral nervous system as well as in cells of the lumen of the gastrointestinal tract (i.e., parietal cells of the stomach).

Benzylation of compounds with PDE4 inhibitory activity (PDE4 inhibitors) according to the present invention has been shown to reduce their HARBS binding potency (see EXAMPLE 15) and thus by logical and rationale extension, based on the existing body of knowledge in the field, to reduce their emetogenic potential. To confirm the in-vitro data of the present invention indicating that incorporation of a benzyl group at the alpha position of ROLIPRAM™ reduces binding to the HARBS conformer of PDE4 compared to that of the parent compound ROLIPRAM™, these two compounds were evaluated for emetogenic potency after intravenous infusion in the ferret model of emesis.

Protocol

Adult male ferrets (*Mustela putorius furo,* sable, 0.75–1.5 kg, Marshall Farms, USA) were quarantined and acclimated to the testing facility for seven days prior to initiation of the study. For intravenous infusion dosing, a catheter was surgically inserted in the jugular vein a minimum of 14 hours prior to administration of test articles and the catheter was maintained for patency by flushing with heparin solution daily. After surgery for catheter insertion the ferrets were individually housed in cages. Animals were fasted 12–16 hours prior to dosing and during the behavioral assessment period. They were returned to normal food diet after the observation periods. Animals found acceptable for inclusion in the study were randomly assigned to the each of the study groups (n=3 for each of the two treatment groups and n=3 for the vehicle negative control group).

Test compounds (ROLIPRAM™ and Compound 25) were freshly dissolved on the day of dosing in the vehicle, polyethylene glycol (PEG) 200 (Sigma catalogue number P-3015), to the required concentration in order to achieve the target dose. Animals in the control (PEG 200) and treatment (ROLIPRAM™ or Compound 25) groups were administered the dosing formulation at 3 ml/kg by intravenous infusion over a 5 minute period via the catheter inserted in the jugular. Continual observation for signs of emetic behavior were begun for each of the animals in the study groups immediately following completion of the 5 minute dosing period and for a period of three hours. Sequential recordings of emetic behaviour were noted on a separate data collection sheet for each animal which included the time of onset of each event as well as the duration and nature of the event (i.e., retching, gagging, vomiting, back arching, backward walking etc.).

The target doses for each of the test articles are shown below in Table 3. If animals expressed no emetic behaviour at the lowest dosage then animals were dosed again with semi-log increasing doses of test article and the three hour observation period repeated until the emetic threshold (lowest of test doses causing emesis) was reached or until the highest of the 4 target doses was completed. There was a 24 hr. washout period between each of the successive ascending doses of test article to allow the compound to clear the animals' system. For a dose level to be considered at the threshold of emesis at least one of the ferrets must have exhibited definite emetic signs (i.e., retching and/or vomiting). If the emetic response was minimal at a particular dose level then the next dose level could be performed to confirm the threshold level.

TABLE 3

STUDY GROUP DESIGNATIONS FOR DETERMINATION OF EMETIC THRESHOLD IN FERRETS OF ROLIPRAM ™ AND BENZYLATED ROLIPRAM ™

| Treatment | No. of animals | Route | Dosage (mg/kg) |
|---|---|---|---|
| Vehicle (PEG 200) | 3 | i.v. | — |
| ROLIPRAM ™ | 3 | i.v. | 0.03, 0.1, 0.3, 1.0 |
| Compound 25 | 3 | i.v. | 0.1, 0.3, 1.0, 3.0 |

Results

Table 4 shows the dosage required for each of the test compounds (rolipram and compound 25) to achieve a threshold emetic response after 5 minutes intravenous infusion in the ferret. A threshold emetic response was achieved after dosing with 0.3 mg/kg rolipram. At this dosage level of rolipram, one of the three ferrets exhibited a definite emetic response as shown by 5 mild retches observed over a time period of 9 minutes starting at 10 minutes post-dosing. Emetic signs were also evident for rolipram at the previous 0.1 mg/kg dose level.

In contrast to rolipram there was no emetic behaviour whatsoever demonstrated by the ferrets administered compound 25 up to and including the highest dose level tested (3 mg/kg). Thus for compound 25 the emetic threshold in ferrets is greater than 3 mg/kg after intravenous infusion dosing. These data therefore show that at least 10-fold higher doses of the benzylated compound are required to achieve emesis compared to the non-benzylated compound, rolipram. Since these compounds have equivalent PDE4 catalytic inhibitory activity, the benzylated compound in addition to being significantly less emetic than its non-benzylated parent, would be expected to have similar anti-inflammatory efficacy and thus a markedly improved therapeutic ratio.

These in-vivo data demonstrated in the ferret model of emesis, therefore confirm and support the in-vitro biochemical findings presented above that benzylation reduces binding of compounds to the HARBS conformer of PDE4 and thus reduces their emetogenic potential.

TABLE 4

COMPARISON OF THE EMETIC THRESHOLD OF ROLIPRAM AND BENZYLATED ROLIPRAM AFTER INTRAVENOUS INFUSION IN FERRETS

| Treatment | Emetic Threshold (mg/kg) |
|---|---|
| Rolipram | 0.3 |
| Compound 25 | >3.0 |

All publications and patent applications mentioned in this specification are herein incorporated by reference to the same extent as if each individual publication or patent application was specifically and individually incorporated by reference. For example, the book in *Comprehensive Organic Transformations, A Guide to Functional Group Preparations,* Second Edition, Richard C. Larock, John Wiley and Sons, Inc., 1999, and particularly the references cited therein, is incorporated herein by reference for all purposes.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A compound of the formula

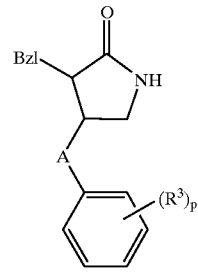

and isolated stereoisomers, salts and solvates thereof, wherein

Bzl is a benzyl group of the formula

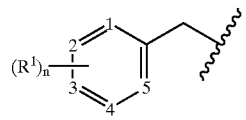

wherein each of the numerals 1, 2, 3, 4 and 5 is carbon, with the proviso that the ring is aromatic;

n is 5 and $R^1$ at each occurrence is independently selected from halogen, nitro, $R^2$, $NR^2_{(m)}$, and $OR^2$ wherein m=0, 1, 2, or 3 and $R^2$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, C$_6$–C$_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with C$_1$–C$_4$alkyl and indanyl; wherein the alkyl portion of an R$^2$ group may be optionally substituted with one or more fluorine atoms, hydroxyl or C$_1$–C$_8$alkoxy; and the aryl portion of an R$^2$ group may be optionally substituted with C$_1$–C$_8$alkyl, C$_1$–C$_8$alkoxy or halogen;

A is selected from a direct bond, optionally substituted C$_1$–C$_5$alkylene, optionally substituted C$_2$–C$_5$alkenyl and optionally substituted phenylene;

p is 5 and R$^3$ at each occurrence is independently selected from halogen, nitro, R$^4$, NR$^4_{(q)}$, and OR$^4$ wherein q=0, 1, 2, or 3 and R$^4$ at each occurrence is independently selected from H, C$_1$–C$_8$alkyl, alkoxyalkyl having 3–7 carbons in the alkoxy portion and 2–4 carbons in the alkyl portion, phenoxyalkyl having 2–6 carbons in the alkyl portion, C$_3$–C$_7$cycloalkyl, C$_6$–C$_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with C$_1$–C$_4$alkyl and indanyl; wherein the alkyl portion of an R$^4$ group may be optionally substituted with one or more fluorine atoms, hydroxyl or C$_1$–C$_8$alkoxy; and the aryl portion of an R$^4$ group may be optionally substituted with C$_1$–C$_8$alkyl, C$_1$–C$_8$alkoxy or halogen;

with the proviso that R$^3$ at the para position relative to A is alkoxy, and R$^3$ at one meta position is selected from alkyl having at least 3 carbons and alkoxy having at least 3 carbons.

2. The compound of claim 1 wherein each of the numerals 1, 2, 3, 4 and 5 is carbon, with the proviso that the ring is aromatic; and n is 5 and R$^1$ at each occurrence is independently selected from halogen, nitro, R$^2$, and OR$^2$ wherein and R$^2$ at each occurrence is independently selected from H, C$_1$–C$_8$alkyl, alkoxyalkyl having 3–7 carbons in the alkoxy portion and 2–4 carbons in the alkyl portion, phenoxyalkyl having 2–6 carbons in the alkyl portion, C$_3$–C$_7$cycloalkyl, C$_6$–C$_9$polycycloalkyl, alkylcycloalkyl, hydroxyalkyl, carboxylate, alkylcarboxylate, carboxyl, alkyl carboxyl, amide, alkylamide, phenyl, phenylalkyl having 1–8 carbons in the alkyl portion, phenylaminoalkyl having 2–6 carbons in the alkyl portion and the amino may be optionally substituted with C$_1$–C$_4$alkyl and indanyl; wherein the alkyl portion of an R$^2$ group may be optionally substituted with one or more fluorine atoms, hydroxyl or C$_1$–C$_8$alkoxy; and the phenyl portion of an R$^2$ group may be optionally substituted with C$_1$–C$_8$alkyl, C$_1$–C$_8$alkoxy or halogen.

3. A compound of claim 1 wherein each of the numerals 1, 2, 3, 4 and 5 is carbon, with the proviso that the ring is aromatic; and n is 5 and R$^1$ at each occurrence is independently selected from halogen, nitro, R$^2$, NR$^2_{(m)}$, and OR$^2$ wherein m=0, 1, 2, or 3 and R$^2$ at each occurrence is independently selected from H, C$_1$–C$_8$alkyl, alkoxyalkyl having 3–7 carbons in the alkoxy portion and 2–4 carbons in the alkyl portion, phenoxyalkyl having 2–6 carbons in the alkyl portion, C$_3$–C$_7$cycloalkyl, C$_6$–C$_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with C$_1$–C$_4$alkyl and indanyl; wherein the alkyl portion of an R$^2$ group may be optionally substituted with one or more fluorine atoms, hydroxyl or C$_1$–C$_8$alkoxy; and the aryl portion of an R group may be optionally substituted with C$_1$–C$_8$alkyl, C$_1$–C$_8$alkoxy or halogen; with the proviso that either (a) at least one R$^1$ is OR$^2$, or (b) the benzyl ring contains at least two R$^1$ groups that are not hydrogen.

4. A compound of claim 1 wherein the phenyl group has the formula

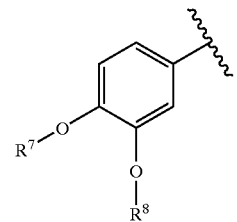

wherein R$^7$ is selected from methyl, ethyl, difluoromethyl and trifluoromethyl; and R$^8$ is selected from C$_3$–C$_8$alkyl, alkoxyalkyl having 3–7 carbons in the alkoxy portion and 2–4 carbons in the alkyl portion, phenoxyalkyl having 2–6 carbons in the alkyl portion, C$_3$–C$_7$cycloalkyl, C$_6$–C$_9$polycycloalkyl, phenylalkyl having 1–8 carbons in the alkyl portion, phenylaminoalkyl having 2–6 carbons in the alkyl portion and the amino may be optionally substituted with C$_1$–C$_4$alkyl and indanyl; wherein the alkyl portion of an R$^2$ group may be optionally substituted with one or more fluorine atoms, hydroxyl or C$_1$–C$_4$alkoxy; and the aryl portion of an group may be optionally substituted with C$_1$–C$_4$alkyl, C$_1$–C$_4$alkoxy or halogen.

5. A compound of claim 4 wherein R$^8$ is not cyclopentyl.

6. A compound of claim 1 wherein A is a direct bond; and in at least one occurrence, R$^3$ is OR$^4$ wherein R$^4$ is selected from C$_1$–C$_8$alkyl, C$_3$–C$_7$cycloalkyl, and C$_6$–C$_9$polycycloalkyl.

7. A compound of claim 1 having the formula

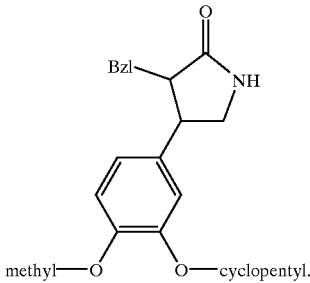

8. A compound of claim 1 wherein A is selected from a direct bond, C$_1$–C$_5$alkylene, C$_2$–C$_5$alkenyl and phenylene.

9. A compound of claim 1 wherein, at the meta position relative to the A group on the R$^3$-substituted phenyl ring, R$^3$ is alkoxy having at least three carbon atoms, excluding cyclopentyloxy, and at the para position R$^1$ is not hydrogen.

10. A compound of claim 1 wherein each of the numerals 1, 2, 3, 4 and 5 is carbon; and n is 5 and $R^1$ at each occurrence is independently selected from halogen, nitro, $R^2$, $NR^2_{(m)}$, and $OR^2$ wherein m=0, 1, 2, or 3 and $R^2$ at each occurrence is independently selected from H, $C_1$–$C_8$alkyl, alkoxyalkyl having 3–7 carbons in the alkoxy portion and 2–4 carbons in the alkyl portion, phenoxyalkyl having 2–6 carbons in the alkyl portion, $C_3$–$C_7$cycloalkyl, $C_6$–$C_9$polycycloalkyl, alkylcycloalkyl, hydroxyalkyl, carboxylate, alkylcarboxylate, carboxyl, alkyl carboxyl, amide, alkylamide, aryl, heteroaryl, heteroalkyl, heterocycloalkyl, phenylalkyl having 1–8 carbons in the alkyl portion, phenylaminoalkyl having 2–6 carbons in the alkyl portion and the amino may be optionally substituted with $C_1$–$C_4$alkyl and indanyl; wherein the alkyl portion of an group may be optionally substituted with one or more fluorine atoms, hydroxyl or $C_1$–$C_8$alkoxy; and the aryl portion of an $R^2$ group may be optionally substituted with $C_1$–$C_8$alkyl, $C_1$–$C_8$alkoxy or halogen; with the proviso that at least one $R^1$ is halogen.

11. A compound of claim 1 wherein aryl is a phenyl ring.

\* \* \* \* \*

UNITED STATES PATENT AND TRADEMARK OFFICE
CERTIFICATE OF CORRECTION

PATENT NO.  : 6,555,572 B2
DATED       : April 29, 2003
INVENTOR(S) : Ronald W. Lauener It is certified that error appears in the above-identified patent and that said Letters Patent is hereby corrected as shown below:

Column 102,
Line 41, "of an group" should read as -- of an $R^2$ group --.

Column 104,
Line 4, "of an group" should read as -- of an $R^2$ group --.

Signed and Sealed this

Twenty-first Day of September, 2004

JON W. DUDAS
*Director of the United States Patent and Trademark Office*